(12) United States Patent
Houlihan et al.

(10) Patent No.: US 8,455,176 B2
(45) Date of Patent: Jun. 4, 2013

(54) COATING COMPOSITION

(75) Inventors: Francis Houlihan, Millington, NJ (US); Lin Zhang, Edison, NJ (US); Alberto Dioses, Doylestown, PA (US); Meng Li, Edison, NJ (US)

(73) Assignee: AZ Electronic Materials USA Corp., Somerville, NJ (US)

( * ) Notice: Subject to any disclaimer, the term of this patent is extended or adjusted under 35 U.S.C. 154(b) by 0 days.

(21) Appl. No.: 12/269,072

(22) Filed: Nov. 12, 2008

(65) Prior Publication Data

US 2010/0119972 A1 May 13, 2010

(51) Int. Cl.
*G03F 7/031* (2006.01)
*G03F 7/039* (2006.01)
*G03F 7/095* (2006.01)
*G03F 7/38* (2006.01)
*G03F 7/40* (2006.01)
*G03F 7/30* (2006.01)

(52) U.S. Cl.
USPC ............... 430/288.1; 430/270.1; 430/326; 430/311; 430/330; 430/927

(58) Field of Classification Search
None
See application file for complete search history.

(56) References Cited

U.S. PATENT DOCUMENTS

| | | | |
|---|---|---|---|
| 3,523,795 A | 8/1970 | Ohkubo et al. | |
| 4,061,465 A | 12/1977 | Franklin et al. | |
| 4,229,274 A * | 10/1980 | Carlblom | 522/8 |
| 4,388,450 A | 6/1983 | Crivello | |
| 4,491,628 A | 1/1985 | Ito et al. | |
| 4,845,265 A | 7/1989 | Lapin et al. | |
| 4,863,827 A | 9/1989 | Jain et al. | |
| 4,910,122 A | 3/1990 | Arnold et al. | |
| 5,069,997 A | 12/1991 | Schwalm et al. | |
| 5,114,826 A * | 5/1992 | Kwong et al. | 430/192 |
| 5,147,946 A | 9/1992 | Liu | |
| 5,286,867 A | 2/1994 | Lohaus et al. | |
| 5,338,641 A | 8/1994 | Pawlowski et al. | |
| 5,340,682 A | 8/1994 | Pawlowski et al. | |
| 5,350,660 A | 9/1994 | Urano et al. | |
| 5,354,643 A | 10/1994 | Cabrera et al. | |
| 5,362,608 A | 11/1994 | Flaim et al. | |
| 5,482,817 A * | 1/1996 | Dichiara et al. | 430/271.1 |
| 5,585,219 A | 12/1996 | Kaimoto et al. | |
| 5,635,333 A | 6/1997 | Petersen et al. | |
| 5,648,194 A | 7/1997 | Pai et al. | |
| 5,650,261 A | 7/1997 | Winkle | |
| 5,652,297 A | 7/1997 | McCulloch et al. | |
| 5,716,756 A | 2/1998 | Pawlowski et al. | |
| 5,731,386 A | 3/1998 | Thackeray et al. | |
| 5,837,420 A | 11/1998 | Aoai et al. | |
| 5,843,624 A | 12/1998 | Houlihan et al. | |
| 5,876,900 A | 3/1999 | Watanabe et al. | |
| 5,880,168 A | 3/1999 | Heinz et al. | |
| 5,880,169 A | 3/1999 | Osawa et al. | |
| 5,882,996 A | 3/1999 | Dai | |
| 5,886,102 A | 3/1999 | Sinta et al. | |
| 5,935,760 A | 8/1999 | Shao et al. | |
| 5,939,234 A | 8/1999 | Yamanaka et al. | |
| 5,939,235 A | 8/1999 | Kondo et al. | |
| 5,939,236 A | 8/1999 | Pavelchek et al. | |
| 5,972,560 A | 10/1999 | Kaneko et al. | |
| 5,981,145 A | 11/1999 | Ding et al. | |
| 5,997,993 A * | 12/1999 | Bi et al. | 428/195.1 |
| 6,033,830 A | 3/2000 | Sinta et al. | |
| 6,054,254 A | 4/2000 | Sato et al. | |
| 6,080,530 A | 6/2000 | Shao et al. | |
| 6,103,445 A * | 8/2000 | Willson et al. | 430/270.1 |
| 6,110,653 A | 8/2000 | Holmes et al. | |
| 6,111,143 A | 8/2000 | Park et al. | |
| 6,114,085 A | 9/2000 | Padmanaban et al. | |
| 6,124,077 A | 9/2000 | Imai et al. | |
| 6,132,926 A | 10/2000 | Jung et al. | |
| 6,187,506 B1 | 2/2001 | Ding et al. | |
| 6,200,728 B1 | 3/2001 | Cameron et al. | |
| 6,207,342 B1 * | 3/2001 | Takechi et al. | 430/270.1 |
| 6,251,562 B1 | 6/2001 | Breyta et al. | |
| 6,319,651 B1 | 11/2001 | Holmes et al. | |
| 6,338,934 B1 * | 1/2002 | Chen et al. | 430/270.1 |
| 6,358,665 B1 | 3/2002 | Pawlowski et al. | |
| 6,395,450 B1 | 5/2002 | Park et al. | |
| 6,447,980 B1 | 9/2002 | Rahman et al. | |
| 6,455,230 B1 * | 9/2002 | Damme et al. | 430/302 |
| 6,723,488 B2 | 4/2004 | Kudo et al. | |
| 6,803,172 B2 | 10/2004 | Jung et al. | |
| 6,831,285 B2 | 12/2004 | Hol et al. | |
| 6,844,131 B2 | 1/2005 | Oberlander et al. | |
| 6,846,612 B2 | 1/2005 | Deshpande | |
| 6,866,984 B2 | 3/2005 | Jung et al. | |
| 7,223,518 B2 | 5/2007 | Henderson et al. | |

(Continued)

FOREIGN PATENT DOCUMENTS

| | | |
|---|---|---|
| EP | 0 794 458 A2 | 9/1997 |
| JP | 56-47440 A | 4/1981 |

(Continued)

OTHER PUBLICATIONS

Notice of Allowance and Fee(s) Due dated Jun. 16, 2010 from U.S. Appl. No. 11/876,332, which is a divisional of U.S. Appl. No. 10/808,884.
Notice of Allowance and Fee(s) Due dated May 27, 2010 from U.S. Appl. No. 11/877,891, which is a divisional of U.S. Appl. No. 10/808,884.
Notice of Allowance and Fee(s) Due dated Jul. 8, 2010 from U.S. Appl. No. 11/877,891, which is a divisional of U.S. Appl. No. 10/808,884.
Form PCT/ISA/220, Form PCT/ISA/210, and Form PCT/ISA/237 for PCT/IB2009/007451 dated Aug. 2, 2010, which corresponds to U.S. Appl. No. 12/269,072.
English Language Abstract from JPO of JP 56-47440 A, Printed Out Dec. 2009.

(Continued)

*Primary Examiner* — Cynthia Hamilton
(74) *Attorney, Agent, or Firm* — Sangya Jain

(57) ABSTRACT

Developable bottom antireflective coating compositions are provided.

12 Claims, No Drawings

U.S. PATENT DOCUMENTS

| | | |
|---|---|---|
| 7,265,431 B2 | 9/2007 | Sivakumar |
| 7,358,408 B2 | 4/2008 | Rahman et al. |
| 7,514,202 B2 | 4/2009 | Ohsawa et al. |
| 7,521,170 B2 | 4/2009 | Rahman et al. |
| 7,521,483 B2 | 4/2009 | Davey et al. |
| 7,541,134 B2 | 6/2009 | Iwabuchi et al. |
| 7,678,528 B2 | 3/2010 | Rahman et al. |
| 7,816,071 B2 | 10/2010 | Abdallah et al. |
| 7,824,837 B2 | 11/2010 | Wu et al. |
| 8,039,202 B2 | 10/2011 | Sui et al. |
| 8,088,548 B2 | 1/2012 | Houlihan et al. |
| 2002/0012880 A1 | 1/2002 | Imai et al. |
| 2002/0045130 A1 | 4/2002 | Nitta et al. |
| 2002/0094382 A1 | 7/2002 | Imai et al. |
| 2003/0129547 A1 | 7/2003 | Neisser et al. |
| 2003/0162120 A1 | 8/2003 | Yoon et al. |
| 2003/0215736 A1 | 11/2003 | Oberlander et al. |
| 2004/0018451 A1 | 1/2004 | Choi |
| 2004/0152009 A1* | 8/2004 | Yamaguchi et al. ....... 430/270.1 |
| 2005/0053850 A1 | 3/2005 | Askebjer et al. |
| 2005/0064326 A1 | 3/2005 | Yasunami et al. |
| 2005/0095532 A1 | 5/2005 | Kodama et al. |
| 2005/0106501 A1 | 5/2005 | Van Aert et al. |
| 2005/0214674 A1 | 9/2005 | Sui et al. |
| 2005/0255410 A1 | 11/2005 | Guerrero et al. |
| 2005/0271974 A1 | 12/2005 | Rahman et al. |
| 2005/0277058 A1 | 12/2005 | Iwabuchi et al. |
| 2005/0287816 A1 | 12/2005 | Blalock et al. |
| 2006/0183348 A1 | 8/2006 | Meagley et al. |
| 2007/0031760 A1* | 2/2007 | Chang et al. .................. 430/311 |
| 2007/0184648 A1 | 8/2007 | Yoon et al. |
| 2007/0219368 A1* | 9/2007 | Iwabuchi et al. .................. 544/5 |
| 2008/0008955 A1 | 1/2008 | Brodsky et al. |
| 2008/0038666 A1 | 2/2008 | Wu et al. |
| 2008/0090184 A1 | 4/2008 | Sui et al. |
| 2008/0138744 A1 | 6/2008 | Hatanaka et al. |
| 2008/0166667 A1 | 7/2008 | Goldfarb |
| 2009/0104559 A1 | 4/2009 | Houlihan et al. |

FOREIGN PATENT DOCUMENTS

| | | |
|---|---|---|
| JP | 6-295064 A | 10/1994 |
| JP | 2001-22057 A | 1/2001 |
| JP | 2004-31569 A | 1/2004 |
| JP | 2009-107996 A | 5/2009 |
| WO | WO 97/33198 A1 | 9/1997 |
| WO | WO 2005/093513 A2 | 10/2005 |

OTHER PUBLICATIONS

Database WPI Week 198125 Thomson Scientific, London, GB; AN 1981-44838D XP002546976 & JP 56 047440 A (Japan Synthetic Rubber Co Ltd) Apr. 30, 1981 & JP 56 047440 A (Japan Synthetic Rubber Co Ltd) Apr. 30, 1981.
English Language Abstract from Derwent of JP 2001-22057 A, Copyright 2008.
Form PCT/ISA/220, Form PCT/ISA/210 and Form PCT/IBSA/237 for PCT/IB2005/000773 dated Jul. 27, 2005 which corresponds to U.S. Appl. No. 10/808,884.
Form PCT/IB/326, Form PCT/IB/373 and Form PCT/IBSA/237 for PCT/IB2005/000773 dated Oct. 5, 2006 which corresponds to U.S. Appl. No. 10/808,884.
Office Action dated Jun. 24, 2008 from U.S. Appl. No. 11/876,332, which is a divisional of prior application U.S. Appl. No. 10/808,884.
Office Action dated Jan. 27, 2009 from U.S. Appl. No. 11/876,332, which is a divisional of U.S. Appl. No. 10/808,884.
Office Action dated Mar. 13, 2009 from U.S. Appl. No. 11/876 332 which is a divisional of U.S. Appl. No. 10/808,884.
Office Action Oct. 30, 2009 from U.S. Appl. No. 11/876,332, which is a divisional of U.S. Appl. No. 10/808,884.
Notice of Allowance and Fee(s) Due from U.S. Appl. No. 11/876,332, which is a divisional of U.S. Appl. No. 10/808,884, Mail Date Jun. 16, 2010.
Office Action dated Apr. 30, 2009 from U.S. Appl. No. 11/877,891, which is a divisional of U.S. Appl. No. 10/808,884.
Office Action dated Oct. 29, 2009 from U.S. Appl. No. 11/877,891, which is a divisional of U.S. Appl. No. 10/808,884.
Office Action dated Sep. 18, 2009 from U.S. Appl. No. 11/876,793.
Office Action dated Feb. 4, 2010 from U.S. Appl. No. 11/876,793.
Invitation to Pay Additional Fees and, Where Applicable, Protest Fee (Form PCT/ISA/206) for PCT/IB2009/007451 dated Apr. 7, 2010, which corresponds to U.S. Appl. No. 12/269,072.
Form PCT/ISA/220, Form PCT/ISA/210, and Form PCT/ISA/237 for PCT/IB2009/007449 dated Feb. 10, 2010, which corresponds to U.S. Appl. No. 12/570,923.
Form PCT/ISA/220, Form PCT/ISA/210, and Form PCT/ISA/237 for PCT/IB2009/007456 dated Jan. 25, 2010, which corresponds to U.S. Appl. No. 12/576,622.
CRC Handbook of Chemistry & Physics, "Dissociation Constants of Organic Acids and Bases", CRC Press (1994-1995 75th Edition), pp. 8-45-pp. 8-55.
Ahn et al., "New Antireflective Coating Materials Containing a Novel Chromophore for KrF Laser Lithography", Journal of Photopolymer Science and Technology, vol. 14, No. 3, pp. 475-pp. 480 (2001).
Houlihan et al., "Chemically Amplified Resists: The Chemistry and Lithographic Characteristics of Nitrobenzyl Benzenesulfonate Derivatives", Journal of Photopolymer Science and Technology, vol. 3, No. 3, pp. 259-pp. 273 (1990).
Leonard V. Interrante, Chemistry of Materials, vol. 6, No. 10 (1994).
Lange's Handbook of Chemistry (15th Edition), Table 8.8 pKa Value of Organic Materials in Water at 25 degrees C Records 1426 and 1428, McGraw-Hill, www.knovel.com, 2 pages (1999).
Lee et al., "Performance of vinyl ether cross-linkers on resist for 193 nm lithography", SPIE, vol. 4690, pp. 541-548 (2002).
Jerry March, "Advanced Organic Chemistry: Reactions, Mechanisms, and Structure", Second Edition, McGraw-Hill Book Company, New York, NY, pp. 225-pp. 245 (1977).
Moon of al., Three-Component Photopolymers Based on Thermal Cross-Linking and Acidolytic De-Cross-Linking of Vinyl Ether Groups. Effects of Binder Polymers on Photopolymer Characteristics, *Chemical Materials*, vol. 6, pp. 1854-pp. 1860 (1994).
Moon et al., "Three-component photoresists based on thermal crosslinking and acidolytic cleavage", Polymer 41, pp. 4013-pp. 4019 (2000).
Moon et al., "Three-component Photoresists Containing Thermally Crosslinkable Generators", Polymer Engineering and Science vol. 40, No. 5, pp. 1248-pp. 1255 (May 2000)—XP000969783.
Nakano et al., "Positive-Type Photopolyirnide Based on Vinyl Ether Crosslinking and De-Crosslinking", Journal of Photopolymer Science and Technology vol. 13, No. 5, pp. 715-pp. 718 (2000).
Noppakundilograt et al., "Visible Light-Sensitive Positive-Working Photopolymer Based on Poly(*p*-hydroxystyrene) and Vinyl Ether Crosslinker", Journal of Photopolymer Science and Technology vol. 13, No. 5, pp. 719-pp. 722 (2000).
Papadopoulos et al., "Dissociation of Salicylic Acid, 2,4-, 2,5-, and 2,6- Dihydroxybenzoic Acids in 1-Propanol—Water Mixtures at 25° C.", Journal of Solution Chemistry, vol. 20, No. 3, pp. 293-pp. 300 (1991).
Schacht et al., "Acid Labile Cross-Linked Units: A Concept for Improved Positive Deep-UV Photoresists", American Chemical Society, pp. 78-pp. 94 (1998).
Schlegel et al., "Studies on the Acid Formation and Deprotection Reaction by Novel Sulfonates in a Chemical Amplification Positive Photoresist", Journal of Photopolymer & Science Technology, vol. 3, No. 3, pp. 281-pp. 287 (1990).
Shirai et al., "Photochemistry of Imino Sultanate Compounds and Their Application to Chemically Amplified Resists", Journal of Photopolymer Science and Technology, vol. 3, No. 3, pp. 301-pp. 304 (1990).
White et al., "Synthesis and characterization of photodefinable polycarbonates for use as sacrificial materials in the fabrication of microfluidic devices", SPIE vol. 4690, pp. 242-pp. 253 (2002).
Yamada et al., "The design and study of aqueous-processabie positibe tone photoresists", SPIE vol. 3999, pp. 569-pp. 578 (2000).
Yamada et al., "Positive and Negative Tone Water Processable Photoresists: A Progress Report", SPIE vol. 3333, pp. 245-pp. 253 (2000).
Willson Research Group, University of Texas at Austin, "Aqueous Processable Positive and Negative Tone Photoresists", Apr. 18, 2001, available at http://willson.cm.utexas.edu/Research/Sub_Files/Water_Soluble/index.php (last visited May 6, 2010). with cover page.

Yamaoka et al., "Reaction of vinyl ethers and application of photoreactive process", Trends in Photochemistry & Photobiology, vol. 7, pp. 45-pp. 70 (2001).

Yamaoka et al., "Photochemical Dissociation of p-Nitrobenzyl Aromatic Sulfanate and Its Application to Chemical Amplification Resists", *Journal of Photopolyrner Science and Technology*, vol. 3, No. 3, pp. 275-pp. 280 (1990).

English Translation of Office Action dated Jul. 6, 2010 for Chinese Patent Application No. CN 200580011869.5, which corresponds to U.S. Appl. No. 10/808,884.

U.S. Appl. No. 12/270,923, filed Sep. 30, 2009, Padmanaban et al.

U.S. Appl. No. 12/576,622, filed Oct. 9, 2009, Dammel et al.

Form PCT/ISA/220, Form PCT/ISA/210, and Form PCT/ISA/237 for PCT/IB2009/007449 mailed Feb. 10, 2010, which corresponds to U.S. Appl. No. 12/270,923.

Form PCT/ISA/220, Form PCT/ISA/210, and Form PCT/ISA/237 for PCT/IB2009/007456 mailed Jan. 25, 2010, which corresponds to U.S. Appl. No. 12/576,622.

Office Action dated Dec. 1, 2010 from U.S. Appl. No. 11/876,793.

Jerry March, "0-11 Hydroysis of Esters" from Advanced Organic Chemistry: Reactions, Mechanisms, and Structure, Second Edition, McGraw-Hill Book Company, New York, NY, pp. 349-353 (1977).

English Translation of Office Action dated Jul. 24, 2009 for Chinese Patent Application No. CN 200580011869.5, which corresponds to U.S. Appl. No. 10/808,884.

Office Action dated Sep. 7, 2010 for U.S. Appl. No. 11/876,793.

Office Action dated Sep. 22, 2010 from European Patent Office for European Application No. 08 843 074.9, which corresponds to U.S. Appl. No. 11/876,793.

English Translation of Office Action mailed Oct. 12, 2010 for Japanese Patent Application No. 2007-504508, which corresponds to U.S. Appl. No. 10/808,884.

Complete set of specification papers for U.S. Appl. No. 12/570,923, filed Sep. 30, 2009 with cover page.

Complete set of specification papers for U.S. Appl. No. 12/576,622, filed Oct. 9, 2009 with cover page.

Office Action mail date Feb. 1, 2011 for U.S. Appl. No. 11/877,891.

Abstract and English translation of JP 2005-070154-a printed out Dec. 23, 2010.

Notification of the Third Office Action dated Jan. 31, 2012 for Chinese Patent Application No. CN 200580011869.5, which corresponds to U.S. Appl. No. 10/808,884.

Engl. Lang. Transl. of Notification of the Third Office Action dated Jan. 31, 2012 for Chinese Patent Application No. CN 200580011869. 5, which corresponds to U.S. Appl. No. 10/808,884.

Office Action dated Feb. 17, 2012 for U.S. Appl. No. 12/570,923.

Office Action mail date Jan. 23, 2012 for U.S. Appl. No. 12/576,622.

Form PCT/IB/326, Form PCT/IB/373, and Form PCT/ISA/237 for PCT/IB/2009/007451 dated May 26, 2011, which corresponds to U.S. Appl. No. 12/269,072.

Office Action mail date Mar. 20, 2012 for U.S. Appl. No. 12/576,622.

Office Action mail date May 15, 2012 for U.S. Appl. No. 12/570,923.

Form PCT/IB/326, Form PCT/IB/373, and Form PCT/ISA/237 dated Apr. 19, 2012 for PCT/IB/2009/007456, which corresponds to U.S. Appl. No. 12/576,622.

Third Office Action dated Jul. 14, 2011 for Chinese Patent Application No. CN 200580011869.5, which corresponds to U.S. Appl. No. 10/808,884.

English Translation of Third Office Action dated Jul. 14, 2011 for Chinese Patent Application No. CN 200580011869.5, which corresponds to U.S. Appl. No. 10/808,884.

Notice of Allowance and Fee(s) Due date mailed Sep. 7, 2011 for U.S. Appl. No. 11/876,793.

Eng. Trans. of Official Action mailed Sep. 13, 2011 from the JPO for Japanese Patent Application No. 2007-504508, which corresponds to U.S. Appl. No. 10/808,884.

Official Action received Aug. 17, 2011 from the KIPO for Korean Patent Application No. 10-2006-7022194, which corresponds to U.S. Appl. No. 10/808,884.

Eng. Trans. of Official Action received Aug. 17, 2011 from the KIPO for Korean Patent Application No. 10-2006-7022194, which corresponds to U.S. Appl. No. 10/808,884.

Office Action with Search Report from the Taiwan IPO received Sep. 13, 2011 for Taiwan Patent Application No. 094106806, which corresponds to U.S. Appl. No. 10/808,884.

Eng. Trans. of Office Action with Search Report from the Taiwan IPO received Sep. 13, 2011 for Taiwan Patent Application No. 094106806, which corresponds to U.S. Appl. No. 10/808,884.

Final Office Action dated Sep. 14, 2012 for U.S. Appl. No. 12/570,923.

Office Action mail date Sep. 20, 2012 for U.S. Appl. No. 12/576,622.

English Language Abstract of JP 2009-107996 A from Derwent, Printed out Jan. 18, 2012.

English Language Translation of JP 2009-107996 A from JPO, printed out Sep. 17, 2012.

Office Action dated Jun. 19, 2012 for Korean Patent Application No. 10-2011-7027434, which corresponds to U.S. Appl. No. 11/876,332.

Eng. Lang. Transl. of Office Action dated Jun. 19, 2012 for Korean Patent Application No. 10-2011-7027434, which corresponds to U.S. Appl. No. 11/876,332.

Notification of the First Office Action from the Chinese Patent Office for CN200980161200.2 dated Dec. 4, 2012, which corresponds to U.S. Appl. No. 12/570,923.

English Language Translation of Notification of the First Office Action from the Chinese Patent Office for CN 200980161200.2 dated Dec. 4, 2012, which corresponds to U.S. Appl. No. 12/570,923.

Notification of the First Office Action from the Chinese Patent Office dated Dec. 4, 2012 for CN 200980161858.3, which corresponds to U.S. Appl. No. 12/576,622.

English Language Translation of Notification of the First Office Action from the Chinese Patent Office dated Dec. 4, 2012 for CN 200980161858.3, which corresponds to U.S. Appl. No. 12/576,622.

\* cited by examiner

COATING COMPOSITION

FIELD OF THE INVENTION

The present invention relates to aqueous developable coating compositions useful as coating layers in multilayer systems and new compounds for use therein.

BACKGROUND

In several industries (for example, the varnish, printing ink, paint, and lithography markets), multilayer systems are used in connection with a variety of substrates. In some instances, these systems contain acid-curable resins. Acid-curable resin compositions contain at least one component capable of acid-catalyzed polycondensation. These materials are familiar to those skilled in the art; they are produced industrially in large quantities with modifications to their material properties as appropriate for a great number of applications. In some instances, the materials cross-link to form coating layers. Acid-curable resin compositions can contain, for example, alkyd resins, melamine resins, urea resins, guanamine resins, phenolic resins, polyester resins, (meth)acrylic resins, polyvinyl resins, vinyl ethers, vinyl esters, styrene/substituted styrene resins, polyimide resins, epoxide resins, urethane resins, and mixtures thereof. Examples of mixtures include, but are not limited to, melamine/(meth)acrylic resins, melamine/polyester resins, melamine/alkyd resins, vinyl ether/(meth)acrylic resins, vinyl ether/substituted styrene resins, and the like. One example where multilayer systems are used is the microlithography or photolithography industry.

Photoresist compositions are used in microlithography processes for making miniaturized electronic components such as in the fabrication of computer chips and integrated circuits. Generally, in these processes, a thin coating of a film of a photoresist composition is first applied to a substrate material, such as silicon wafers used for making integrated circuits. The coated substrate is then baked to evaporate any solvent in the photoresist composition and to fix the coating onto the substrate. The baked and coated surface of the substrate is next subjected to an image-wise exposure to radiation. The radiation exposure causes a chemical transformation in the exposed areas of the coated surface. Visible light, ultraviolet (UV) light, electron beam and X-ray radiant energy are radiation types commonly used today in microlithographic processes. After this image-wise exposure, the coated substrate is treated with a developer solution to dissolve and remove either the radiation-exposed or the unexposed areas of the photoresist.

There are two types of photoresist compositions, negative-working and positive-working. When positive-working photoresist compositions are exposed image-wise to radiation, the areas of the photoresist composition exposed to the radiation become soluble in a developer solution while the unexposed areas of the photoresist coating remain relatively insoluble to such a solution. Thus, treatment of an exposed positive-working photoresist with a developer causes removal of the exposed areas of the photoresist coating and the formation of a positive image in the coating, thereby uncovering a desired portion of the underlying substrate surface on which the photoresist composition was deposited. In a negative-working photoresist the developer removes the portions that are not exposed.

The trend towards the miniaturization of semiconductor devices has led both to the use of new photoresists that are sensitive to lower and lower wavelengths of radiation, and also to the use of sophisticated multilevel systems to overcome difficulties associated with such miniaturization.

In these multilevel or multilayer systems, for example, the use of highly absorbing antireflective coatings in photolithography is a simpler approach to diminish the problems that result from back reflection of light from highly reflective substrates. A developable bottom antireflective coating is applied on the substrate and then a layer of photoresist is applied on top of the antireflective coating. The photoresist is exposed imagewise and developed. The developable bottom antireflective coating is also developable with the same aqueous alkaline developing solution as that used to typically develop the photoresist. Additionally, barrier coatings or top antireflective coatings or immersion protection coatings are also used in multilayer systems.

Often times, the formulations used in the coatings industries, are baked at temperatures above room temperature. The baking temperatures can vary, depending upon the type of coating applied and its desired use. In some instances, having a coating which contains a thermal acid generator with a low decomposition temperature, which in turn relates to a low baking temperature, is beneficial.

SUMMARY OF THE INVENTION

The present invention relates to an antireflective coating composition comprising a polymer having a dye or chromophore moiety and crosslinking functionality, an optional crosslinking component, and one or more photoactive compounds having the formula $$W\text{-}(L\text{-}(G))_p \qquad (I)$$

where W is PAG or Q, where PAG is a photoacid generator and Q is a quencher; each L is a direct bond or a linking group; each G is independently G1 or G2; G1 is OH; G2 is $OCH=CH_2$; p is 1 to 12. Some embodiments include those where p is from 2 to 6 as well as when there is a mixture of G1 and G2 on the same compound; for example $(G1\text{-}L)_{p1}\text{-}W\text{-}(L\text{-}G2)_{p2}$ where p1 and p2 are each greater than or equal to 1 and p1+p2 equal 2 to 12.

The present invention relates to a positive bottom photoimageable antireflective coating composition which is capable of being developed with an aqueous alkali developer and which is coated below a positive photoresist, wherein the antireflective coating composition comprises a polymer and one or more compounds having the formula $$W\text{-}(L\text{-}(G))_p \qquad (I)$$

where W is PAG or Q, where PAG is a photoacid generator and Q is a quencher; each L is a direct bond or a linking group; each G is independently G1 or G2; G1 is OH; G2 is $OCH=CH_2$; p is 1 to 12. Some embodiments include those where p is from 2 to 6 as well as when there is a mixture of G1 and G2 on the same compound; for example $(G1\text{-}L)_{p1}\text{-}W\text{-}(L\text{-}G2)_{p2}$ where p1 and p2 are each greater than or equal to 1 and p1+p2 equal 2 to 12.

The invention also relates to a first coating composition used in conjunction with at least one other coating composition wherein the first coating composition comprises a polymer and one or more photoactive compounds having the formula $$W\text{-}(L\text{-}(G))_p$$

where W is PAG or Q, where PAG is a photoacid generator and Q is a quencher; each L is a direct bond or a linking group; each G is independently G1 or G2; G1 is OH; G2 is $OCH=CH_2$; p is 1 to 12.

The present invention also relates to a positive bottom photoimageable antireflective coating composition which is capable of being developed with an aqueous alkali developer and which is coated below a positive photoresist, wherein the antireflective coating composition consists of (a) either (a1) a mixture of at least one compound of formula (1) and at least one compound of formula (2)

$$\text{PAG-(-L-OH)}_p \tag{1}$$

$$\text{PAG-(-L-OCH=CH}_2)_p \tag{2}$$

or
(a2) at least one compound of formula (5)

$$\text{(HO-L)}_{p1}\text{-PAG-(-L-OCH=CH}_2)_{p2} \tag{5}$$

and
(b) a solvent,
where PAG is a photoacid generator, each L is a direct bond or a linking group; p is an integer 1 to 12; p1 and p2 are each greater than or equal to 1 and p1+p2 equal 2 to 12, wherein at least one PAG contains a chromophore moiety. The composition can further comprise a compound selected from $$\text{Q-(-L-OH)}_p \tag{3}$$

$$\text{Q-(-L-OCH=CH}_2)_p \tag{4}$$

$$\text{(HO-L)}_{p3}\text{-Q-(-L-OCH=CH}_2)_{p4} \tag{6}$$

and mixtures thereof, where Q is a quencher, each L is a direct bond or a linking group; p is an integer 1 to 12; p3 and p4 are each greater than or equal to 1 and p3+p4 equal 2 to 12. Further, the composition can also comprise a thermal acid generator.

The invention also relates to a compound selected from the group $$\text{PAG-(-L-OCH=CH}_2)_p$$

$$\text{Q-(-L-OCH=CH}_2)_p$$

$$\text{(HO-L)}_{p1}\text{-PAG-(-L-OCH=CH}_2)_{p2}$$

$$\text{(HO-L)}_{p1}\text{-Q-(-L-OCH=CH}_2)_{p2}$$

where PAG is a photoacid generator, Q is a quencher, where each L is a direct bond or a linking group; p is 1 to 12; p1 and p2 are each greater than or equal to 1 and p1+p2 equal 2 to 12, with the proviso that bis{4-[2-(vinyloxy)ethoxy]benzene}-3,5-dimethyl-4-[2-(vinyloxy)ethoxy]benzene sulfonium tosylate, bis{4-[2-(vinyloxy)ethoxy]benzene}-3,5-dimethyl-4-methoxybenzene sulfonium triflate, bis{4-[2-(vinyloxy)ethoxy]benzene}-3,5-dimethyl-4-methoxybenzene sulfonium perfluoro-1-butanesulfonate, tris{4-[2-(vinyloxy)ethoxy]benzene}sulfonium 10-camphorsulfonate, and tris{4-[2-(vinyloxy)ethoxy]benzene}sulfonium cyclohexane sulfamate are excluded.

The invention also relates to a coated substrate where a layer of an inventive coating composition is coated on top of or underneath of another coating layer or, in some instances a layer of an inventive coating composition is between two other layers.

The invention also relates to a process for forming an image comprising: a) forming a coating of the antireflective coating composition of the present invention on a substrate; b) baking the antireflective coating, c) providing a coating of a top photoresist layer over the antireflective coating; d) developing an image using an aqueous alkaline developer; e) optionally heating the substrate prior to and after development and, f) dry etching the antireflective coating.

The invention also relates to a process for forming an image comprising: a) forming a coating of the bottom photoimageable antireflective coating composition of the present invention on a substrate; b) baking the antireflective coating, c) providing a coating of a top photoresist layer over the antireflective coating; d) imagewise exposing the photoresist and antireflective coating layers to actinic radiation of same wavelength; e) post-exposure baking the photoresist and antireflective coating layers on the substrate; and, f) developing the photoresist and antireflective coating layers with an aqueous alkaline solution.

DETAILED DESCRIPTION OF THE INVENTION

The present invention relates to an antireflective coating composition comprising a polymer having a dye or chromophore moiety and crosslinking functionality, an optional crosslinking component, and one or more photoactive compounds having the formula $$\text{W-(L-(G))}_p \tag{I}$$

where W is PAG or Q, where PAG is a photoacid generator and Q is a quencher; each L is a direct bond or a linking group; each G is independently G1 or G2; G1 is OH; G2 is OCH=CH$_2$; p is 1 to 12. Some embodiments include those where p is from 2 to 6 as well as when there is a mixture of G1 and G2 on the same compound; for example (G1-L)$_{p1}$-W-(L-G2)$_{p2}$ where p1 and p2 are each greater than or equal to 1 and p1+p2 equal 2 to 12.

The present invention relates to a positive bottom photoimageable antireflective coating composition which is capable of being developed with an aqueous alkali developer and which is coated below a positive photoresist, wherein the antireflective coating composition comprises a polymer and one or more compounds having the formula $$\text{W-(L-(G))}_p \tag{I}$$

where W is PAG or Q, where PAG is a photoacid generator and Q is a quencher; each L is a direct bond or a linking group; each G is independently G1 or G2; G1 is OH; G2 is OCH=CH$_2$; p is 1 to 12. Some embodiments include those where p is from 2 to 6 as well as when there is a mixture of G1 and G2 on the same compound; for example (G1-L)$_{p1}$-W-(L-G2)$_{p2}$ where p1 and p2 are each greater than or equal to 1 and p1+p2 equal 2 to 12.

The invention also relates to a first coating composition used in conjunction with at least one other coating composition wherein the first coating composition comprises a polymer and one or more photoactive compounds having the formula $$\text{W-(L-(G))}_p$$

where W is PAG or Q, where PAG is a photoacid generator and Q is a quencher; each L is a direct bond or a linking group; each G is independently G1 or G2; G1 is OH; G2 is OCH=CH$_2$; p is 1 to 12.

The present invention also relates to a positive bottom photoimageable antireflective coating composition which is capable of being developed with an aqueous alkali developer and which is coated below a positive photoresist, wherein the antireflective coating composition consists of (a) either (a1) a mixture of at least one compound of formula (1) and at least one compound of formula (2)

$$\text{PAG-(-L-OH)}_p \tag{1}$$

$$\text{PAG-(-L-OCH=CH}_2)_p \tag{2}$$

or
(a2) at least one compound of formula (5)

$$(HO-L)_{p1}\text{-PAG-}(-L\text{-OCH}=CH_2)_{p2} \quad (5)$$

and
(b) a solvent,
where PAG is a photoacid generator, each L is a direct bond or a linking group; p is an integer 1 to 12; p1 and p2 are each greater than or equal to 1 and p1+p2 equal 2 to 12, wherein at least one PAG contains a chromophore moiety. The composition can further comprise a compound selected from $$Q\text{-}(-L\text{-OH})_p \quad (3)$$

$$Q\text{-}(-L\text{-OCH}=CH_2)_p \quad (4)$$

$$(HO-L)_{p3}\text{-Q-}(-L\text{-OCH}=CH_2)_{p4} \quad (6)$$

and mixtures thereof, where Q is a quencher, each L is a direct bond or a linking group; p is an integer 1 to 12; p3 and p4 are each greater than or equal to 1 and p3+p4 equal 2 to 12. Further, the composition can also comprise a thermal acid generator.

The invention also relates to a compound selected from the group $$\text{PAG-}(-L\text{-OCH}=CH_2)_p$$

$$Q\text{-}(-L\text{-OCH}=CH_2)_p$$

$$(HO-L)_{p1}\text{-PAG-}(-L\text{-OCH}=CH_2)_{p2}$$

$$(HO-L)_{p1}\text{-Q-}(-L\text{-OCH}=CH_2)_{p2}$$

where PAG is a photoacid generator, Q is a quencher, where each L is a direct bond or a linking group; p is 1 to 12; p1 and p2 are each greater than or equal to 1 and p1+p2 equal 2 to 12, with the proviso that bis{4-[2-(vinyloxy)ethoxy]benzene}-3,5-dimethyl-4-[2-(vinyloxy)ethoxy]benzene sulfonium tosylate, bis{4-[2-(vinyloxy)ethoxy]benzene}-3,5-dimethyl-4-methoxybenzene sulfonium triflate, bis{4-[2-(vinyloxy)ethoxy]benzene}-3,5-dimethyl-4-methoxybenzene sulfonium perfluoro-1-butanesulfonate, tris{4-[2-(vinyloxy)ethoxy]benzene}sulfonium 10-camphorsulfonate, and tris{4-[2-(vinyloxy)ethoxy]benzene}sulfonium cyclohexane sulfamate are excluded.

The invention also relates to a coated substrate where a layer of an inventive coating composition is coated on top of or underneath of another coating layer or, in some instances a layer of an inventive coating composition is between two other layers.

The invention also relates to a process for forming an image comprising: a) forming a coating of the antireflective coating composition of the present invention on a substrate; b) baking the antireflective coating, c) providing a coating of a top photoresist layer over the antireflective coating; d) developing an image using an aqueous alkaline developer; e) optionally heating the substrate prior to and after development and, f) dry etching the antireflective coating.

The invention also relates to a process for forming an image comprising: a) forming a coating of the bottom photoimageable antireflective coating composition of the present invention on a substrate; b) baking the antireflective coating, c) providing a coating of a top photoresist layer over the antireflective coating; d) imagewise exposing the photoresist and antireflective coating layers to actinic radiation of same wavelength; e) post-exposure baking the photoresist and antireflective coating layers on the substrate; and, f) developing the photoresist and antireflective coating layers with an aqueous alkaline solution.

PAG refers to photoacid generator and Q refers to quencher, which includes quenchers and photodecomposable quenchers.

The PAGs which are useful herein include, for example,
(i) onium (not including ammonium) salts of the formula (P1a), (P1b), (P1c) (P1d), (P1e), (P1f),
(ii) diazomethane derivatives of the formula (P2),
(iii) glyoxime derivatives of the formula (P3),
(iv) bissulfone derivatives of the formula (P4),
(v) sulfonic acid esters of N-hydroxyimide compounds of the formula (P5),
(vi) β-ketosulfonic acid derivatives,
(vii) disulfone derivatives,
(viii) nitrobenzylsulfonate derivatives,
(ix) sulfonate derivatives,
(x) benzyloxysulfonylbenzene derivatives of the formula (P6)

These acid generators are described in detail.
(i) Onium Salts of Formula (P1a) or (P1b):

wherein Ar is an unsubstituted or substituted aryl group of 6 to 20 carbon atoms; $R_{10b}$ and $R_{10c}$ independently represent unsubstituted or substituted straight, branched or cyclic alkyl, alkenyl, aryl groups of 6 to 20 carbon atoms, aralkyl or aryloxoalkyl groups of 7 to 12 carbon atoms, the straight, branched or cyclic alkyl or alkenyl groups optionally containing one or more O atoms. Also, $R_{10b}$ and $R_{10c}$, taken together, may form a ring. $R_{10b}$ and $R_{10c}$ each are alkylene groups of 1 to 6 carbon atoms when they form a ring. $A^-$ is an anion.

$R_{10b}$ and $R_{10c}$ may be the same or different and are illustrated below. Exemplary and non-limiting alkyl groups include methyl, ethyl, propyl, isopropyl, n-butyl, sec-butyl, tert-butyl, pentyl, hexyl, heptyl, octyl, cyclopentyl, cyclohexyl, cycloheptyl, cyclopropylmethyl, 4-methylcyclohexyl, cyclohexylmethyl, norbornyl, and adamantyl. Exemplary and non-limiting alkenyl groups include vinyl, allyl, propenyl, butenyl, hexenyl, and cyclohexenyl. Exemplary and non-limiting aryl groups include phenyl, naphthyl, and anthryl; alkoxyphenyl groups such as p-methoxyphenyl, m-methoxyphenyl, o-methoxyphenyl, ethoxyphenyl, p-tert-butoxyphenyl, and m-tert-butoxyphenyl; alkylphenyl groups such as 2-methylphenyl, 3-methylphenyl, 4-methylphenyl, ethylphenyl, 4-tert-butylphenyl, 4-butylphenyl, and dimethylphenyl; alkylnaphthyl groups such as methylnaphthyl and ethylnaphthyl; alkoxynaphthyl groups such as methoxynaphthyl and ethoxynaphthyl; dialkylnaphthyl groups such as dimethylnaphthyl and diethylnaphthyl; and dialkoxynaphthyl groups such as dimethoxynaphthyl and diethoxynaphthyl. Exemplary and non-limiting aralkyl groups include benzyl, phenylethyl, and phenethyl. Exemplary and non-limiting aryloxoalkyl groups are 2-aryl-2-oxoethyl groups such as 2-phenyl-2-oxoethyl, 2-(1-naphthyl)-2-oxoethyl, and 2-(2-naphthyl)-2-oxoethyl. Non-limiting examples of anion represented by $A^-$ include fluoroalkylsulfonate ions such as triflate, 1,1,1-trifluoroethanesulfonate, and nonafluorobutanesulfonate, arylsulfonate ions such as tosylate, benzenesulfonate, 4-fluorobenzenesulfonate, and 1,2,3, 4,5-pentafluorobenzenesulfonate, alkylsulfonate ions such as mesylate and butanesulfonate, $(Rf1SO_2)_3C^-$ and $(Rf1SO_2)_2N^-$, wherein each Rf1 is independently selected from the group consisting of highly fluorinated or perfluorinated alkyl or fluorinated aryl radicals and may be cyclic, when a combination of any two Rf1 groups are linked to form a bridge, further, the Rf1 alkyl chains contain from 1-20 carbon atoms and may be straight, branched, or cyclic, such that oxygen, trivalent nitrogen or hexavalent sulfur may interrupt the skeletal chain, further when Rf1 contains a cyclic structure, such structure has 5 or 6 ring members, optionally, 1 or 2 of which are heteroatoms, and $Rg\text{-}O\text{-}Rf2\text{-}SO_3^-$, where Rf2 is selected from the group consisting of linear or branched $(CF_2)_j$ where j is an integer from 4 to 10 and $C_1\text{-}C_{12}$ cycloperfluoroalkyl radical which is optionally perfluoro$C_{1-10}$alkyl substituted, Rg is selected from the group consisting of $C_1\text{-}C_{20}$ linear, branched, monocycloalkyl or polycycloalkyl, $C_1\text{-}C_{20}$ linear, branched, monocycloalkenyl or polycycloalkenyl, aryl, and aralkyl, the alkyl, alkenyl, aralkyl and aryl groups being unsubstituted, substituted, optionally containing one or more catenary heteroatoms, partially fluorinated or perfluorinated. Examples of such anions Xi2 include $(C_2F_5SO_2)_2N^-$, $(C_4F_9SO_2)_2N^-$, $(C_8F_{17}SO_2)_3C^-$, $(CF_3SO_2)_3C^-$, $(CF_3SO_2)_2N^-$, $(CF_3SO_2)_2(C_4F_9SO_2)C^-$, $(C_2F_5SO_2)_3C^-$, $(C_4F_9SO_2)_3C^-$, $(CF_3SO_2)_2(C_2F_5SO_2)C^-$, $(C_4F_9SO_2)(C_2F_5SO_2)_2C^-$, $(CF_3SO_2)(C_4F_9SO_2)N^-$, $[(CF_3)_2NC_2F_4SO_2]_2 N^-$, $(CF_3)_2NC_2F_4SO_2C^-(SO_2CF_3)_2$, $(3,5\text{-bis}(CF_3)C_6H_3)SO_2N^-SO_2CF_3$, $C_6F_5SO_2C^-(SO_2CF_3)_2$, $C_6F_5SO_2N^-SO_2CF_3$,

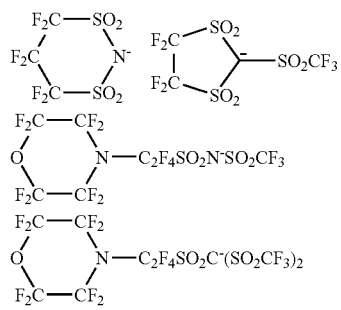

$CF_3CHFO(CF_2)_4SO_3^-$, $CF_3CH_2O(CF_2)_4SO_3^-$, $CH_3CH_2O(CF_2)_4SO_3^-$, $CH_3CH_2CH_2O(CF_2)_4SO_3^-$, $CH_3O(CF_2)_4SO_3^-$, $C_2H_5O(CF_2)_4SO_3^-$, $C_4H_9O(CF_2)_4SO_3^-$, $C_6H_5CH_2O(CF_2)_4SO_3^-$, $C_2H_5OCF_2CF(CF_3)SO_3^-$, $CH_2=CHCH_2O(CF_2)_4SO_3^-$, $CH_3OCF_2CF(CF_3)SO_3^-$, $C_4H_9OCF_2CF(CF_3)SO_3^-$, $C_8H_{17}O(CF_2)_2SO_3^-$, and $C_4H_9O(CF_2)_2SO_3^-$.

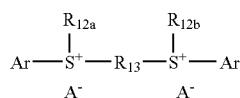
(P1c)

Herein, Ar is as defined above, $R_{12a}$ and $R_{12b}$ independently stand for the same as $R_{10b}$. $R_{13}$ represents a straight, branched or cyclic alkylene group of 1 to 10 carbon atoms optionally containing one or more O atoms. $A^-$ is an anion as described above. Illustrative of the groups represented by $R_{13}$ are methylene, ethylene, propylene, butylene, pentylene, hexylene, heptylene, octylene, nonylene, 1,4-cyclohexylene, 1,2-cyclohexylene, 1,3-cyclopentylene, 1,4-cyclooctylene, and 1,4-cyclohexanedimethylene.

(P1d)

(P1e)

(P1f)

Wherein Ar is as defined above, $R_{10b}$ and $R_{10c}$ are independently defined as above and $X^{-2}$ is a $Q\text{-}R_{500}\text{—}SO_3^-$, where Q is selected from $^-O_3S$, $^-O_2C$, or $^-J$; $R_{500}$ is a group selected from linear or branched alkyl, cycloalkyl, aryl, or combinations thereof, optionally containing a catenary heteroatom, where the alkyl, cycloalkyl, and aryl groups are unsubstituted or substituted by one or more groups selected from the group consisting of halogen, unsubstituted or substituted alkyl, unsubstituted or substituted $C_{1-8}$ perfluoroalkyl, hydroxyl, cyano, sulfate, and nitro; and J is fluoride, chloride, bromide or iodide.

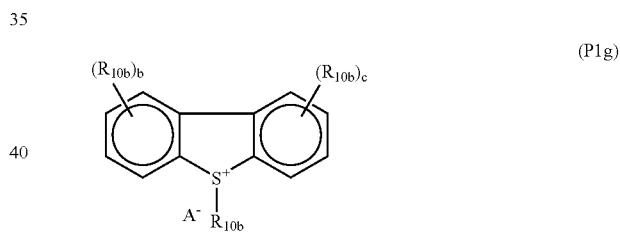
(P1g)

Wherein each $R_{10b}$ is independently defined as above or hydrogen; b and c are independently 0 to 4; and $A^-$ is an anion as described above.

(ii) Diazomethane Derivatives of Formula (P2)

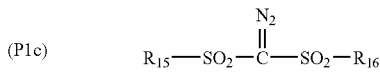
(P2)

Herein, $R_{15}$ and $R_{16}$ independently represent unsubstituted or substituted straight, branched or cyclic alkyl optionally containing one or more O atoms, or halogenated alkyl groups of 1 to 12 carbon atoms, unsubstituted or substituted aryl or halogenated aryl groups of 6 to 20 carbon atoms, or unsubstituted or substituted aralkyl groups of 7 to 12 carbon atoms.

Of the groups represented by $R_{15}$ and $R_{16}$, exemplary alkyl groups include methyl, ethyl, propyl, isopropyl, n-butyl, sec-butyl, tert-butyl, pentyl, hexyl, heptyl, octyl, amyl, cyclopentyl, cyclohexyl, cycloheptyl, norbornyl, and adamantyl. Exemplary halogenated alkyl groups include trifluoromethyl, 1,1,1-trifluoroethyl, 1,1,1-trichloroethyl, and nonafluorobutyl. Exemplary aryl groups include phenyl; alkoxyphenyl groups such as p-methoxyphenyl, m-methoxyphenyl, o-methoxyphenyl, ethoxyphenyl, p-tert-butoxyphenyl, and m-tert-butoxyphenyl; and alkylphenyl groups such as 2-methylphenyl, 3-methylphenyl, 4-methylphenyl, ethylphenyl, 4-tert-butylphenyl, 4-butylphenyl, and dimethylphenyl. Exemplary halogenated aryl groups include fluorophenyl, chlorophenyl, and 1,2,3,4,5-pentafluorophenyl. Exemplary aralkyl groups include benzyl and phenethyl.

(iii) Glyoxime Derivatives of Formula (P3)

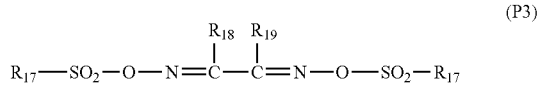

(P3)

Herein, $R_{17}$, $R_{18}$, and $R_{19}$ independently represent unsubstituted or substituted straight, branched or cyclic alkyl or halogenated alkyl groups of 1 to 12 carbon atoms, unsubstituted or substituted aryl or halogenated aryl groups of 6 to 20 carbon atoms, or unsubstituted or substituted aralkyl groups of 7 to 12 carbon atoms. Also, $R_{18}$ and $R_{19}$, taken together, may form a ring. $R_{18}$ and $R_{19}$ each are unsubstituted or substituted straight or branched alkylene groups of 1 to 6 carbon atoms when they form a ring.

Illustrative examples of the alkyl, halogenated alkyl, aryl, halogenated aryl, and aralkyl groups represented by $R_{17}$, $R_{18}$, and $R_{19}$ are the same as exemplified for $R_{15}$ and $R_{16}$. Examples of the alkylene groups represented by $R_{18}$ and $R_{19}$ include methylene, ethylene, propylene, butylene, and hexylene.

(iv) Bissulfone Derivatives of Formula (P4)

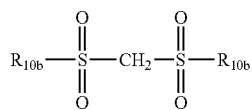

(P4)

Herein, $R_{10b}$ is as defined above.

(v) Sulfonic Acid Esters of N-hydroxyimide Compounds of Formula (P5)

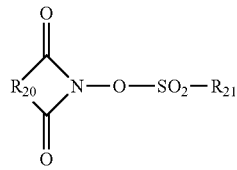

(P5)

Herein, $R_{20}$ is an arylene group of 6 to 10 carbon atoms, alkylene group of 1 to 6 carbon atoms, or alkenylene group of 2 to 6 carbon atoms wherein some or all of the hydrogen atoms may be replaced by straight or branched alkyl or alkoxy groups of 1 to 4 carbon atoms, nitro, acetyl, or phenyl groups. $R_{21}$ is a straight, branched or cyclic alkyl group of 1 to 8 carbon atoms, alkenyl, alkoxyalkyl, phenyl or naphthyl group wherein some or all of the hydrogen atoms may be replaced by alkyl or alkoxy groups of 1 to 4 carbon atoms, phenyl groups (which may have substituted thereon an alkyl or alkoxy of 1 to 4 carbon atoms, nitro, or acetyl group), hetero-aromatic groups of 3 to 5 carbon atoms, or chlorine or fluorine atoms.

Of the groups represented by $R_{20}$, exemplary arylene groups include 1,2-phenylene and 1,8-naphthylene; exemplary alkylene groups include methylene, ethylene, trimethylene, tetramethylene, phenylethylene, and norbornane-2,3-diyl; and exemplary alkenylene groups include 1,2-vinylene, 1-phenyl-1,2-vinylene, and 5-norbornene-2,3-diyl. Of the groups represented by $R_{21}$, exemplary alkyl groups are as exemplified for $R_{10b}$ to $R_{10c}$; exemplary alkenyl groups include vinyl, 1-propenyl, allyl, 1-butenyl, 3-butenyl, isoprenyl, 1-pentenyl, 3-pentenyl, 4-pentenyl, dimethylallyl, 1-hexenyl, 3-hexenyl, 5-hexenyl, 1-heptenyl, 3-heptenyl, 6-heptenyl, and 7-octenyl; and exemplary alkoxyalkyl groups include methoxymethyl, ethoxymethyl, propoxymethyl, butoxymethyl, pentyloxymethyl, hexyloxymethyl, heptyloxymethyl, methoxyethyl, ethoxyethyl, propoxyethyl, butoxyethyl, pentyloxyethyl, hexyloxyethyl, methoxypropyl, ethoxypropyl, propoxypropyl, butoxypropyl, methoxybutyl, ethoxybutyl, propoxybutyl, methoxypentyl, ethoxypentyl, methoxyhexyl, and methoxyheptyl.

Of the substituents on these groups, the alkyl groups of 1 to 4 carbon atoms include methyl, ethyl, propyl, isopropyl, n-butyl, isobutyl and tert-butyl; the alkoxy groups of 1 to 4 carbon atoms include methoxy, ethoxy, propoxy, isopropoxy, n-butoxy, isobutoxy, and tert-butoxy; the phenyl groups which may have substituted thereon an alkyl or alkoxy of 1 to 4 carbon atoms, nitro, or acetyl group include phenyl, tolyl, p-tert-butoxyphenyl, p-acetylphenyl and p-nitrophenyl; the hetero-aromatic groups of 3 to 5 carbon atoms include pyridyl and furyl.

(x) Benzyloxysulfonylbenzene Derivatives of the Formula (P6)

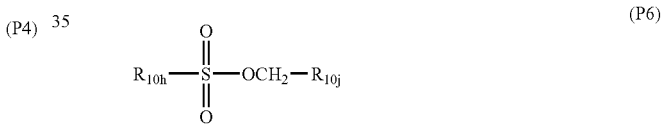

(P6)

Wherein $R_{10h}$ and $R_{10j}$ independently stand for the same as $R_{10b}$.

Illustrative and non-limiting examples of the acid generator include:

onium salts such as diphenyliodonium trifluoromethanesulfonate, (p-tert-butoxyphenyl)phenyliodonium trifluoromethanesulfonate, diphenyliodonium p-toluenesulfonate, (p-tert-butoxyphenyl)phenyliodonium p-toluenesulfonate, triphenylsulfonium trifluoromethanesulfonate, (p-tert-butoxyphenyl)diphenylsulfonium trifluoromethanesulfonate, bis(p-tert-butoxyphenyl)phenylsulfonium trifluoromethanesulfonate, tris(p-tert-butoxyphenyl)sulfonium trifluoromethanesulfonate, triphenylsulfonium p-toluenesulfonate, (p-tert-butoxyphenyl)diphenylsulfonium p-toluenesulfonate, bis(p-tert-butoxyphenyl)phenylsulfonium p-toluenesulfonate, tris(p-tert-butoxyphenyl)sulfonium p-toluenesulfonate, triphenylsulfonium nonafluorobutanesulfonate, triphenylsulfonium butanesulfonate, trimethylsulfonium trifluoromethanesulfonate, trimethylsulfonium p-toluenesulfonate, cyclohexylmethyl(2-oxocyclohexyl)sulfonium trifluoromethanesulfonate, cyclohexylmethyl(2-oxocyclohexyl)sulfonium p-toluenesulfonate, dimethylphenylsulfonium trifluoromethanesulfonate, dimethylphenylsulfonium p-toluenesulfonate, dicyclohexylphenylsulfonium trifluoromethanesulfonate, dicyclohexylphenylsulfonium p-toluenesulfonate, trinaphthylsulfonium trifluoromethanesulfonate, cyclohexylmethyl(2-oxocyclohexyl)sulfonium trifluoromethanesulfonate, (2-norbornyl)methyl(2-oxocyclohexyl)sulfonium trifluoromethanesulfonate, ethylenebis[methyl(2-oxocyclopentyl)sulfonium trifluoromethanesulfonate], 1,2'-naphthylcarbonylmethyltetrahydrothiophenium triflate, bis[4-acetyloxyphenyl]phenylsulfonium perfluorobutanesulfonate, bis[4-acetyloxyphenyl]phenyl sulfonium 4-(1,1,1,2-tetrafluoroethoxy)perfluorobutanesulfonate, bis[2-methyladamantyl-acetyloxymethoxyphenyl]phenylsulfonium perfluoro-butanesulfonate, bis[4,4-bis(trifluoromethyl)-3-oxatricyclo[4.2.1.0$^{2,5}$]nonyl-methoxyphenyl]phenyl sulfonium perfluorobutanesulfonate, bis[4,4-bis(trifluoromethyl)-3-oxatricyclo[4.2.1.0$^{2,5}$]-nonylmethoxyphenyl]phenyl sulfonium perfluoromethanesulfonate, bis[4,4-bis(trifluoromethyl)-3-oxatricyclo[4.2.1.0$^{2,5}$-nonylmethoxyphenyl]phenyl sulfonium 4-(1,1,1,2-tetrafluoroethoxy)perfluoro-butanesulfonate, bis[4,4-bis(trifluoromethyl)-3-oxatricyclo[4.2.1.0$^{2,5}$]nonyl-methoxyphenyl]phenyl sulfonium bis(trifluoromethy-lsulfonyl)imide, bis[4,4-bis(trifluoromethyl)-3-oxatricyclo-[4.2.1.0$^{2,5}$]-nonylmethoxyphenyl]phenyl sulfonium bis(perfluoroethylsulfonyl)imide, bis[4,4-bis(trifluoromethyl)-3-oxatricyclo[4.2.1.0$^{2,5}$]-nonylmethoxyphenyl]phenyl sulfonium (perfluoromethyl-sulfonyl)(perfluorobutylsulfonyl)imide, bis[4,4-bis(trifluoromethyl)-3-oxatricyclo[4.2.1.0$^{2,5}$]-nonylmethoxyphenyl]phenyl sulfonium bis(perfluoropropyl-sulfonyl)imide, bis[4,4-bis(trifluoromethyl)-3-oxatricyclo[4.2.1.0$^{2,5}$] nonylmethoxy-phenyl]phenyl sulfonium bis(perfluorobutylsulfonyl)imide, bis[4,4-bis(trifluoromethyl)-3-oxatricyclo-[4.2.1.0$^{2,5}$]-nonylmethoxyphenyl]phenyl sulfonium tris(trifluoromethyl-sulfonyl)methide, bis[4-acetyloxyphenyl]phenylsulfonium perfluoromethanesulfonate, bis[4-acetyloxyphenyl]phenylsulfonium bis(trifluoromethylsulfonyl)imide, bis[4-acetyloxyphenyl]phenylsulfonium bis(perfluoroethylsulfonyl)imide, bis[4-acetyloxyphenyl]phenylsulfonium (perfluoromethylsulfonyl)(perfluorobutylsulfonyl)imide, bis[4-acetyloxyphenyl]phenylsulfonium bis(perfluoropropylsulfonyl)imide, bis[4-acetyloxyphenyl]phenylsulfonium tris(trifluoromethylsulfonyl)methide, bis[4-acetyloxyphenyl]phenylsulfonium 4-propoxypefluorobutanesulfonate, bis[4-acetyloxyphenyl]phenylsulfonium bis(perfluorobutylsulfonyl)imide, bis[2-methyladamantylacetyl-oxymethoxyphenyl]phenylsulfonium4-(1,1,1,2-tetrafluoroethoxy)perfluorobutane-sulfonate, bis[2-methyladamantylacetyl-oxymethoxyphenyl]phenylsulfonium perfluoromethanesulfonate, bis[2-methyladamantylacetyloxymethoxyphenyl]phenylsulfonium bis(trifluoromethylsulfonyl)imide, bis[2-methyladamantylacetyloxy-methoxy-phenyl]phenylsulfonium bis(perfluoroethylsulfonyl)imide, bis[2-methyladamantyl-acetyloxymethoxyphenyl]phenylsulfonium (perfluoromethyl-sulfonyl)(perfluorobutylsulfonyl)imide, bis[2-methyladamantyl-acetyloxymethoxy-phenyl]phenylsulfonium bis(perfluoropropylsulfonyl)imide, bis[2-methyladamantyl-acetyl-oxymethoxyphenyl]phenylsulfonium 4-propoxypefluorobutanesulfonate, bis[2-methyladamantylacetyloxy-methoxyphenyl]phenylsulfonium tris(trifluoromethyl-sulfonyl)methide, bis [2-methyladamantylacetyloxymethoxyphenyl]phenylsulfonium bis(perfluorobutylsulfonyl)imide, bis[4,4-bis(trifluoromethyl)-3-oxatricyclo-[4.2.1.0$^{2,5}$] nonylmethoxyphenyl]phenyl sulfonium 4-propoxypefluorobutane-sulfonate, bis[4-hydroxyphenyl]phenylsulfonium bis(perfluoroethylsulfonyl)imide, bis[4-hydroxyphenyl]phenylsulfonium bis(trifluoromethylsulfonyl)imide, bis[4-hydroxyphenyl]phenylsulfonium (perfluoromethylsulfonyl)(perfluorobutyl-sulfonyl)imide, bis[4-hydroxyphenyl]-phenylsulfonium bis(perfluoropropyl-sulfonyl)imide, bis[4-hydroxyphenyl]-phenylsulfonium bis(perfluorobutyl-sulfonyl)imide, bis[4-hydroxyphenyl]-phenylsulfonium tris(trifluoromethyl-sulfonyl)methide, bis[4-hydroxyphenyl]-phenylsulfonium 4-(1,1,1,2-tetrafluoroethoxy)perfluorobutanesulfonate, bis[4-hydroxyphenyl]-phenylsulfonium 4-propoxypefluorobutanesulfonate, bis[4-hydroxyphenyl]phenylsulfonium perfluorobutanesulfonate, bis[4-hydroxyphenyl]-phenylsulfonium perfluoromethanesulfonate, bis[4-pentafluorobenzenesulfonyloxyphenyl]phenylsulfonium bis(perfluoroethylsulfonyl)imide, bis[4-pentafluorobenzene-sulfonyloxyphenyl]phenylsulfonium bis(trifluoromethyl-sulfonyl)imide, bis[4-pentafluorobenzene-sulfonyloxyphenyl]phenylsulfonium(perfluoromethylsulfonyl)(perfluorobutyl-sulfonyl)imide, bis[4-pentafluoro-benzenesulfonyloxyphenyl]phenylsulfonium bis(perfluoropropylsulfonyl)imide, bis[4-pentafluorobenzenesulfonyloxyphenyl]phenylsulfonium bis(perfluorobutyl-sulfonyl)imide, bis[4-pentafluorobenzenesulfonyl-oxyphenyl]phenylsulfonium tris(trifluoromethylsulfonyl)methide, bis[4-pentafluorobenzene-sulfonyloxyphenyl]phenylsulfonium 4-(1,1,1,2-tetrafluoroethoxy)perfluorobutanesulfonate, bis[4-pentafluorobenzenesulfonyl-oxyphenyl]phenylsulfonium 4-propoxypefluorobutanesulfonate, bis[4-pentafluorobenzene-sulfonyloxyphenyl]phenylsulfonium perfluorobutanesulfonate, bis[4-pentafluorobenzene-sulfonyloxyphenyl]phenylsulfonium perfluoromethane-sulfonate, bis[4-(3,5-di(trifluoromethyl)-benzenesulfonyloxy)phenyl]phenylsulfonium bis(perfluoroethylsulfonyl)imide, bis[4-(3,5-di(trifluoromethyl)benzenesulfonyloxy)-phenyl]phenylsulfonium bis(trifluoromethylsulfonyl)imide, bis[4-(3,5-di(trifluoro-methyl)benzene-sulfonyloxy)phenyl]phenylsulfonium(perfluoromethylsulfonyl)(perfluorobutylsulfonyl)imide, bis[4-(3,5-di(trifluoromethyl)benzenesulfonyl-oxy)phenyl]phenylsulfonium bis(perfluoropropylsulfonyl)imide, bis[4-(3,5-di(trifluoromethyl)benzenesulfonyloxy)phenyl]phenylsulfonium bis(perfluorobutyl-sulfonyl)imide, bis[4-(3,5-di(trifluoromethyl)benzenesulfonyloxy)phenyl]phenylsulfonium tris(trifluoromethylsulfonyl)methide, bis[4-(3,5-di(trifluoro-methyl)benzenesulfonyloxy)phenyl]phenylsulfonium 4-(1,1,1,2-tetrafluoroethoxy)perfluorobutanesulfonate, bis[4-(3,5-di(trifluoromethyl)-benzenesulfonyloxy)phenyl]phenylsulfonium 4-propoxypefluorobutanesulfonate, bis[4-(3,5-di(trifluoromethyl)-benzenesulfonyloxy)phenyl]phenylsulfonium perfluorobutanesulfonate, bis[4-(3,5-di(trifluoromethyl)benzenesulfonyl-oxy)phenyl]phenylsulfonium perfluoromethane-sulfonate, bis[4-trifluoromethylsulfonyloxy)phenyl] phenylsulfonium bis(perfluoro-ethyl-sulfonyl)imide, bis[4-trifluoromethylsulfonyloxy)phenyl]phenylsulfonium bis(trifluoromethyl-sulfonyl)imide, bis[4-trifluoromethylsulfonyloxy)phenyl]phenylsulfonium (perfluoromethylsulfonyl)(perfluorobutylsulfonyl)imide, bis[4-trifluoromethylsulfonyloxy)phenyl]phenylsulfonium bis(perfluoropropyl-sulfonyl)imide, bis[4-trifluoromethylsulfonyloxy)phenyl]phenylsulfonium bis(perfluorobutyl-sulfonyl)imide, bis[4-trifluoromethylsulfonyloxy)phenyl]phenylsulfonium tris(trifluoromethylsulfonyl)methide, bis[4-trifluoromethyl-sulfonyloxy)phenyl]phenylsulfonium 4-(1,1,1,2-tetrafluoroethoxy)perfluorobutanesulfonate, bis[4-trifluoromethylsulfonyloxy)phenyl]phenylsulfonium 4-propoxypefluorobutane sulfonate, bis[4-trifluoromethyl-sulfonyloxy)phenyl]phenylsulfonium perfluorobutane sulfonate, bis[4-trifluoromethylsulfonyloxy)phenyl]phenylsulfonium perfluoromethanesulfonate, bis(4-t-butylphenyl iodonium)triphenyl sulfonium perfluorobutane-1,4-disulfonate, bis(4-t-butylphenyl iodonium)triphenyl sulfonium perfluoropropane-1,3-disulfonate, bis(4-t-butylphenyl iodonium)triphenyl sulfonium perfluoropropane-1-carboxylate-3-sulfonate, bis(4-t-butylphenyl iodonium)triphenyl sulfonium perfluorobutane-1-carboxylate-4-sulfonate, bis(4-butylphenyl iodonium)triphenyl sulfonium perfluoromethane disulfonate, bis(4-t-butylphenyl iodonium) triphenyl sulfonium methane disulfonate, bis(4-t-butylphenyl iodonium)triphenyl sulfonium perfluoroethane disulfonate, bis(4-t-butylphenyl iodonium)triphenyl sulfonium ethane disulfonate, bis(triphenyl sulfonium)perfluorobutane-1,4-disulfonate, bis(triphenyl sulfonium)perfluoropropane-1,3-disulfonate, bis(benzoyltetramethylenesulfonium)perfluoropropane-1,3-disulfonate, bis(benzoyltetramethylenesulfonium)perfluorobutane-1,4-disulfonate, bis(tris(4-t-butyl phenyl)sulfonium)perfluorobutane-1,4-disulfonate, bis(tris(4-t-butyl phenyl)sulfonium)perfluorobutane-1,4-disulfonate, bis(tris(4-t-butyl phenyl)sulfonium)perfluoropropane-1,3-disulfonate, bis(tris(4-t-butyl phenyl)sulfonium)perfluoropropane-1,3-disulfonate, bis(4-t-butylphenyl diphenyl sulfonium)perfluorobutane-1,4-disulfonate, bis(4-t-butylphenyl diphenyl sulfonium)perfluoropropane-1,3-disulfonate, bis(triphenyl sulfonium)perfluoropropane-1-carboxylate-3-sulfonate, bis(triphenyl sulfonium)perfluorobutane-1-carboxylate-4-sulfonate, bis(benzoyltetramethylenesulfonium)perfluoropropane-1-carboxylate-3-sulfonate, bis(benzoyltetramethylenesulfonium)perfluorobutane-1-carboxylate-4-sulfonate, bis(tris(4-t-butyl phenyl)sulfonium)perfluoropropane-1-carboxylate-3-sulfonate, bis(tris(4-t-butyl phenyl)sulfonium)perfluorobutane-1-carboxylate-4-sulfonate, bis(4-t-butylphenyl diphenyl sulfonium)perfluoropropane-1-carboxylate-3-sulfonate, bis(4-t-butylphenyl diphenyl sulfonium)perfluorobutane-1-carboxylate-4-sulfonate, bis(4-t-butylphenyl iodonium)methane disulfonate, bis(triphenyl sulfonium)methane disulfonate, bis(4-t-butylphenyl iodonium)perfluoromethane disulfonate, bis(triphenyl sulfonium)perfluoromethane disulfonate, bis(benzoyltetramethylenesulfonium)perfluoromethane disulfonate, bis(benzoyl-tetramethylenesulfonium) methane disulfonate, bis(tris(4-t-butyl phenyl)sulfonium)perfluoromethane disulfonate, bis (tris(4-t-butyl phenyl)sulfonium)methane disulfonate, bis(4-t-butylphenyl diphenylsulfonium)perfluoromethane disulfonate, bis(4-t-butylphenyl diphenylsulfonium)methane disulfonate, bis(4-octyloxyphenyl)iodonium perfluorobutane-1,4-disulfonate, bis(4-octyloxyphenyl)iodonium ethane disulfonate, bis(4-octyloxyphenyl)iodonium perfluoroethane disulfonate, bis(4-octyloxyphenyl)iodonium perfluoropropane-1,3-disulfonate, bis(4-octyloxyphenyl)iodonium perfluoropropane-1-carboxylate-3-sulfonate, bis(4-octyloxyphenyl)iodonium perfluorobutane-1-carboxylate-4-sulfonate, bis(4-octyloxyphenyl)iodonium methane disulfonate, bis(4-octyloxyphenyl)iodonium perfluoromethane disulfonate, bis(4-octyloxyphenyl)phenyl sulfonium perfluorobutane-1,4-disulfonate, bis(4-octyloxyphenyl)phenyl sulfonium ethane disulfonate, bis(4-octyloxyphenyl)phenyl sulfonium perfluoroethane disulfonate, bis(4-octyloxyphenyl)phenyl sulfonium perfluoropropane-1,3-disulfonate, bis(4-octyloxyphenyl)phenyl sulfonium perfluoropropane-1-carboxylate-3-sulfonate, bis(4-octyloxyphenyl)phenyl sulfonium perfluorobutane-1-carboxylate-4-sulfonate, bis(4-octyloxyphenyl)phenyl sulfonium methane disulfonate, bis(4-octyloxyphenyl)phenyl sulfonium perfluoromethane disulfonate, bis[bis[4-pentafluorobenzenesulfonyloxy-phenyl]phenylsulfonium] perfluorobutane-1,4-disulfonate, bis[bis[4-pentafluorobenzene-sulfonyloxyphenyl]phenylsulfonium]ethane disulfonate, bis[bis[4-pentafluorobenzenesulfonyloxyphenyl]phenyl-sulfonium]perfluoroethane disulfonate, bis[bis[4-pentafluorobenzene-sulfonyloxyphenyl]phenylsulfonium]perfluoropropane-1,3-disulfonate, bis[bis[4-pentafluorobenzenesulfonyloxyphenyl] phenylsulfonium]perfluoropropane-1-carboxylate-3-sulfonate, bis[bis[4-pentafluorobenzenesulfonyloxyphenyl]phenyl]sulfonium]perfluorobutane-1-carboxylate-4-sulfonate, bis[bis[4-pentafluorobenzenesulfonyloxyphenyl] phenylsulfonium]methane disulfonate, bis[bis[4-pentafluorobenzenesulfonyloxyphenyl] phenylsulfonium]perfluoromethane disulfonate, bis[bis[4-(3,5-di(trifluoromethyl)benzenesulfonyloxy)-phenyl]phenylsulfonium]perfluorobutane-1,4-disulfonate, bis[bis[4-(3,5-di(trifluoromethyl)-benzenesulfonyloxy)phenyl]phenylsulfonium]ethane disulfonate, bis[bis[4-(3,5-di(trifluoromethyl)benzene-sulfonyloxy)phenyl]phenylsulfonium]perfluoroethane disulfonate, bis[bis[4-(3,5-di(trifluoromethyl)benzene-sulfonyloxy)phenyl]phenylsulfonium]perfluoropropane-1,3-disulfonate, bis[bis[4-(3,5-di(trifluoro-methyl)-benzenesulfonyloxy)phenyl]phenylsulfonium] perfluoropropane-1-carboxylate-3-sulfonate, bis[bis[4-(3,5-di(trifluoromethyl)benzenesulfonyloxy)-phenyl] phenylsulfonium]perfluorobutane-1-carboxylate-4-sulfonate, bis[bis[4-(3,5-di(trifluoromethyl) benzenesulfonyloxy)phenyl]phenylsulfonium]methane disulfonate, bis(4-t-butylphenyl iodonium)ethane disulfonate, bis(4-t-butylphenyl iodonium)perfluoroethane disulfonate, bis(triphenyl sulfonium)ethane disulfonate, bis(triphenyl sulfonium) perfluoroethane disulfonate, bis(benzoyltetramethylene-sulfonium)perfluoroethane disulfonate, bis(benzoyltetramethylenesulfonium) ethane disulfonate, bis(tris(4-t-butyl phenyl)sulfonium) perfluoroethane disulfonate, bis(tris(4-t-butyl phenyl) sulfonium)ethane disulfonate, bis(4-t-butylphenyl diphenyl-sulfonium)perfluoroethane disulfonate, bis(4-t-butylphenyl diphenylsulfonium)ethane disulfonate, bis[bis[2-methyladamantylacetyloxymethoxyphenyl] phenyl-sulfonium]perfluorobutane-1,4-disulfonate, bis [bis[2-methyladamantylacetyl-oxymethoxyphenyl] phenylsulfonium]ethane disulfonate, bis[bis[2-methyladamantylacetyloxymethoxyphenyl]phenylsulfonium] perfluoroethane disulfonate, bis[bis[2-methyladamantylacetyloxymethoxyphenyl]phenylsulfonium]perfluoro-propane-1,3-disulfonate, bis[bis[2-methyladamantylacetyloxymethoxyphenyl]phenylsulfonium]perfluoropropane-1-carboxylate-3-sulfonate, bis[bis[2-methyl-adamantylacetyloxymethoxyphenyl]phenylsulfonium]perfluorobutane-1-carboxylate-4-sulfonate, bis[bis[2-methyladamantylacetyloxymethoxyphenyl]phenylsulfonium]methane disulfonate, bis[bis[2-methyladamantylacetyloxy-methoxyphenyl]phenylsulfonium]perfluoromethane disulfonate, bis[bis[4,4-bis(trifluoromethyl)-3-oxatricyclo[4.2.1.0$^{2,5}$]-nonylmethoxyphenyl]phenyl sulfonium] perfluorobutane-1,4-disulfonate, bis[bis[4,4-bis(trifluoromethyl)-3-oxatricyclo-[4.2.1.0$^{2,5}$]-nonylmethoxy-phenyl]phenyl sulfonium]ethane disulfonate, bis[bis[4,4-bis(trifluoromethyl)-3-oxatricyclo[4.2.1.0$^{2,5}$]-nonylmethoxyphenyl]phenyl sulfonium]-perfluoroethane disulfonate, bis[bis[4,4-bis(trifluoromethyl)-3-oxatricyclo[4.2.1.0$^{2,5}$]-nonylmethoxyphenyl]phenyl sulfonium]perfluoropropane-1,3-disulfonate, bis[bis[4,4-bis(trifluoro-methyl)-3-oxatricyclo[4.2.1.0$^{2,5}$]-nonylmethoxyphenyl]phenyl sulfonium]-perfluoropropane-1-carboxylate-3-sulfonate, bis[bis[4,4-bis(trifluoro-methyl)-3-oxatricyclo[4.2.1.0$^{2,5}$]-nonylmethoxyphenyl]phenyl sulfonium] perfluoro-butane-1-carboxylate-4-sulfonate, bis[bis[4,4-bis(trifluoromethyl)-3-oxatricyclo-[4.2.1.0$^{2,5}$]-nonylmethoxyphenyl]phenyl sulfonium]methane disulfonate, and bis[bis[4,4-bis(trifluoromethyl)-3-oxatricyclo[4.2.1.0$^{2,5}$]-nonylmethoxyphenyl]phenyl sulfonium]perfluoromethane disulfonate;

diazomethane derivatives such as bis(benzenesulfonyl)diazomethane, bis(p-toluenesulfonyl)diazomethane, bis(xylenesulfonyl)diazomethane, bis(cyclohexylsulfonyl)diazomethane, bis(cyclopentylsulfonyl)diazomethane, bis(n-butylsulfonyl)diazomethane, bis(isobutylsulfonyl)diazomethane, bis(sec-butylsulfonyl)diazomethane, bis(n-propylsulfonyl)diazomethane, bis(isopropylsulfonyl)diazomethane, bis(tert-butylsulfonyl)diazomethane, bis(n-amylsulfonyl)diazomethane, bis(isoamylsulfonyl)diazomethane, bis(sec-amylsulfonyl)diazomethane, bis(tert-amylsulfonyl)diazomethane, 1-cyclohexylsulfonyl-1-(tert-butylsulfonyl)diazomethane, 1-cyclohexylsulfonyl-1-(tert-amylsulfonyl)diazomethane, and 1-tert-amylsulfonyl-1-(tert-butylsulfonyl)diazomethane;

glyoxime derivatives such as bis-O-(p-toluenesulfonyl)-α-dimethylglyoxime, bis-O-(p-toluenesulfonyl)-α-diphenylglyoxime, bis-O-(p-toluenesulfonyl)-α-dicyclohexylglyoxime, bis-O-(p-toluenesulfonyl)-2,3-pentanedioneglyoxime, bis-O-(p-toluenesulfonyl)-2-methyl-3,4-pentanedioneglyoxime, bis-O-(n-butanesulfonyl)-α-dimethylglyoxime, bis-O-(n-butanesulfonyl)-α-diphenylglyoxime, bis-O-(n-butanesulfonyl)-α-dicyclohexylglyoxime, bis-O-(n-butanesulfonyl)-2,3-pentanedioneglyoxime, bis-O-(n-butanesulfonyl)-2-methyl-3,4-pentanedioneglyoxime, bis-O-(methanesulfonyl)-α-dimethylglyoxime, bis-O-(trifluoromethanesulfonyl)-α-dimethylglyoxime, bis-O-(1,1,1-trifluoroethanesulfonyl)-α-dimethylglyoxime, bis-O-(tert-butanesulfonyl)-α-dimethylglyoxime, bis-O-(perfluorooctanesulfonyl)-α-dimethylglyoxime, bis-O-(cyclohexanesulfonyl)-α-dimethylglyoxime, bis-O-(benzenesulfonyl)-α-dimethylglyoxime, bis-O-(p-fluorobenzenesulfonyl)-α-dimethylglyoxime, bis-O-(p-tert-butylbenzenesulfonyl)-α-dimethylglyoxime, bis-O-(xylenesulfonyl)-α-dimethylglyoxime, and bis-O-(camphorsulfonyl)-α-dimethylglyoxime;

bissulfone derivatives such as bisnaphthylsulfonylmethane, bistrifluoromethylsulfonylmethane, bismethylsulfonylmethane, bisethylsulfonylmethane, bispropylsulfonylmethane, bisisopropylsulfonylmethane, bis-p-toluenesulfonylmethane, and bisbenzenesulfonylmethane;

β-ketosulfonic acid derivatives such as 2-cyclohexylcarbonyl-2-(p-toluenesulfonyl)propane and 2-isopropylcarbonyl-2-(p-toluenesulfonyl)propane;

disulfone derivatives such as diphenyl disulfone and dicyclohexyl disulfone;

nitrobenzyl sulfonate derivatives such as 2,6-dinitrobenzyl p-toluenesulfonate and 2,4-dinitrobenzyl p-toluenesulfonate;

sulfonic acid ester derivatives such as 1,2,3-tris(methanesulfonyloxy)benzene, 1,2,3-tris(trifluoromethanesulfonyloxy)benzene, and 1,2,3-tris(p-toluenesulfonyloxy)benzene; and sulfonic acid esters of N-hydroxyimides such as N-hydroxysuccinimide methanesulfonate, N-hydroxysuccinimide trifluoromethanesulfonate, N-hydroxysuccinimide ethanesulfonate, N-hydroxysuccinimide 1-propanesulfonate, N-hydroxysuccinimide 2-propanesulfonate, N-hydroxysuccinimide 1-pentanesulfonate, N-hydroxysuccinimide 1-octanesulfonate, N-hydroxysuccinimide p-toluenesulfonate, N-hydroxysuccinimide p-methoxybenzenesulfonate, N-hydroxysuccinimide 2-chloroethanesulfonate, N-hydroxysuccinimide benzenesulfonate, N-hydroxysuccinimide 2,4,6-trimethylbenzenesulfonate, N-hydroxysuccinimide 1-naphthalenesulfonate, N-hydroxysuccinimide 2-naphthalenesulfonate, N-hydroxy-2-phenylsuccinimide methanesulfonate, N-hydroxymaleimide methanesulfonate, N-hydroxymaleimide ethanesulfonate, N-hydroxy-2-phenylmaleimide methanesulfonate, N-hydroxyglutarimide methanesulfonate, N-hydroxyglutarimide benzenesulfonate, N-hydroxyphthalimide methanesulfonate, N-hydroxyphthalimide benzenesulfonate, N-hydroxyphthalimide trifluoromethanesulfonate, N-hydroxyphthalimide p-toluenesulfonate, N-hydroxynaphthalimide methanesulfonate, N-hydroxynaphthalimide benzenesulfonate, N-hydroxy-5-norbornene-2,3-dicarboxyimide methanesulfonate, N-hydroxy-5-norbornene-2,3-dicarboxyimide trifluoromethanesulfonate, and N-hydroxy-5-norbornene-2,3-dicarboxyimide p-toluenesulfonate.

Q, which includes quenchers and photobases, include compounds such as

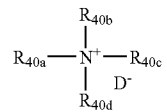

where $R_{40a}$, $R_{40b}$, $R_{40c}$, and $R_{40d}$ stand for the same as $R_{10b}$ and $R_{10c}$ as well as hydrogen atoms and D$^-$ is a basic anion having a pK$_a$ value of −3 to +7;

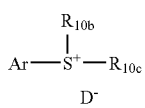

Where Ar, $R_{10b}$, $R_{10c}$, and $D^-$ are as defined above (examples include tetramethylammonium trifluoromethanesulfonate, tetramethylammonium nonafluorobutanesulfonate, tetra-n-butylammonium nonafluorobutanesulfonate, tetraphenylammonium nonafluorobutanesulfonate, tetramethylammonium p-toluenesulfonate, (p-methoxybenzyl)dimethylphenylammonium trifluoromethanesulfonate, (p-methoxybenzyl) trimethylammonium trifluoromethanesulfonate;

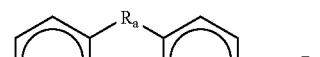

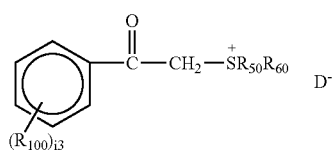

where $R_a$ represents $(CH_2)_{i4}$, where i4 is 0 or 1, O or S; $R_{50}$ and $R_{60}$ stand the same as for $R_{10b}$, or $R_{50}$ and $R_{60}$ together with the S atom to which they are attached form a 5-, 6-, or 7-membered ring which can be unsubstituted or substituted; $R_{80}$, $R_{90}$, and $R_{100}$ each individually represent $C_{1-4}$ alkyl, $C_{1-4}$ alkoxy, or halide; i1 and i2 are each 1 to 4; and i3 is 1 to 5. $D^-$ is as defined above.

For D above, in some instances, it can represent a hydroxyl group or OR' (wherein R' represents a C1-C4 alkyl), $OCOR_{10a}$, $OCOO^-$, or $OSOO^-$.

Other examples include compounds such as primary, secondary and tertiary aliphatic amines, mixed amines, aromatic amines, heterocyclic amines, nitrogen-containing compounds with a carboxy group, nitrogen containing compounds with a sulfonyl group, nitrogen-containing compounds with a hydoxy group, nitrogen-containing compounds with a hydroxyphenyl group, alcoholic nitrogen-containing compounds, amide derivatives, imide derivatives and nitrogen-containing compound having one or more oxygen atoms.

Non-limiting examples of the foregoing Q include:

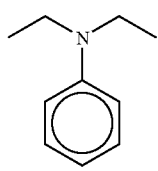
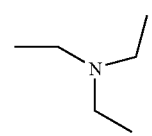
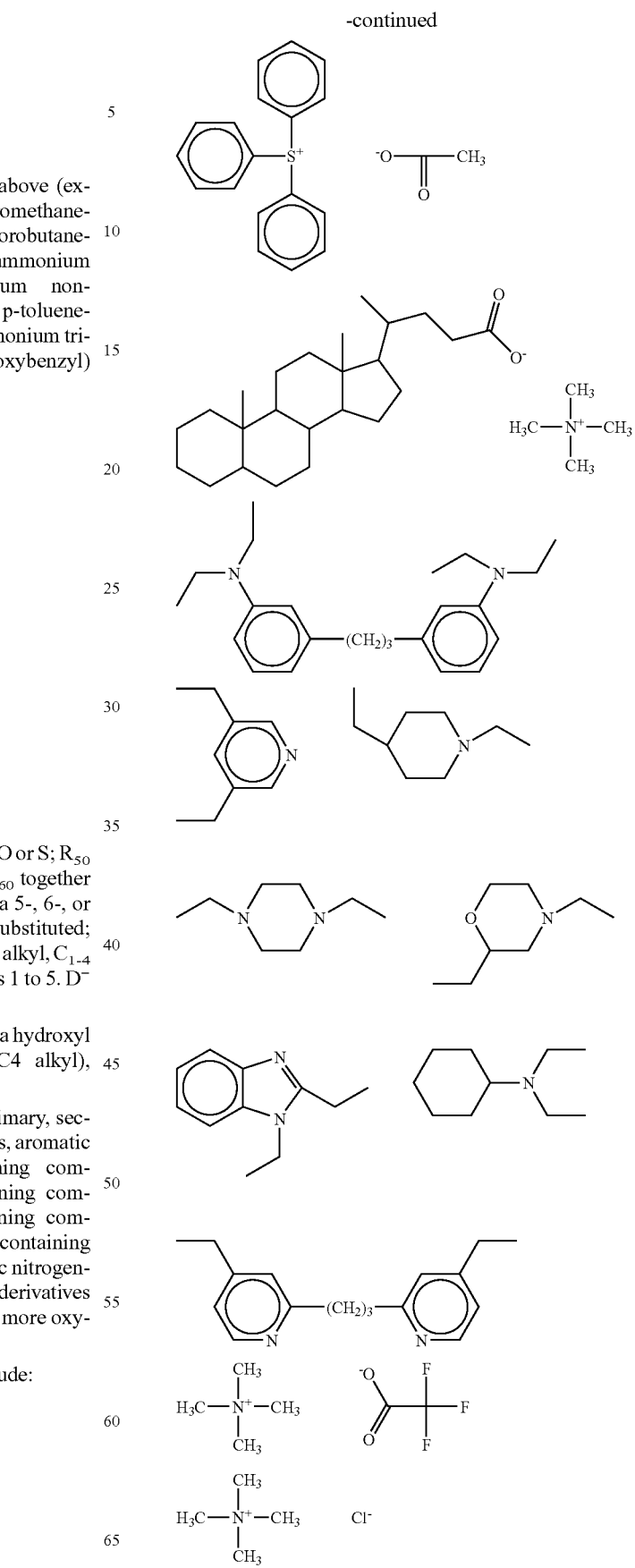

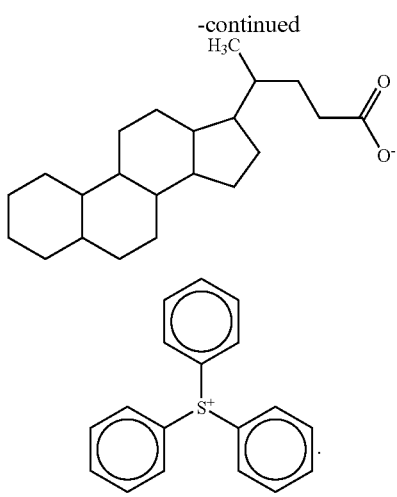

For formula (I) where -(L-(G))$_p$ is attached to W, where W is PAG or Q, -(L-(G))$_p$ can be attached to the cationic portion, the anionic portion, or both the cationic and anionic portions of PAG or Q. In the instance where PAG or Q are nonionic, PAG or Q can contain -(L-(G))$_p$ anywhere on the molecule of PAG or Q. Whether PAG or Q are ionic or non-ionic, the placement of -(L-(G))$_p$ thereon should be such that the activity of the molecule is not affected. Those skilled in the art will know how and appreciate how this is accomplished.

L represents a direct bond or a linking group. Examples of a linking group include substituted or unsubstituted alkyl groups optionally containing one or more O atoms, substituted or unsubstituted cycloalkyl groups, substituted or unsubstituted aryl groups, substituted or unsubstituted heteroaryl groups, substituted or unsubstituted alkyl groups having inside a linking group (e.g., ether, ester, amido), and substituted or unsubstituted aryl groups having inside a linking group, where two or more hydrogen atoms are removed from the alkyl, cycloalkyl, aryl, and heteroaryl groups to form divalent, trivalent, tetravalent, etc linking groups.

Thus, examples of the compounds of W-(L-(G))$_p$ include, but are not limited to

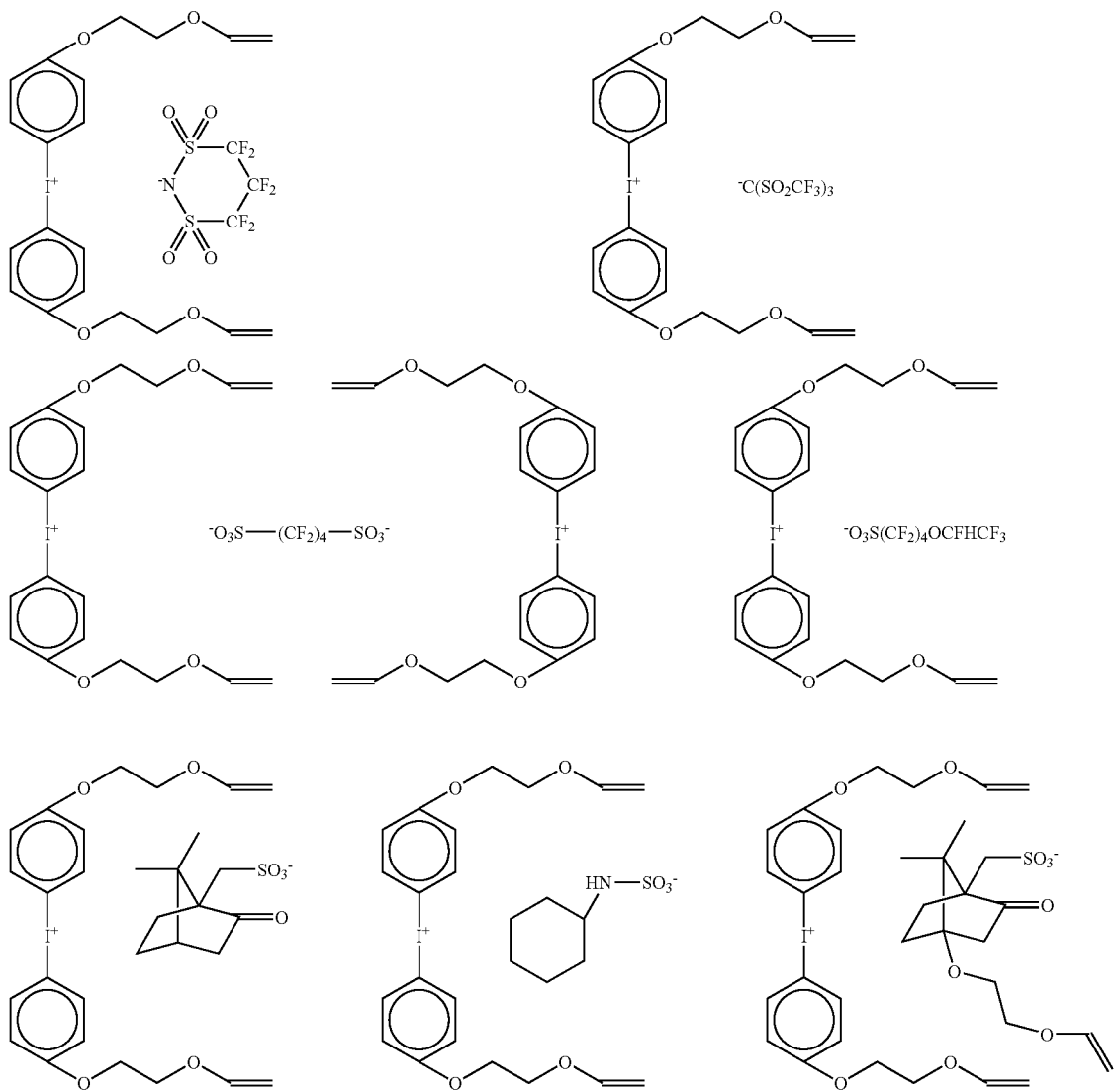

-continued
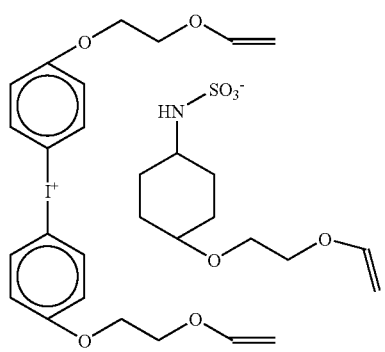
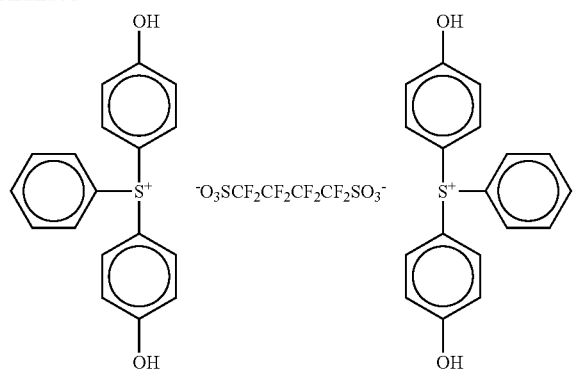
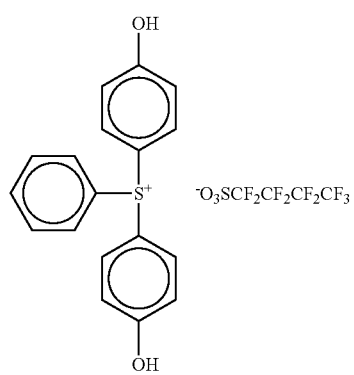
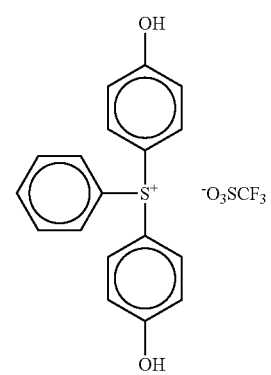
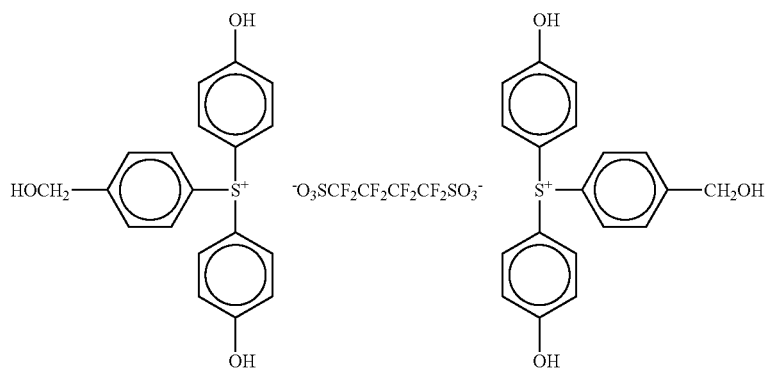
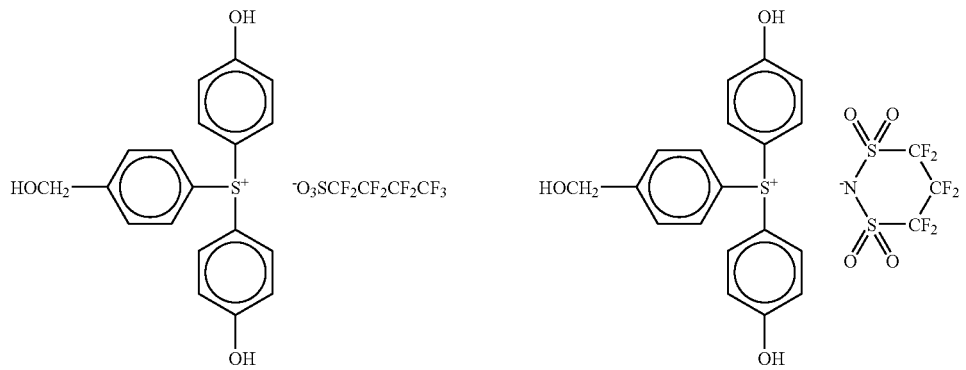

23
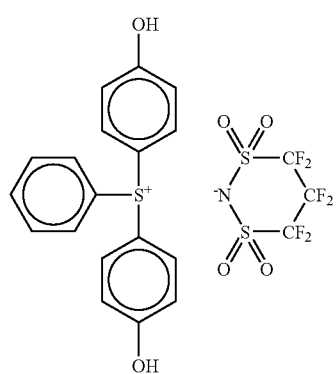
24
-continued
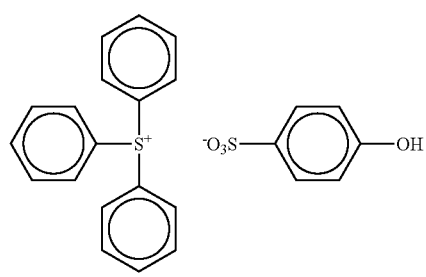
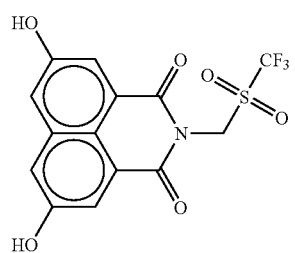
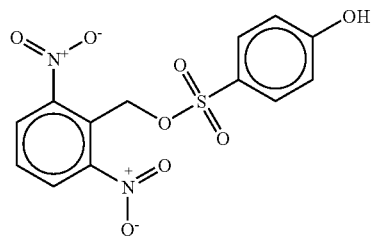
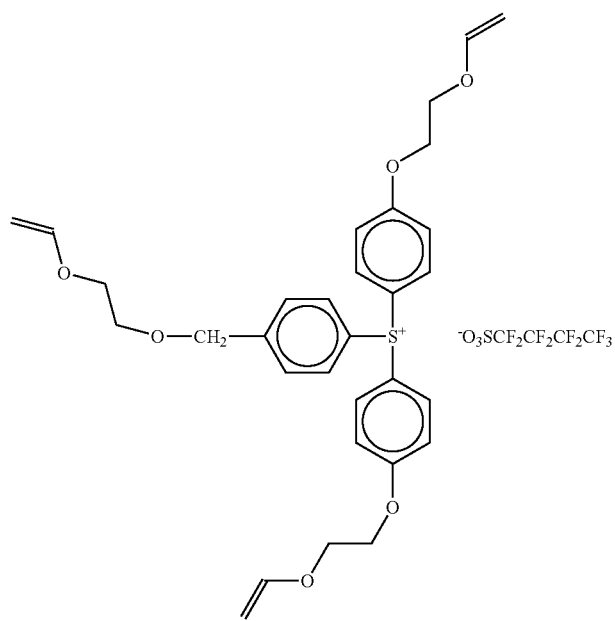

-continued
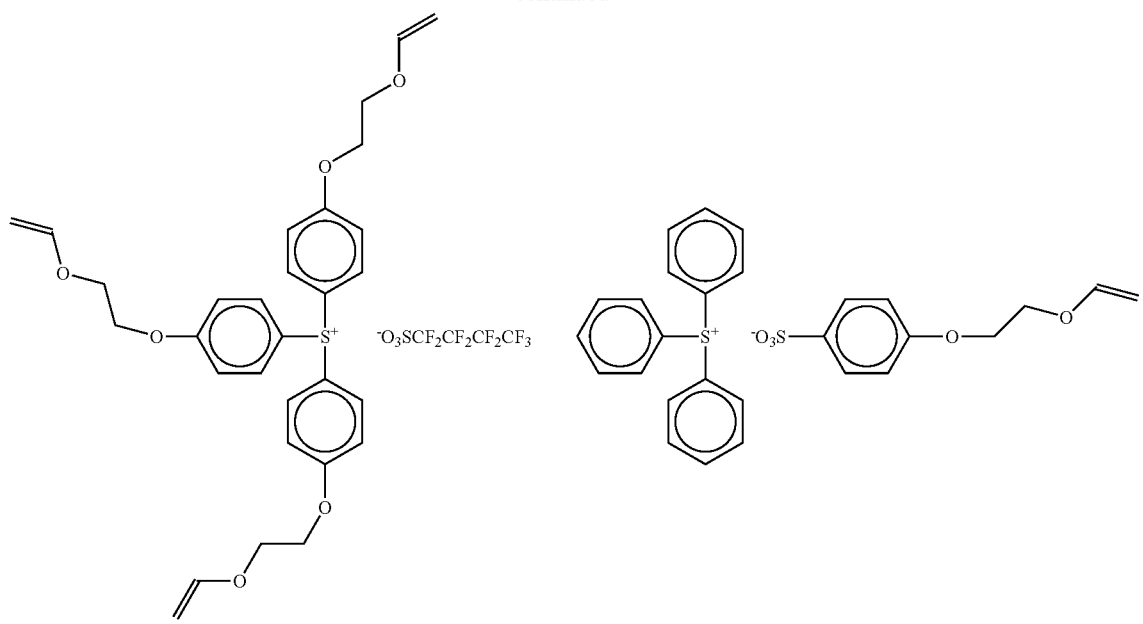
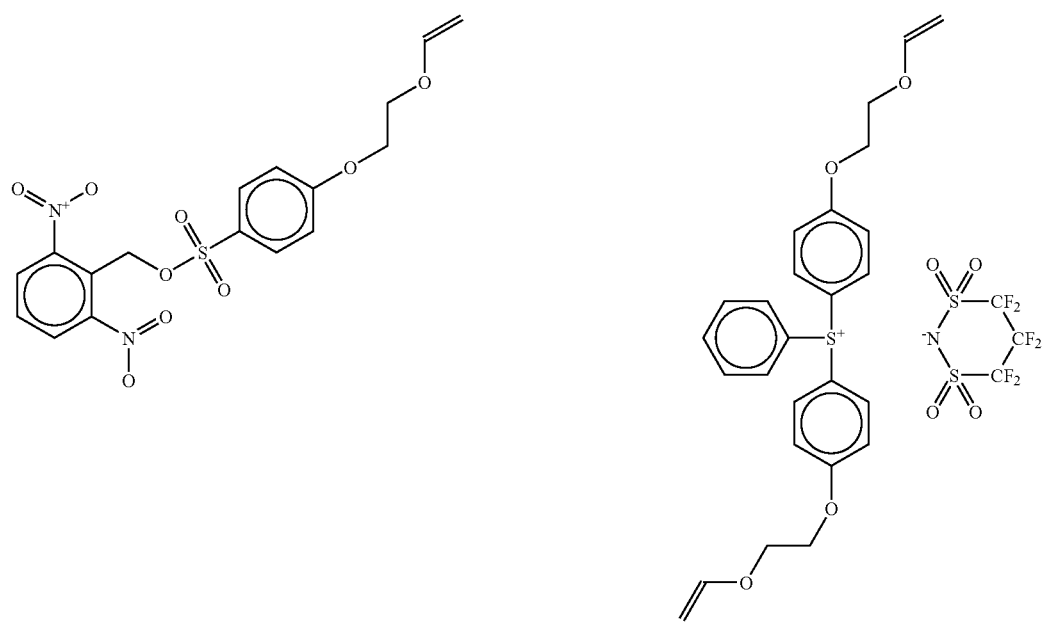

-continued
27
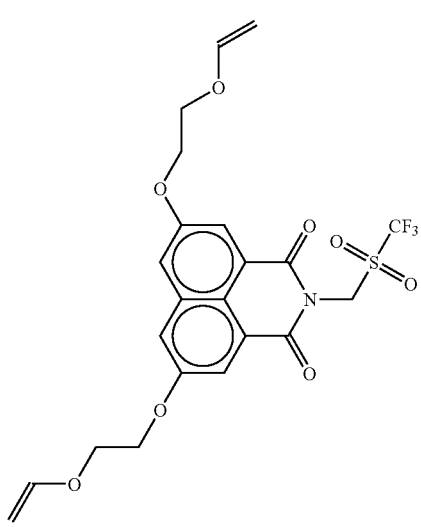
28
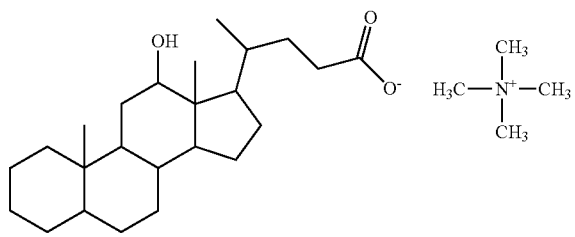
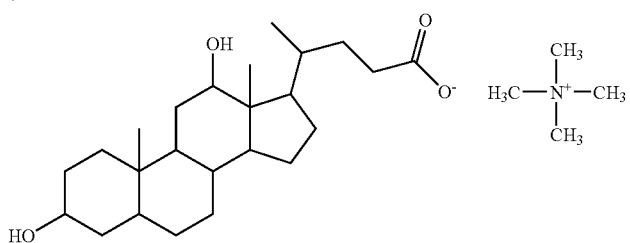
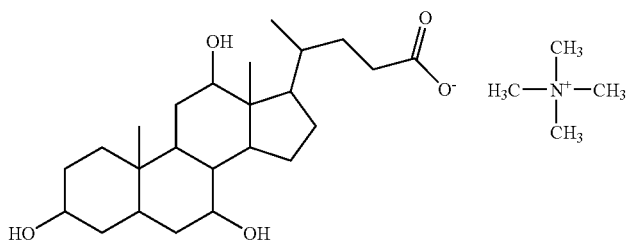
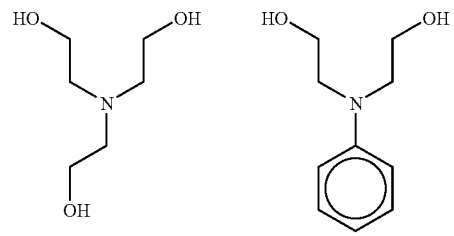
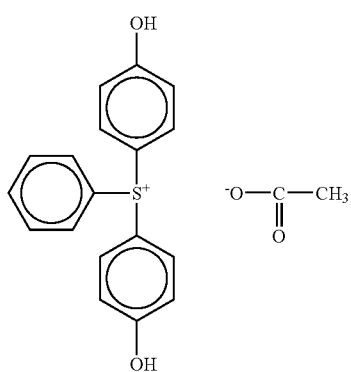
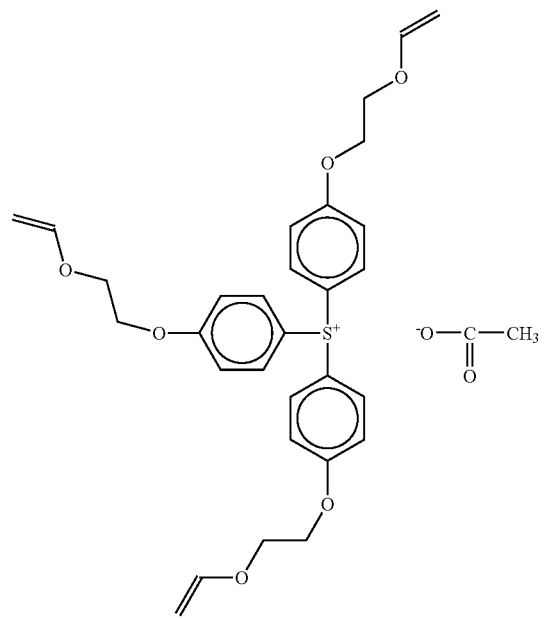

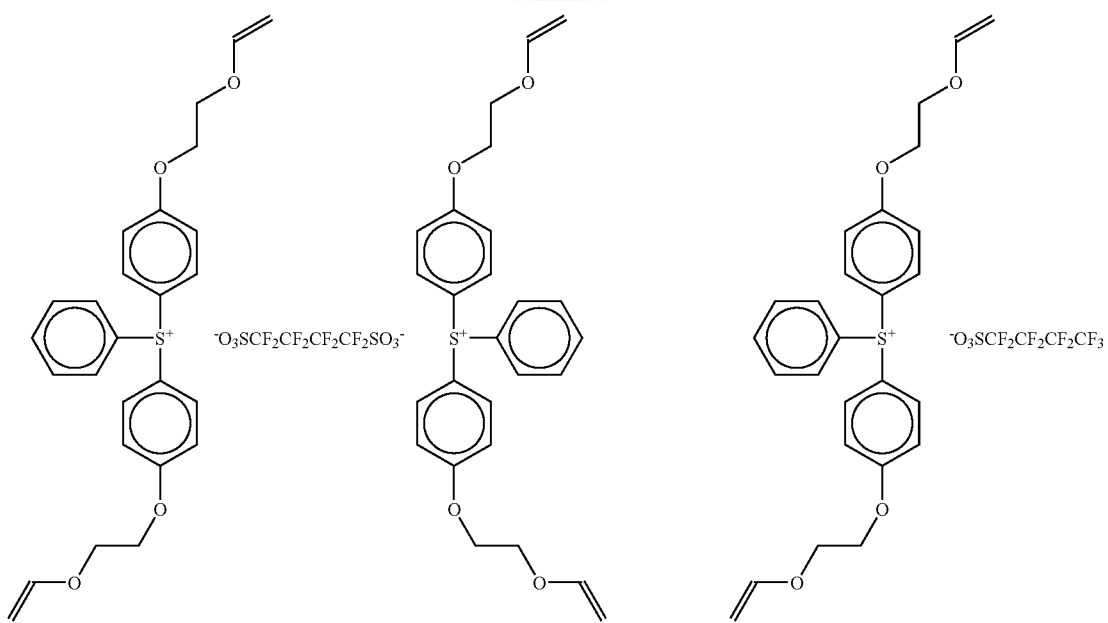
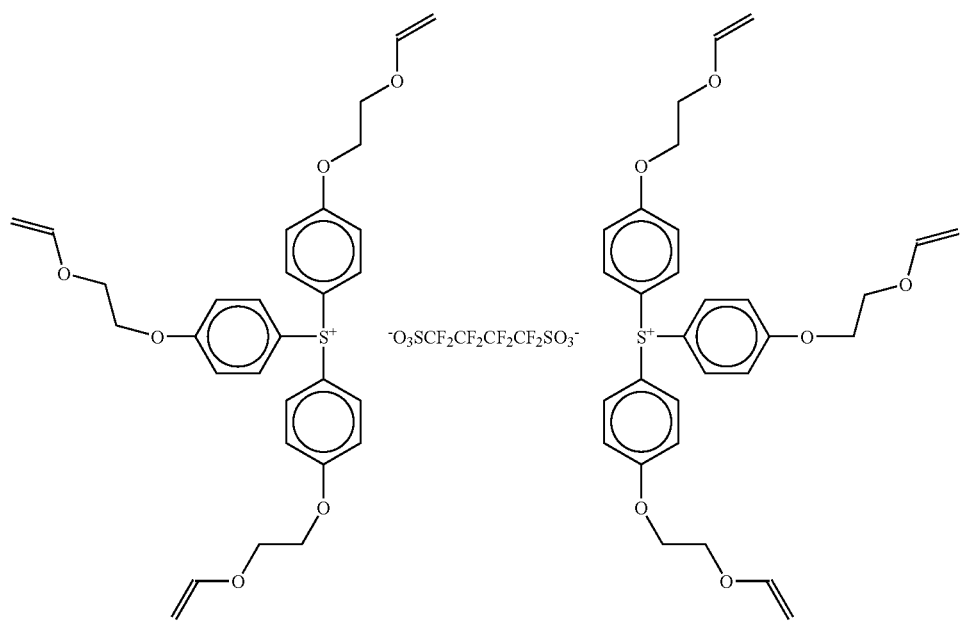

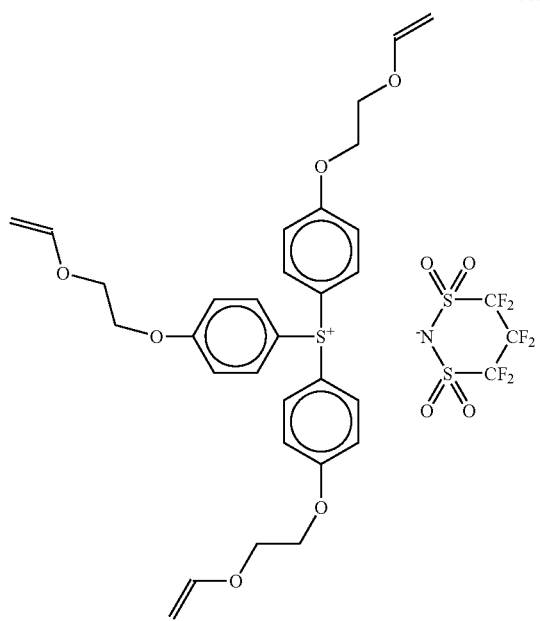
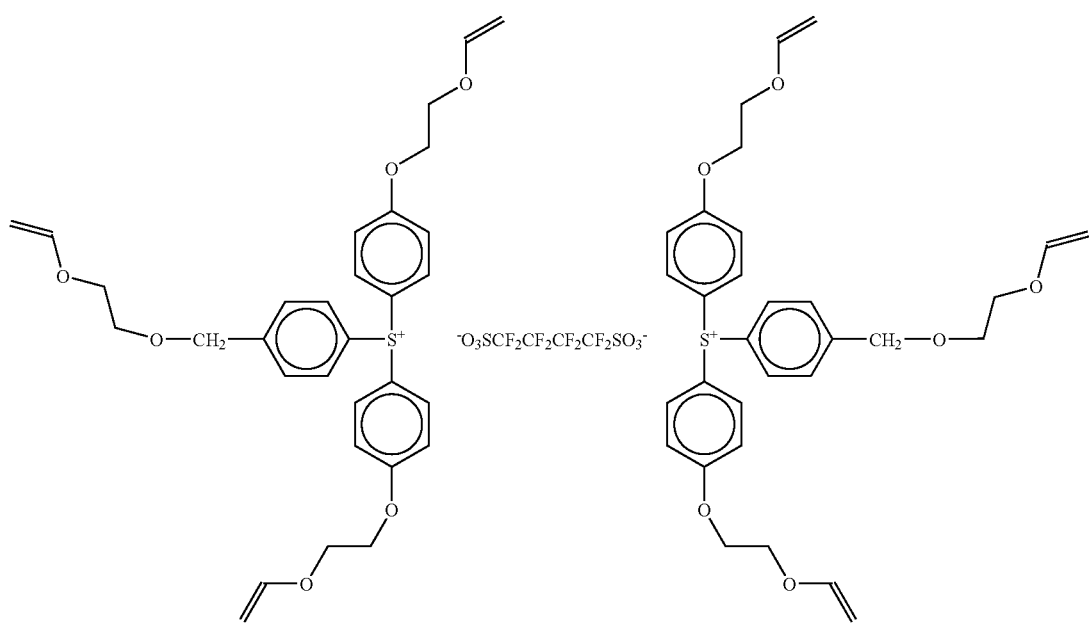

-continued
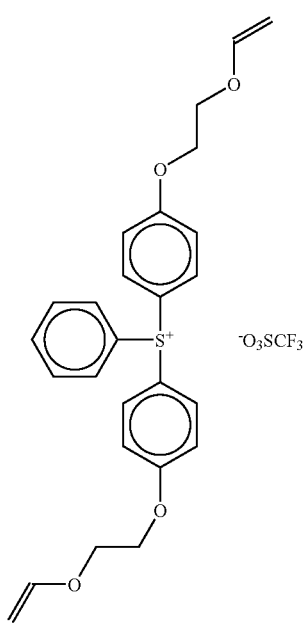
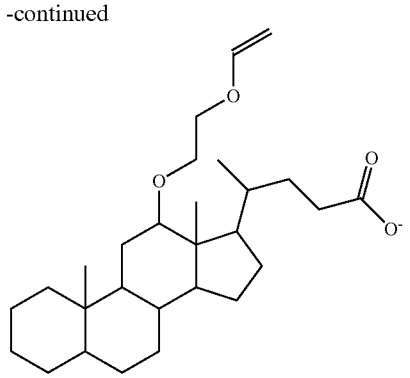 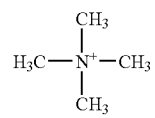
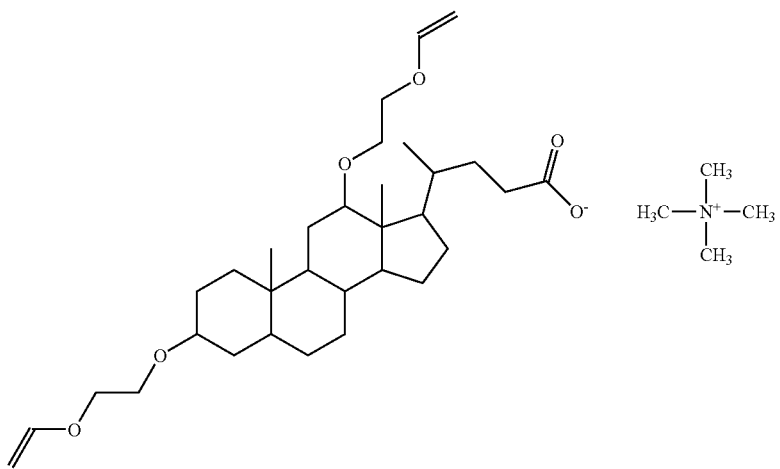 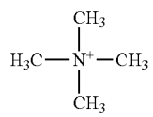
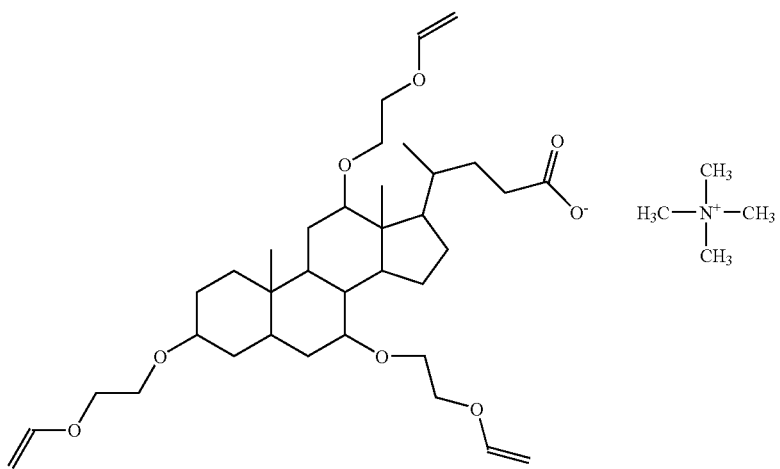 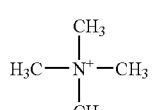

35
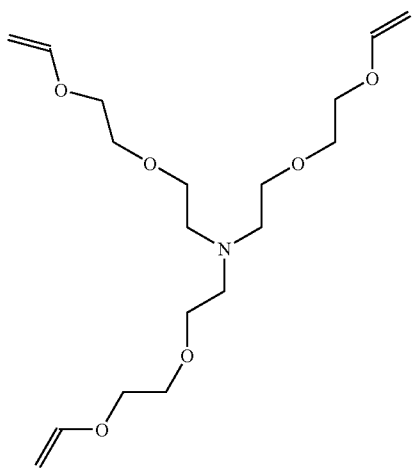
36
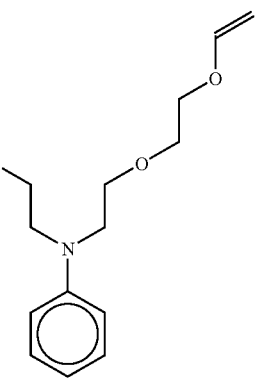
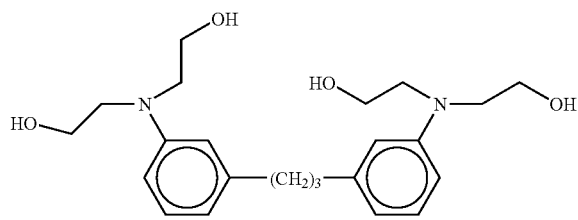
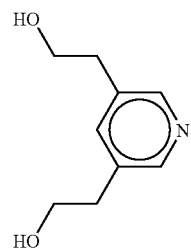
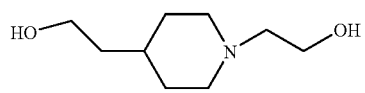
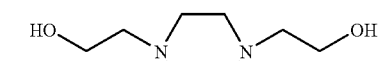
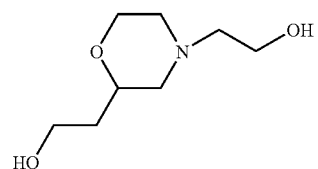
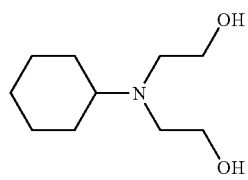
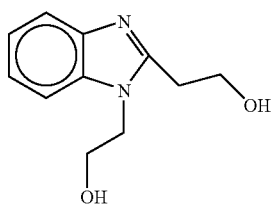
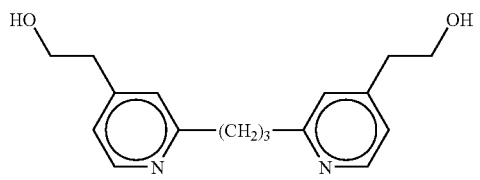
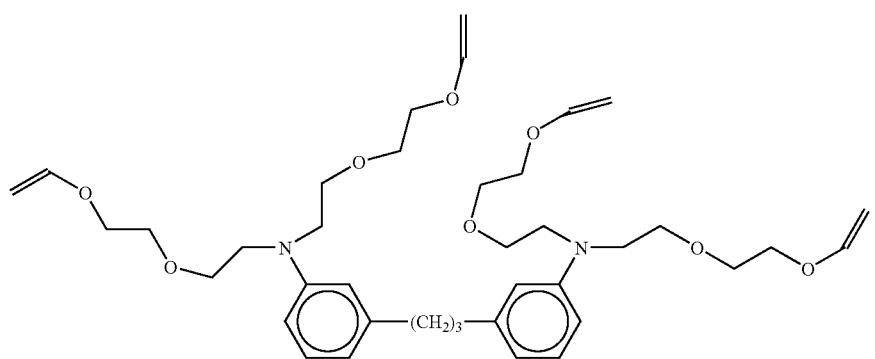

37
38
-continued
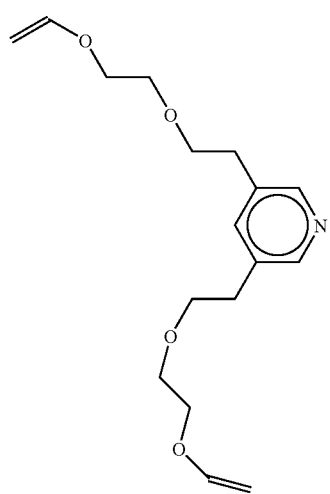
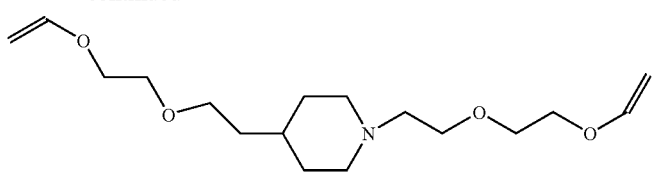
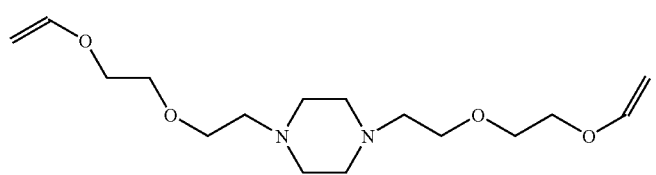
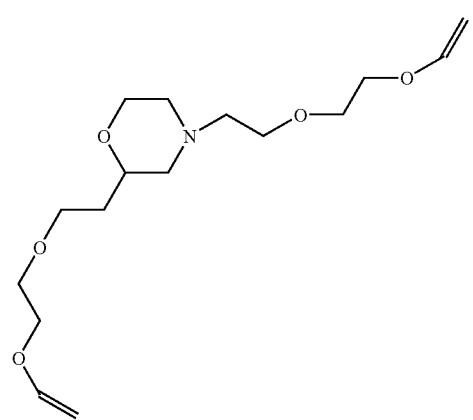
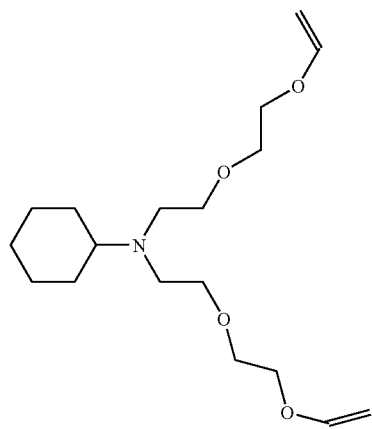
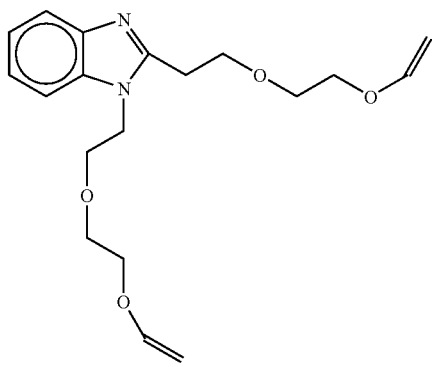
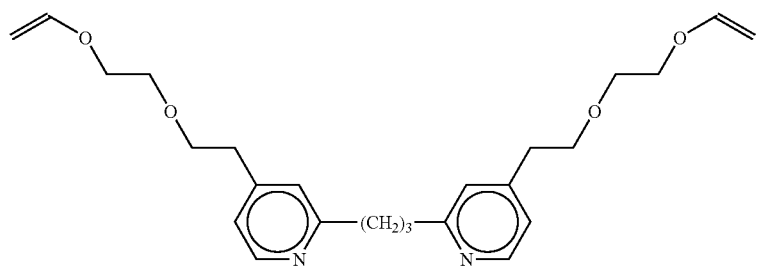

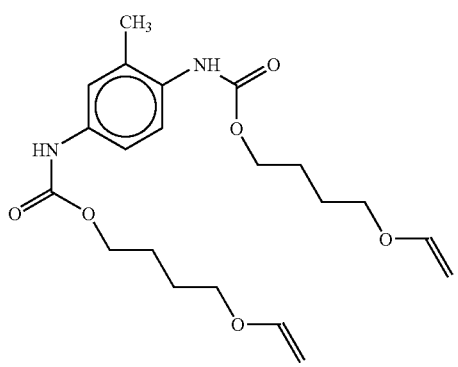
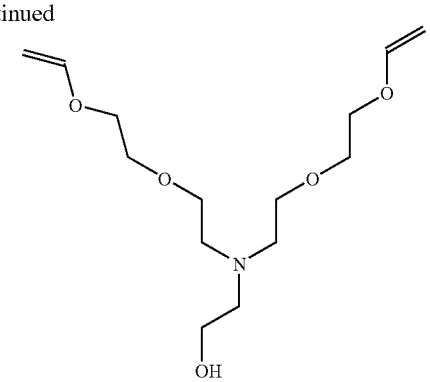
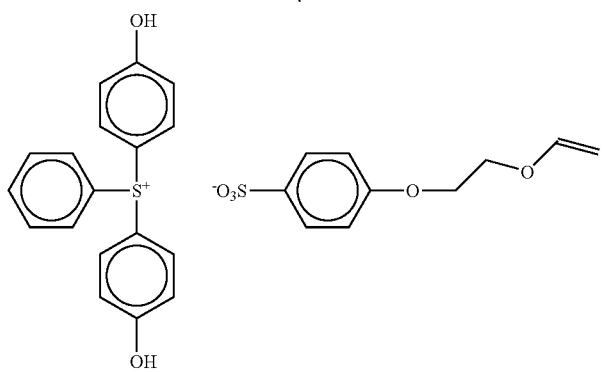
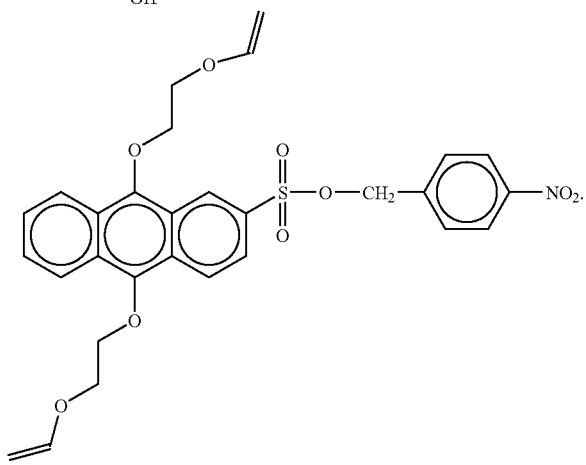

Examples of W-(L-(G))$_p$ herein include, but are not limited to, bis(4-vinyloxyethyloxyphenyl)phenylsulfonium triflate, bis(4-vinyloxyethyloxyphenyl)phenylsulfonium nonaflate, bis(4-vinyloxyethyloxyphenyl)phenylsulfonium 10-camphorsulfonate, bis(4-vinyloxyethyloxyphenyl)phenylsulfonium cyclohexane sulfamate, bis(4-vinyloxyethyloxyphenyl)phenylsulfonium tris(trifluoromethanesulfonyl)methide, bis(bis(4-vinyloxyethyloxyphenyl)phenylsulfonium) 1,4-perfluorobutanedisulfonate, tris(4-vinyloxyethyloxyphenyl)sulfonium nonaflate, bis(tris(4-vinyloxyethyloxyphenyl)sulfonium) 1,4-perfluorobutanedisulfonate, tris(4-vinyloxyethyloxyphenyl)sulfonium 1,1,2,2,3,3-hexafluoropropane-1,3-disulfonimide, 2,6-dinitrobenzyl-4-vinyloxyethoxy benzene sulfonate, triphenylsulfonium 4-vinyoxyethoxybenzene sulfonate, tetramethylammonium deoxycholate, tetramethylammonium lithocholate, tetramethylammonium cholate, N,N-divinyloxyethoxyethylbenzeneamine, 3α,7α,12α-trivinyloxyethyloxy-5β-cholanic acid tetramethylammonium salt, 3α-vinyloxyethyloxy-5β-cholanic acid tetramethylammonium salt, bis(4-hydroxyphenyl)phenyl sulfonium 4-vinyoxyethoxybenzene sulfonate, 3α,12α-divinyloxyethyloxy-5β-cholanic acid tetramethylammonium salt, N-trifluoromethylsulfonyloxy-3,6-divinyloxyethoxy-1,8-naphthalimide, p-nitrobenzyl-9,10-divinyloxyethoxy anthracene-2-sulfonate, bis(4-vinyloxyethyloxyphenyl)iodonium 10-camphorsulfonate, bis(4-vinyloxyethyloxyphenyl)iodonium cyclohexane sulfamate, bis(4-vinyloxyethyloxyphenyl)iodonium 4-vinyloxyethyloxy-10-camphorsulfonate, bis(4-vinyloxyethyloxyphenyl)iodonium 4-vinyloxyethyloxy-cyclohexane sulfamate, bis(4-vinyloxyethyloxyphenyl)iodonium tris(trifluoromethanesulfonyl)methide, bis(bis(4-vinyloxyethyloxyphenyl)iodonium) 1,4-perfluorobutanedisulfonate, bis(4-vinyloxyethyloxyphenyl)iodonium 1.1,2,2,3,3-hexafluoropropane-1,3-disulfonimide, bis(4-vinyloxyethyloxyphenyl)iodonium 1,1,1,2-tetrafluoroethoxyoctafluorobutanesulfonate, tris(4-vinyloxyethyloxyphenyl)sulfonium 1,1,1,2- tetrafluoroethoxyoctafluorobutanesulfonate, bis(4-vinyloxy-ethyloxyphenyl)phenylsulfonium 1,1,1,2-tetrafluoroethoxyoctafluorobutanesulfonate, and bis(4-vinyloxyethyloxyphenyl)iodonium 1,1,1,2-tetrafluoroethoxyoctafluorobutanesulfonate.

Also disclosed is a coated substrate comprising a substrate having thereon; a layer of the antireflective coating composition of the present invention; and a layer of a photoresist composition above the antireflective coating composition.

Also disclosed is a process for forming an image comprising: a) forming a coating of the antireflective coating composition of the present invention on a substrate; b) baking the antireflective coating, c) providing a coating of a top photoresist layer over the antireflective coating; d) developing an image using an aqueous alkaline developer; e) optionally heating the substrate prior to and after development and, f) dry etching the antireflective coating.

Also disclosed is a process for forming an image comprising a) forming a coating of the bottom photoimageable antireflective coating composition of the present invention on a substrate; b) baking the antireflective coating, c) providing a coating of a top photoresist layer over the antireflective coating; d) imagewise exposing the photoresist and antireflective coating layers to actinic radiation of same wavelength; e) post-exposure baking the photoresist and antireflective coating layers on the substrate; and, f) developing the photoresist and antireflective coating layers with an aqueous alkaline solution.

It is also possible to form a positive bottom photoimageable antireflective coating composition which is capable of being developed with an aqueous alkali developer and which is coated below a positive photoresist, wherein the antireflective coating composition consists of (a) either (a1) a mixture of at least one compound of formula (1) and at least one compound of formula (2)

$$PAG\text{-}(\text{-}L\text{-}OH)_p \qquad (1)$$

$$PAG\text{-}(\text{-}L\text{-}OCH=CH_2)_p \qquad (2)$$

or
(a2) at least one compound of formula (5)

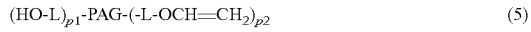
$$(HO\text{-}L)_{p1}\text{-}PAG\text{-}(\text{-}L\text{-}OCH=CH_2)_{p2} \qquad (5)$$

and
(b) a solvent,
where PAG is a photoacid generator, each L is a direct bond or a linking group; p is an integer 1 to 12; p1 and p2 are each greater than or equal to 1 and p1+p2 equal 2 to 12, wherein at least one PAG contains a chromophore moiety. The chromophore moieties are like those that are disclosed herein which are useful in PAGs. This composition can further comprise a compound selected from

$$Q\text{-}(\text{-}L\text{-}OH)_p \qquad (3)$$

$$Q\text{-}(\text{-}L\text{-}OCH=CH_2)_p \qquad (4)$$

$$(HO\text{-}L)_{p3}\text{-}Q\text{-}(\text{-}L\text{-}OCH=CH_2)_{p4} \qquad (6)$$

and mixtures thereof, where Q is a quencher, each L is a direct bond or a linking group; p is an integer 1 to 12; p3 and p4 are each greater than or equal to 1 and p3+p4 equal 2 to 12. With this type of composition, there would be no need for any polymer resin and can be processed in the same manner as the positive bottom antireflective coating composition discussed herein.

Regarding the positive bottom photoimageable antireflective coating compositions, a polymer useful in positive bottom photoimageable antireflective coating compositions include a polymer selected from the group of (i) a polymer comprising at least one recurring unit with an acid labile group; (ii) a polymer comprising at least one recurring unit with an acid labile group and at least one recurring unit with an absorbing chromophore or (iii) a polymer comprising at least one recurring unit with a hydroxyl and/or a carboxyl group and at least one recurring unit with an absorbing chromophore.

One polymer useful in positive bottom photoimageable antireflective coating compositions is (i) a polymer which comprises at least one unit with an acid labile group. One function of the polymer is to provide a good coating quality and another is to enable the antireflective coating to change solubility from exposure to development. The acid labile groups in the polymer provide the necessary solubility change. The polymer without the acid labile group is soluble in an aqueous alkaline solution, but when protected with an acid labile group becomes insoluble. Examples of monomers that impart alkali solubility are acrylic acid, methacrylic acid, vinyl alcohol, hydroxystyrenes, vinyl monomers containing 1,1',2,2',3,3'-hexafluoro-2-propanol and sulfonamides (e.g., 2-trifluoromethanesulfonylaminoethyl methacrylate and 2-sulfonylamino-2,2-difluoroethylmethacrylate), although any group that makes the polymer alkali soluble may be used. The hydrophilic functionalities can be protected with acid labile groups such as alkyl, cycloalkyl, substituted cycloalkyl, oxocyclohexyl, cyclic lactone, benzyl, silyl, alkyl silyl, substituted benzyl, alkoxy alkyl such as ethoxy ethyl or methoxy ethoxy ethyl, acetoxyalkoxy alkyl such as acetoxy ethoxy ethyl, tetrahydrofuranyl, menthyl, tetrahydropyranyl and mevalonic lactone. Examples acid labile groups include, but are not limited to, t-butoxycarbonyl, tricyclo(5.3.2.0)decanyl, 2-methyl-2-adamantyl, isobornyl, norbornyl, adamantyloxyethoxy ethyl, menthyl, tertiary butyl, tetrahydropyrany, 3-oxocyclohexyl, 3-hydroxy-1-adamantyl, 2-methyl-2-adamantyl, beta-(gamma-butyrolactonyl), and mevalonic lactone. Some of the monomers are vinyl compounds with the above mentioned labile groups. The acid labile group that can be cleaved with an acid may be attached to the polymer, which in the presence of an acid gives an alkali soluble polymer. The protected monomers may be polymerized to give homopolymers or with other unprotected monomers as required. Alternatively, an alkali soluble homopolymer or copolymer may be reacted with a compound, or compounds, which provide the acid labile group. When this polymer is used to form the antireflective coating composition, a dye as well as a photoacid generator will typically be present in the composition. This dye may be monomeric, polymeric or mixtures of both. Examples of absorbing groups that may be contained in an additive absorbing compound are substituted and unsubstituted phenyl, substituted and unsubstituted anthracyl, substituted and unsubstituted phenanthryl, substituted and unsubstituted naphthyl, substituted and unsubstituted heterocyclic rings containing heteroatoms such as oxygen, nitrogen, sulfur, or combinations thereof, such as pyrrolidinyl, pyranyl, piperidinyl, acridinyl, quinolinyl. Absorbing polymeric dyes that may be used are polymers of the absorbing moieties listed above, where the polymer backbone may be polyesters, polyimides, polysulfones and polycarbonates. Some dyes are copolymers of hydroxystyrene and methyl methacrylate and azo polymeric and monomeric dyes. Examples of dyes are monomers or polymers of the list of chromophores mentioned below.

Another polymer useful in positive bottom photoimageable antireflective coating compositions is (ii) a polymer comprising at least one unit with an acid labile group and at least one unit with an absorbing chromophore. A skilled artisan will appreciate which chromophores are useful at the exposure wavelength of interest. Examples of an absorbing chromophore are hydrocarbon aromatic moieties and heterocyclic aromatic moieties with from one to four separate or fused rings, where there are 3 to 10 atoms in each ring. Examples of monomers with absorbing chromophores that can be polymerized with the monomers containing the acid labile groups are vinyl compounds containing substituted and unsubstituted phenyl, substituted and unsubstituted anthracyl, substituted and unsubstituted phenanthryl, substituted and unsubstituted naphthyl, substituted and unsubstituted heterocyclic rings containing heteroatoms such as oxygen, nitrogen, sulfur, or combinations thereof, such as pyrrolidinyl, pyranyl, piperidinyl, acridinyl, quinolinyl. Other chromophores are described in U.S. Pat. No. 6,114,085, and in U.S. Pat. No. 5,652,297, U.S. Pat. No. 5,763,135, U.S. Pat. No. 5,981,145, U.S. Pat. No. 6,187,506, U.S. Pat. No. 5,939,236, and U.S. Pat. No. 5,935,760, which may also be used, and are incorporated herein by reference. Examples of the monomers include, for example, styrene, hydroxystyrene, acetoxystyrene, vinyl benzoate, vinyl 4-tert-butylbenzoate, ethylene glycol phenyl ether acrylate, phenoxypropyl acrylate, 2-(4-benzoyl-3-hydroxyphenoxy)ethyl acrylate, 2-hydroxy-3-phenoxypropyl acrylate, phenyl methacrylate, benzyl methacrylate, 9-anthracenylmethyl methacrylate, 9-vinylanthracene, 2-vinylnaphthalene, N-vinylphthalimide, N-(3-hydroxy)phenyl methacrylamide, N-(3-hydroxy-4-hydroxycarbonylphenylazo)phenyl methacrylamide, N-(3-hydroxyl-4-ethoxycarbonylphenylazo)phenyl methacrylamide, N-(2,4-dinitrophenylaminophenyl)maleimide, 3-(4-acetoaminophenyl)azo-4-hydroxystyrene, 3-(4-ethoxycarbonylphenyl)azo-acetoacetoxy ethyl methacrylate, 3-(4-hydroxyphenyl)azo-acetoacetoxy ethyl methacrylate, tetrahydroammonium sulfate salt of 3-(4-sulfophenyl)azoacetoacetoxy ethyl methacrylate and equivalent structures. Any chromphore that absorbs at the appropriate exposure wavelength may be used alone or in combination with other chromophores. Thus a polymer may be synthesized by polymerizing monomers that contain an acid labile group with monomers that contain an absorbing chromophore. Alternatively, the alkali soluble polymer may be reacted with compounds that provide the acid labile group and compounds that provide the absorbing chromophore. The mole % of the acid labile unit in the final polymer can range from 5 to 95, and the mole % of the absorbing chromophore unit in the final polymer can range from 5 to 95. Also the acid labile group is attached to the absorbing chromophore or that the chromophore is attached to the acid labile group, for example the monomers may be $CH_2=CHX—Ar—(CO)_nO—R$ (n=0-1), $CH_2=CHX—Ar—OC(O)O—R$, $(CH)=CHX—Ar—C(CF_3)_2O—R$, $CH_2=CHX—Ar—C(CF_3)_2O(CO)O—R$, $CH_2=CHX—Ar—C(CF_3)_2(COOR)$, $CH_2=CHX—C(O)O—Ar—OC(O)—R$, $CH_2=CHX—CON(X)—Ar—O—R$, and vinyl compounds containing —(CO)O—R—Ar, —OC(O)O—R—Ar, —C(CF_3)_2O—R—Ar, —C(CF_3)_2O(CO)O—R—Ar, $C(CF_3)_2(COOR—Ar)$, where X is H or alkyl, Ar is substituted and unsubstituted phenyl such as phenyl or benzyl, substituted and unsubstituted anthracyl such as anthracylmethyl, substituted and unsubstituted phenanthryl, substituted and unsubstituted naphthyl, substituted and unsubstituted heterocyclic aromatic rings containing heteroatoms such as oxygen, nitrogen, sulfur, or combinations thereof, such as pyrrolidinyl, pyranyl, piperidinyl, acridinyl, quinolinyl, and R is alkyl, cycloalkyl, substituted cycloalkyl, oxocyclohexyl, cyclic lactone, benzyl, substituted benzyl, alkoxy alkyl, such as ethoxy ethyl or methoxy ethoxy ethyl, acetoxy ethoxy ethyl, tetrahydrofuranyl, menthyl, tetrahydropyranyl, mevalonic lactone. Examples of R include, for example, t-butoxycarbonyl tricyclo(5.3.2.0)decanyl, 2-methyl-2-adamantol, isobornyl, norbornyl, adamantyloxyethoxy ethyl, menthyl, tertiary butyl, tetrahydropyranyl, 3-oxocyclohexyl.

In addition to the unit containing the acid labile group and the absorbing chromphore, the polymer may contain other nonabsorbing monomeric units, such units may provide other desirable properties. A skilled artisan will appreciate which nonabsorbing monomeric units can be useful at the exposure wavelength of interest. Examples of the third monomer include $—CR_1R_2—CR_3R_4—$, where $R_1$ to $R_4$ are independently H, $(C_1-C_{10})$alkyl, $(C_1-C_{10})$alkoxy, nitro, halide, cyano, alkylaryl, alkenyl, dicyanovinyl, $SO_2CF_3$, COOZ, $SO_3Z$, COZ, OZ, $NZ_2$, SZ, $SO_2Z$, NHCOZ, $SO_2NZ_2$, where Z is H, or $(C_1-C_{10})$alkyl, hydroxy$(C_1-C_{10})$alkyl, $(C_1-C_{10})$alkylOCOCH_2COCH_3, or $R_2$ and $R_4$ combine to form a cyclic group such as anhydride, pyridine, or pyrollidone, or $R_1$ to $R_3$ are independently H, $(C_1-C_{10})$alkyl, $(C_1-C_{10})$alkoxy and $R_4$ is a hydrophilic group. Examples of the hydrophilic group, are given here but are not limited to these: $O(CH_2)_2OH$, $O(CH_2)_{20}(CH_2)OH$, $(CH_2)_nOH$ (where n=0-4), $COO(C_1-C_4)$ alkyl, COOX and $SO_3X$ (where X is H, ammonium, alkyl ammonium). Other hydrophilic vinyl monomers that can be used to form the polymer are acrylic acid, methacrylic acid, vinyl alcohol, maleic anhydride, maleic acid, maleimide, N-methyl maleimide, N-hydroxymethyl acrylamide and N-vinyl pyrrolidinone. Other monomers may be methyl methacrylate, butyl methacrylate, hydroxyethyl methacrylate and hydroxypropyl methacrylate. Monomeric units containing acid labile groups may also be used, such as hydroxystyrene, vinyl alcohol, (meth)acrylic acid capped with acid labile groups. Examples of acid labile groups, without limitation, are secondary and tertiary alkyls (up to 20 carbon atoms) with at least one β hydrogen, acetals and ketals, trimethylsilyl, and β-trimethylsilyl substituted alkyls. Representative examples of acid labile groups are tert-butyl, tert-pentyl, isobornyl, 1-alkylcyclohexyl, 1-alkylcyclopentyl, cyclohexyl, 2-alkyl-2-adamantyl, 2-alkyl-2-norbornyl. Other examples of acid labile groups are tetrahydrofuranyl, tetrahydropyranyl, substituted or unsubstituted methoxycarbonyl, β-trialkylsilylalkyl groups (e.g. $CH_2—CH_2Si(CH_3)_3$, $CH(—CH_2Si(CH_3)_3)_2$, $CH_2—CH(Si(CH_3)_3)_2$) and the like.

Examples of monomers containing acid labile groups that can be used in the polymers include methacrylate ester of methyladamantane, methacrylate ester of mevalonic lactone, 3-hydroxy-1-adamantyl methacrylate, methacrylate ester of beta-hydroxy-gamma-butyrolactone, t-butyl norbornyl carboxylate, t-butyl methyl adamantyl methacrylate, methyl adamantyl acrylate, t-butyl acrylate and t-butyl methacrylate; t-butoxy carbonyl oxy vinyl benzene, benzyl oxy carbonyl oxy vinyl benzene; ethoxy ethyl oxy vinyl benzene; trimethyl silyl ether of vinyl phenol, and 2-tris(trimethylsilyl)silyl ethyl ester of methyl methacrylate.

The monomers containing an absorbing chromophore include triphenylphenol, 2-hydroxyfluorene, 9-anthracenemethanol, 2-methylphenanthrene, 2-naphthalene ethanol, 2-naphthyl-beta-d-galactopyranoside hydride, hydroxystyrene, styrene, acetoxystyrene, benzyl methacrylate, N-methyl maleimide, vinyl benzoate, vinyl 4-tert-butylbenzoate, ethylene glycol phenyl ether acrylate, phenoxypropyl acrylate, benzyl mevalonic lactone ester of maleic acid, 2-hydroxy-3-phenoxypropyl acrylate, phenyl methacrylate, benzyl methacrylate, 9-anthracenylmethyl methacrylate, 9-vinylanthracene, 2-vinylnaphthalene, N-vinylphthalimide, N-(3-hydroxy)phenyl methacrylamide, N-(3-hydroxy-4-hydroxycarbonylphenylazo)phenyl methacrylamide, N-(3-hydroxyl-4-ethoxycarbonylphenylazo)phenyl methacrylamide, N-(2,4-dinitrophenylaminophenyl)maleimide, 3-(4-acetoaminophenyl)azo-4-hydroxystyrene, 3-(4-ethoxycarbonylphenyl)azo-acetoacetoxy ethyl methacrylate, 3-(4-hydroxyphenyl)azo-acetoacetoxy ethyl methacrylate, tetrahydroammonium sulfate salt of 3-(4-sulfophenyl)azoacetoacetoxy ethyl methacrylate. A skilled artisan will appreciate which chromophores are useful at the exposure wavelength of interest.

The polymer containing the acid labile unit may also contain other nonabsorbing monomeric units as described above. Examples of the polymer containing the acid labile group include copolymers of 2-methyl-2-adamantyl methacrylate, mevalonic lactone methacrylate, 3-hydroxy-1-adamantyl methacrylate, methacrylate ester of beta-hydroxy-gamma-butyrolactone, t-butyl norbornyl carboxylate, t-butyl methyl adamantyl methacrylate, methyl adamantyl acrylate, t-butyl acrylate and t-butyl methacrylate; t-butoxy carbonyl oxy vinyl benzene, benzyl oxy carbonyl oxy vinyl benzene; ethoxy ethyl oxy vinyl benzene; trimethyl silyl ether of vinyl phenol, and 2-tris(trimethylsilyl)silyl ethyl ester of methyl methacrylate, with methyl methacrylate, butyl methacrylate, acrylic acid, methacrylic acid, vinyl alcohol, maleic anhydride, N-vinyl pyrrolidinone, maleimide, N-methyl maleimide, and the like.

Yet another polymer useful for the positive bottom photo-imageable antireflective coating compositions is (iii) a polymer that comprises at least one unit with hydroxyl and/or carboxyl group and at least one unit with an absorbing chromophore. Examples of an absorbing chromophore are described hereinabove.

For the polymer comprising at least one unit with a hydroxyl and/or a carboxyl group to provide alkaline solubility, and a crosslinking site, one function of the polymer is to provide a good coating quality and another is to enable the antireflective coating to change solubility during the imaging process. The hydroxyl or carboxyl groups in the polymer provide one of the components necessary for the solubility change. Examples of monomers which provide such a unit upon polymerization are without limitations, substituted or unsubstituted vinyl monomers containing a hydroxyl and or carboxyl group, such as acrylic acid, methacrylic acid, vinyl alcohol, hydroxystyrenes, hydroxyethyl methacrylate, hydroxypropyl methacrylate, N-(hydroxymethyl)acrylamide, 4-hydroxyphenyloxy methacrylate, 4-hydroxyphenyloxy acrylate, 5-hydroxynaphthyloxy methacrylate, 5-hydroxynaphthyloxy acrylate, vinyl monomers containing 1,1',2,2',3,3'-hexafluoro-2-propanol, although any monomer that makes the polymer alkali soluble and preferably water insoluble, may be used. The polymer may contain a mixture of monomer units containing hydroxyl and/or carboxyl groups. Vinyl monomers containing the 1,1,1,3,3,3-hexafluoro-2-propanol group are represented by structures (1) to (6) and their substituted equivalents.

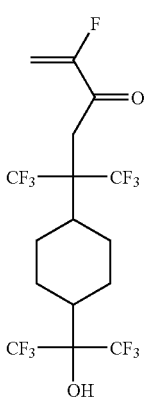

(1)

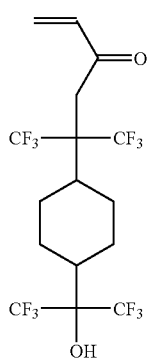

(2)

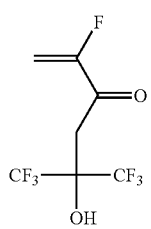

(3)

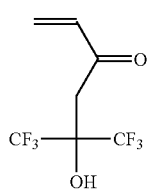

(4)

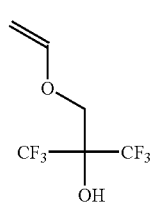

(5)

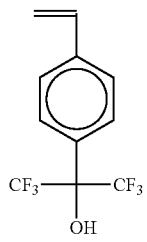

(6)

Thus a polymer may be synthesized by polymerizing monomers that contain a hydroxyl or carboxyl group with monomers that contain an absorbing chromophore. A skilled artisan will appreciate which chromophores are useful at the exposure wavelength of interest. Alternatively, the alkali soluble polymer may be reacted with compounds that provide the hydroxyl or carboxyl group and compounds that provide the absorbing chromophore. In the final polymer the mole % of the unit or units containing the hydroxyl or carboxyl group can range from 5 to 95, preferably 10 to 90, and more preferably 20 to 80 and the mole % of the absorbing chromophore unit in the final polymer can range from 5 to 95, preferably 10 to 90 more preferably 20 to 80. It is also within the scope of this invention that the hydroxyl or carboxyl group is attached to the absorbing chromophore or that the chromophore is attached to the hydroxyl or carboxyl group, that is, both groups are present in the same unit. As an example the chromophoric groups described previously may have pendant hydroxyl and/or carboxyl groups or that the chromophoric groups and the hydroxyl group and/or carbonyl group are attached to the same group.

In addition to the unit containing the hydroxyl and/or carboxyl group and the unit containing the absorbing chromophore, the polymer may contain other monomeric units, such units may provide other desirable properties, examples of which are described hererinabove.

Examples of the foregoing polymers include, for example,

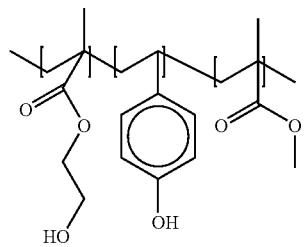

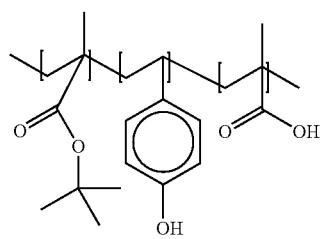

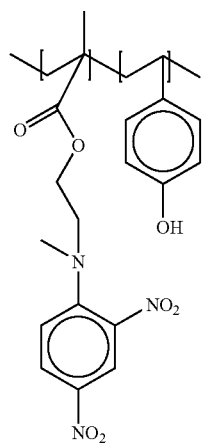

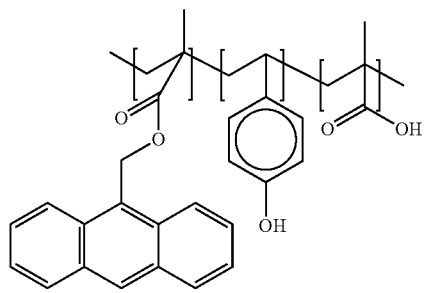

-continued

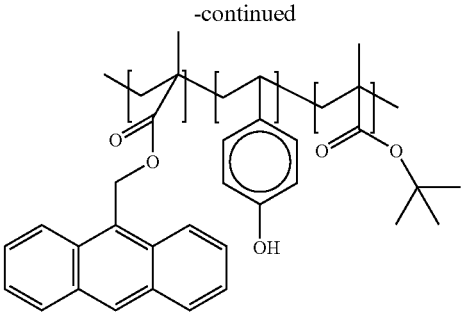

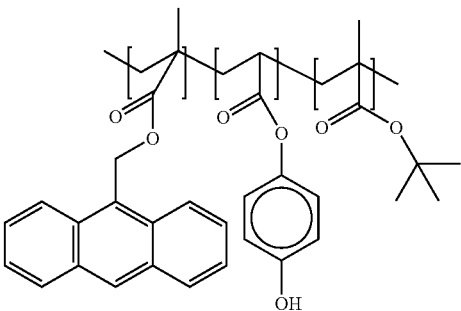

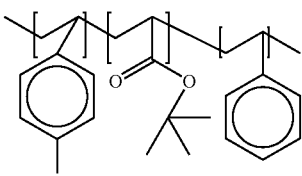

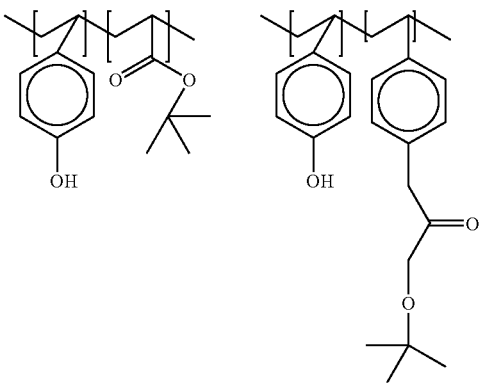

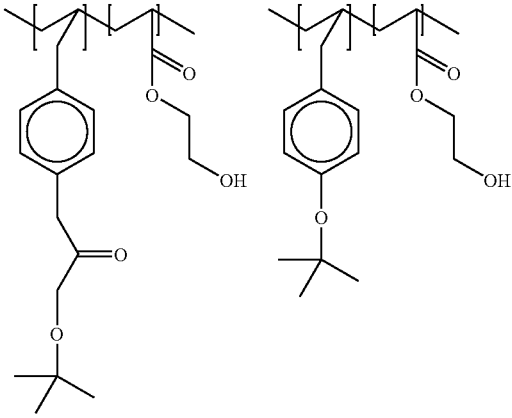

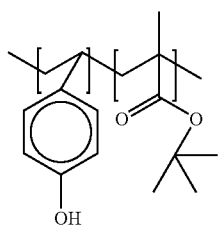
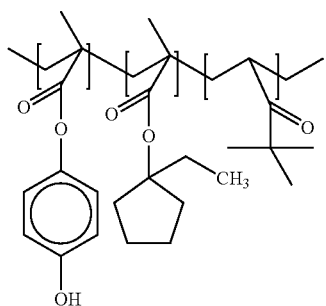
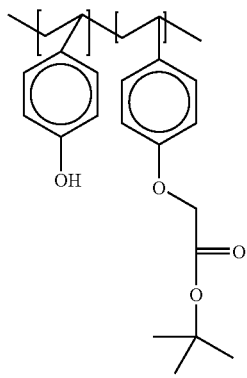
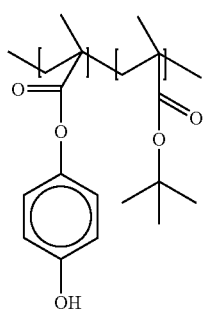

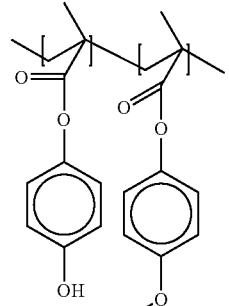
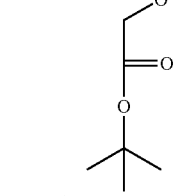
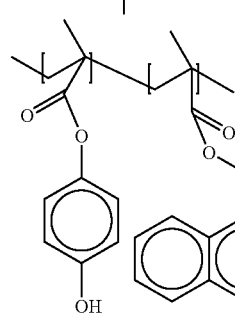
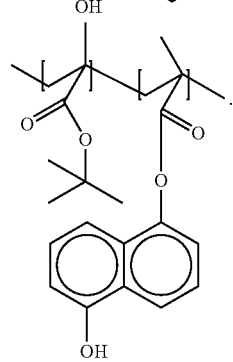

See also United States Published Patent Applications 20030129531 and 20050214674, the contents of which are hereby incorporated by reference herein. "A catenary heteroatom" refers to an internal heteroatom such as for example nitrogen, oxygen, or sulfur, bonded between carbon atoms. Preferred heteroatoms are nitrogen or oxygen. These heteroatoms may interrupt the chain of an aliphatic or cycloaliphatic hydrocarbon.

When polymers having the hydroxyl and/or carboxyl group are used, an optional crosslinking agent can be added thereto. One example includes vinyl ether terminated crosslinking agents that can be represented by the general structure (7):

$$R^1-(OCH=CH_2)_n \qquad (7)$$

wherein $R^1$ is selected from ($C_1$-$C_{30}$) linear, branched or cyclic alkyl, substituted or unsubstituted ($C_6$-$C_{40}$)aryl, or substituted or unsubstituted ($C_7$-$C_{40}$)alicyclic hydrocarbon; and $n \geq 2$. It is believed that the terminal vinyl ether group reacts with the hydroxyl or carboxyl group of the polymer to give an acid labile acetal linkage. Examples of such vinyl ether terminated crosslinking agents include bis(4-vinyloxy butyl)adipate; bis(4-vinyloxy butyl)succinate; bis(4-vinyloxy butyl)isophathalate; bis(4-vinyloxymethyl cyclohexylmethyl)glutarate; tris(4-vinyloxy butyl)trimellitate; bis(4-vinyloxy methyl cyclohexyl methyl)terephthalate; bis(4-vinyloxy methyl cyclohexyl methyl)isophthalate; bis(4-vinyloxy butyl)(4-methyl-1,3-phenylene)biscarbamate; bis(4-vinyloxy butyl)(methylene di-4,1-phenylene) biscarbamate; and triethyleneglycol divinylether, 1,4-cyclohexanedimentanol divinyl ether, various vinyl ether monomers available under the tradename Vectomer, such as, for example, 4-(vinyloxy)butyl benzoate, bis[4-(vinyloxy) butyl]adipate, bis[4-(vinyloxy)butyl]succinate, 4-(vinyloxymethyl)cyclohexylmethyl benzoate, bis[4-(vinyloxy)butyl]isophthalate, bis[4-(vinyloxymethyl)cyclohexylmethyl] glutarate, tris[4-(vinyloxy)butyl]trimellitate, 4-(vinyloxy) butyl stearate, bis[4-(vinyloxy)butyl] hexanediylbiscarbamate, bis[[4-[(vinyloxy)methyl] cyclohexyl]methyl]terephthalate, bis[[4-[(vinyloxy)methyl] cyclohexyl]methyl]isophthalate, bis[4-(vinyloxy)butyl] (methylenedi-4,1-phenylene)biscarbamate, bis[4-(vinyloxy) butyl](4-methyl-1,3-phenylene)biscarbamate, and polymers bearing pendant vinyloxy groups. Other vinyl ether terminated crosslinking agents are described in T. Yamaoka, et al., Trends in Photochem. Photobio., 7:45 (2001); S. Moon, et al., Chem. Mater., 6:1854 (1994); or H. Schacht, et al., ACS Symp. Ser. 706:78 (1998) which may also be used, and are incorporated herein by reference.

When used, the vinyl ether terminated crosslinking agent is added to the antireflective coating in a proportion which provides 0.20-2.00 mol equivalents of vinyl ether crosslinking function per reactive group on the polymer, further 0.50-1.50 reactive equivalents per reactive group.

The inventive composition and inventive compounds can also be used in traditional antireflective coating compositions. Traditional antireflective coating compositions typically contain polymers, a dye or chromophore component which in some cases can be part of the polymer, a crosslinking component which can be optional when using the inventive compounds, and an acid source. The acid source and dye or chromophore component are discussed herein. Crosslinking components include, but are not limited to, melamines, guanamines, hydroxy alkyl amides, epoxy and epoxy amine resins, blocked isocyanates, and divinyl monomers, and the like. Traditional antireflective coating compositions, when used, are coated on a wafer and then overcoated with a photoresist, and then the coated is exposed and developed. The antireflective coating in the exposed area is then etched, with the resist pattern being transferred to the substrate.

The compositions of the present invention may further comprise an acid or a thermal acid generator. Crosslinking can take place between a polymer containing a hydroxyl and/or carboxyl group and a crosslinking agent in the presence of heat, however, typically reaction times may be long. Thermal acid generators or acids are used to accelerate the crosslinking reaction and are desirable for instances where short curing times are preferred. Thermal acid generators liberate the acid upon heating. Any known acids or thermal acid generators may be used, exemplified without limitations, by 2,4,4,6-tetrabromocyclohexadienone, benzoin tosylate, squaric acid, 2-nitrobenzyl tosylate, chloroacetic acid, toluenesulfonic acid, methanesulfonic acid, nonaflate acid, triflic acid, other alkyl esters of organic sulfonic acids, salts of these mentioned acids. However, it has been found that for certain components some acids and acids produced by thermal acid generators, which have high acidity, can lead to undercutting and can prevent the desired photoimaging process from taking place.

Acids with moderate acidity, i.e. with a pKa ($-\log_{10}$ of the acid dissociation constant) greater than 1.0 are of interest when used with a vinyl terminated crosslinking agent and/or the vinyl terminated PAG or Q (for example, formulae (2) and (4) herein). Acids with a pKa of less than 5.0 and greater than 1.0 are also of further interest. The resulting acetal linkages are easily cleavable in the presence of photogenerated acids. Examples, without limitations, of acids or acids derived from thermal acid generators with moderate acidity are maleic acid (pKa of 1.83), chloroacetic acid (pKa of 1.4), dichloroacetic acid (pKa of 1.48), oxalic acid (pKa of 1.3), cinnamic acid (pKa of 4.45), tartaric acid (pKa of 4.3), gylcolic acid (pKa of 3.8), fumaric acid (pKa of 4.45), malonic acid (pKa of 2.8), cyanoacetic acid (pKa of 2.7), etc.

Acids which are blocked by bases to form a thermal acid generator are preferred. Acids, such as those described above, may be blocked with bases such as amines. Typical bases are triethyl amine, tripropyl amine, trimethyl amine, tributyl amine, tripentyl amine, tridodecyl amine etc. Additionally, diaryl or trialkyl sulfonium salts with anions of weak acids, such as carboxylic acid or aryl carboxylic acid may be used. Acids which are blocked by bases may be formed by combining the acid with a base, where the acid:base ratio ranges from about 1:1 to about 1:3. Further examples of acids with the desired pKa and their salts can be found by one of ordinary skill in the art by reviewing the available literature, such as in CRC Handbook of Chemistry and Physics, published by CRC Press Inc. and incorporated herein by reference. In some embodiments it may also be desirable that the thermal acid be such that once the acid is generated it does not remain permanently in the coating and therefore does not facilitate the reverse reaction, but is removed from the film. It is believed that, once crosslinking takes place the acid is decomposed or volatilized by heat and the decomposition products are baked out of the film, or the acid may sublime from the coating. Thus none or very little of the free acid remains in the film after curing, and the reverse reaction causing the decomposition of the acetal linkage does not take place. Thermal acid generators which can generate an acid and then be removed prior to coating of the photoresist are preferred in some cases. Weak acids that remain in the film may also be functional, as they may not greatly hinder the decomposition of the acetal linkage. The amines used are typically volatile ones, the use of which providing significant benefits in that the amine can be removed (volatized) from the antireflective composition coating layer during thermal curing of that layer.

Other examples include a mono functionalized ammonium salts of dicarboxylic acid has the general formula

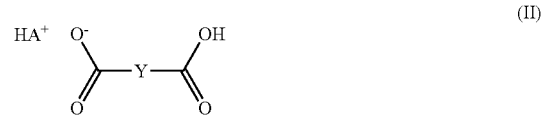

(II)

where Y is selected from a direct bond and a connecting group; and A is an unsubstituted or substituted amine compound.

The connecting group Y can be selected from $C_1$-$C_8$ unsubstituted or substituted alkylene chain optionally containing one or more hetero atoms (for example, O, S, SO, $SO_2$, —C(=O)—, —C(=O)O—, —O—C(=O)—O—, —OC(=O)—, $C_3$-$C_8$ unsubstituted or substituted cycloalkylene, $C_2$-$C_8$ unsubstituted or substituted alkenylene, and $C_6$-$C_{12}$ unsubstituted or substituted arylene. Furthermore, it can be $C_1$-$C_8$ unsubstituted or substituted alkylene chain optionally containing one or more hetero atoms, even still, $C_1$-$C_8$ unsubstituted or substituted alkylene chain optionally containing one or more O atoms, and yet even still $C_1$-$C_8$ unsubstituted or substituted alkylene chain (for example, unsubstituted or substituted methylene; unsubstituted or substituted ethylene; or unsubstituted or substituted propylene), $C_1$-$C_3$ unsubstituted or substituted alkylene chain, or even $C_1$-$C_3$ alkylene chain substituted with hydroxyl and/or alkyl.

The amine compound can be selected such that it volatizes at a temperature at which compositions which contain the compound of formula (II) are baked. Examples of the amine compound include a compound selected from the group consisting of

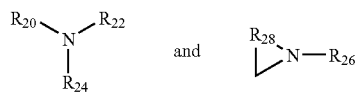

where each of $R_{20}$, $R_{22}$, $R_{24}$, and $R_{26}$ are individually selected from hydrogen, unsubstituted or substituted alkyl, unsubstituted or substituted cycloalkyl, unsubstituted or substituted monocyclic or polycyclic aryl, and unsubstituted or substituted aralkyl; and $R_{28}$ is selected from $C_3$-$C_7$ unsubstituted or substituted alkylene or $R_{28}$ together with the atoms to which it is bound forms a $C_6$-$C_{12}$ unsubstituted or substituted monocyclic or polycyclic aryl. Further examples include ammonia, unsubstituted and substituted trialkylamines, unsubstituted and substituted dialkylamines, and unsubstituted and substituted monoalkylamines, unsubstituted and substituted tricycloalkylamines, unsubstituted and substituted dicycloalkylamines, and unsubstituted and substituted monocycloalkylamines, unsubstituted and substituted monocylcoalkyldialkylamines, unsubstituted and substituted dicycloalkylmonoalkylamines, unsubstituted and substituted monoaryldialkylamines, unsubstituted and substituted diarylmonoalkylamines, unsubstituted and substituted triarylamines, unsubstituted and substituted diarylamines, and unsubstituted and substituted monoaryamines, unsubstituted and substituted triaralkylamines, unsubstituted and substituted diaralkylamines, and unsubstituted and substituted monoaralkylamines, unsubstituted and substituted monoaralkyldialkylamines, unsubstituted and substituted diaralkylmonoalkylamines, unsubstituted and substituted monoarylmonoalkylamines, unsubstituted and substituted monoarallkylmonoalkylamines, unsubstituted and substituted monocycloalkylmonoalkylamines, and unsubstituted and substituted monoarylmonocycloalkylamines and the like, etc. Further examples include trimethylamine, dimethylethylamine, dimethylpropylamine, dimethylbutylamine, methyldiethylamine, methyldipropylamine, methyldibutylamine, methylethylpropylamine, methylethylbutylamine, methylpropylbutylamine, triethylamine, ethyldipropylamine, ethyldibutylamine, diethylpropylamine, diethylbutylamine, ethylpropylbutylamine, tripropylamine, dipropylbutylamine, propyldibutylamine, tributylamine, pyrrolidine, piperidine, piperazine, cyclohexyl amine, and the like, etc.

The acid or acid derived from the thermal acid generator is preferably removed from the antireflective coating (decomposes) at a temperature ranging from about 115° C. to about 220° C., further from 120° C. to about 200° C.

As used herein, alkyl means methyl, ethyl, propyl (n-propyl, i-propyl), butyl (n-butyl, i-butyl, sec-butyl, t-butyl), pentyl (and its isomers), hexyl (and its isomers), heptyl (and its isomers), octyl (and its isomers), and the like. The cycloalkyls include cyclohexyl, menthyl and the like. The alkenyls include allyl, vinyl and the like. The aryl groups include monocyclic or polycyclic rings such as, for example, phenyl, naphthyl and the like. The aralkyl groups include phenylmethyl (i.e., benzyl), phenylethyl (i.e., phenethyl) and the like. Alkylene, cycloalkylene, and arylene mean the same as above for alkyl, cycloalkyl, and aryl except that an additional hydrogen atom has been removed from the alkyl, cycloalkyl or aryl (for example, ethylene, propylene, cyclohexylene, phenylene, etc). The term heteroarylene refers to a arylene having one or more carbon atoms replaced with a heteroatom (for example, S, O, or N).

The solvent for the antireflective coating is chosen such that it can dissolve all the solid components of the antireflective coating, and also can be removed during the bake step so that the resulting coating is not soluble in the coating solvent of the photoresist. Furthermore, to retain the integrity of the antireflective coating, the polymer of the antireflective coating, as well as the photoacid generator, is substantially insoluble in the solvent of the top photoresist. Such requirements prevent, or minimize, intermixing of the antireflecting coating layer with the photoresist layer. Typically propylene glycol monomethyl ether acetate and ethyl lactate are the preferred solvents for the top photoresist. Examples of suitable solvents for the antireflective coating composition are cyclohexanone, cyclopentanone, anisole, 2-heptanone, ethyl lactate, propylene glycol monomethyl ether, butyl acetate, gamma butyroacetate, ethyl cellosolve acetate, methyl cellosolve acetate, methyl 3-methoxypropionate, ethyl pyruvate, 2-methoxybutyl acetate, 2-methoxyethyl ether, but ethyl lactate, propylene glycol monomethyl ether acetate, propylene glycol monomethyl ether or mixtures thereof are preferred. Solvents with a lower degree of toxicity and good coating and solubility properties are generally preferred.

Typical antireflective coating compositions may comprise up to about 15 percent by weight of the solids, preferably less than 8 percent, based on the total weight of the coating composition. The solids may comprise from 0.01 to 25 weight percent of the photoacid generator, 50 to 99 weight percent of polymer, 1 to 50 weight percent of the crosslinking agent and optionally 0 to 25 weight percent of the acid or thermal acid generator, based on the total solids content of the antireflective coating composition. Preferably the photoacid generator level ranges from about 0.1 to about 20 weight %. Preferably the crosslinking agent ranges from about 5 to about 40 weight percent, more preferably 10 to 35 weight percent. The solid components are dissolved in the solvent, or mixtures of solvents, and filtered to remove impurities. The antireflective coating composition can optionally contain surfactants, base quencher, and other similar materials. The components of the antireflective coating may also be treated by techniques such as passing through an ion exchange column, filtration, and extraction process, to improve the quality of the product.

Other components may be added to the antireflective composition of the present application in order to enhance the performance of the coating, e.g. lower alcohols, dyes, surface leveling agents, adhesion promoters, antifoaming agents, etc. These additives may be present at up to 30 weight percent level. Other polymers, such as, novolaks, polyhydroxystyrene, polymethylmethacrylate and polyarylates, may be added to the composition, providing the performance is not negatively impacted. Preferably the amount of this polymer is kept below 50 weight % of the total solids of the composition, more preferably 35 weight %, and even more preferably below 20 weight %. Non-volatile bases may also be added to the composition to limit diffusion. Both non-volatile bases and non-volatile photodecomposable bases are known additives. Examples of non-volatile bases include ammonium hydroxide, tetrabutylammonium hydroxide, triethanolamine, diethanol amine, trioctylamine, n-octylamine, and trimethylsulfonium hydroxide. Examples of non-volatile photodecomposable bases include triphenylsulfonium hydroxide, bis(t-butylphenyl)iodonium cyclamate and tris(tert-butylphenyl) sulfonium cyclamate. Another component of the antireflective coating composition is a volatile amine, which is beneficial in enhancing the stability of the composition during storage and use. Suitable volatile amines are those which have a boiling point equal to or less than the solvent used in the antireflective coating composition. Examples of volatile amines include triethylamine, tributylamine, dibutylamine, diethylamine, monobutylamine, monoethylamine, aniline, substituted anilines, and the like, etc.

The absorption parameter (k) of the novel composition ranges from about 0.1 to about 1.0, preferably from about 0.15 to about 0.7 as measured using ellipsometry. The refractive index (n) of the antireflective coating is also optimized. The n and k values can be calculated using an ellipsometer, such as the J. A. Woollam WVASE VU-302 TM Ellipsometer. The exact values of the optimum ranges for k and n are dependent on the exposure wavelength used and the type of application. Typically for 193 nm the preferred range for k is 0.1 to 0.75, for 248 nm the preferred range for k is 0.15 to 0.8, and for 365 nm the preferred range is from 0.1 to 0.8. The thickness of the antireflective coating is less than the thickness of the top photoresist. Preferably the film thickness of the antireflective coating is less than the value of (wavelength of exposure/refractive index), and more preferably it is less than the value of (wavelength of exposure/2 times refractive index), where the refractive index is that of the antireflective coating and can be measured with an ellipsometer. The optimum film thickness of the antireflective coating is determined by the exposure wavelength, refractive indices of the antireflective coating and of the photoresist, absorption characteristics of the top and bottom coatings, and optical characteristics of the substrate. Since the bottom antireflective coating must be removed by exposure and development steps, the optimum film thickness is determined by avoiding the optical nodes where no light absorption is present in the antireflective coating. For 193 nm a film thickness of less than 55 nm is preferred, for 248 nm a film thickness of less than 80 nm is preferred and for 365 nm a film thickness of less than 110 nm is preferred.

The antireflective coating composition is coated on the substrate using techniques well known to those skilled in the art, such as dipping, spin coating or spraying. Various substrates known in the art may be used, such as those that are planar, have topography or have holes. Examples of semiconductor substrates are crystalline and polycrystalline silicon, silicon dioxide, silicon (oxy)nitride, aluminum, aluminum/silicon alloys, and tungsten. In certain cases there can be a buildup of photoresist film at the edges of the substrate, referred to as edge bead. This edge bead can be removed using a solvent or mixture of solvents using techniques well known to those of ordinary skill in the art. The coating is then cured. The preferred range of temperature is from about 40° C. to about 240° C. for about 30-120 seconds on a hot plate or equivalent heating unit, more preferably from about 100° C. to about 200° C. for 45-90 seconds. The film thickness of the antireflective coating ranges from about 20 nm to about 300 nm. The optimum film thickness is determined, as is well known in the art, to be where good lithographic properties are obtained, especially where no standing waves are observed in the photoresist. The cured antireflective coating is also insoluble at this stage in the alkaline developing solution. The photoresist can then be coated on top of the antireflective coating.

Positive photoresists, which are developed with aqueous alkaline solutions, are useful for the present invention, provided the photoactive compounds in the photoresist and the antireflective coating absorb at the same exposure wavelength used for the imaging process for the photoresist. Positive-working photoresist compositions are exposed image-wise to radiation, those areas of the photoresist composition exposed to the radiation become more soluble to the developer solution (e.g. a rearrangement reaction occurs) while those areas not exposed remain relatively insoluble to the developer solution. Thus, treatment of an exposed positive-working photoresist with the developer causes removal of the exposed areas of the coating and the formation of a positive image in the photoresist coating. Photoresist resolution is defined as the smallest feature which the resist composition can transfer from the photomask to the substrate with a high degree of image edge acuity after exposure and development. In many manufacturing applications today, resist resolution on the order of less than one micron are necessary. In addition, it is almost always desirable that the developed photoresist wall profiles be near vertical relative to the substrate. Such demarcations between developed and undeveloped areas of the resist coating translate into accurate pattern transfer of the mask image onto the substrate. This becomes even more critical as the drive toward miniaturization reduces the critical dimensions on the devices.

Positive-acting photoresists comprising novolak resins and quinone-diazide compounds as photoactive compounds are well known in the art. Novolak resins are typically produced by condensing formaldehyde and one or more multi-substituted phenols, in the presence of an acid catalyst, such as oxalic acid. Photoactive compounds are generally obtained by reacting multihydroxyphenolic compounds with naphthoquinone diazide acids or their derivatives. The sensitivity of these types of resists typically ranges from about 300 nm to 440 nm.

Photoresist resolution is defined as the smallest feature, which the photoresist composition can transfer from the photomask to the substrate with a high degree of image edge acuity after exposure and development. In many manufacturing applications today, photoresist resolution on the order of less than one micron are necessary. In addition, it is almost always desirable that the developed photoresist wall profiles be near vertical relative to the substrate. Such demarcations between developed and undeveloped areas of the resist coating translate into accurate pattern transfer of the mask image onto the substrate. This becomes even more critical as the drive toward miniaturization reduces the critical dimensions on the devices.

Photoresists sensitive to short wavelengths, between about 180 nm and about 300 nm can also be used. Examples of such photoresists are given in the following patents and incorporated herein by reference, U.S. Pat. No. 4,491,628, U.S. Pat. No. 5,350,660, U.S. Pat. No. 5,069,997, EP 794458 and GB 2320718. Photoresists for 248 nm normally comprise polyhydroxystyrene or substituted polyhydroxystyrene derivatives, a photoactive compound, and optionally a solubility inhibitor. Particularly preferred for 193 nm and 157 nm exposure are photoresists comprising non-aromatic polymers, a photoacid generator, optionally a solubility inhibitor, and solvent. Photoresists sensitive at 193 nm that are known in the prior art are described in the following documents and incorporated herein, WO 97/33198, U.S. Pat. No. 5,585,219, Proc. SPIE, vols. 3333 (1998), 3678 (1999), 3999 (2000), 4345

(2001). Particularly preferred for 193 nm and 157 nm exposure are photoresists comprising non-aromatic polymers, a photoacid generator, optionally a solubility inhibitor, and solvent. Photoresists sensitive at 193 nm that are known in the prior art are described in the following references and incorporated herein, Proc. SPIE, vols. 3999 (2000), 4345 (2001), although any photoresist sensitive at 193 nm may be used on top of the antireflective composition herein.

In positive systems, a film of photoresist is then coated on top of the cured antireflective coating and baked to substantially remove the photoresist solvent. The photoresist and the antireflective coating bilevel layers are then imagewise exposed to actinic radiation. In a subsequent heating step the acid generated during exposure step reacts to de-crosslink the polymer of the antireflective coating composition and thus rendering the exposed region of the antireflective coating alkali soluble in the developing solution. The temperature for the postexposure bake step can range from 40° C. to 200° C. for 30-200 seconds on a hot plate or equivalent heating system, preferably from 80° C. to 160° C. for 40-90 seconds. In some instances, it is possible to avoid the postexposure bake, since for certain chemistries, such as some acetal acid labile linkages, deprotection proceeds at room temperature. The polymer in the exposed regions of the antireflective coating is now soluble in an aqueous alkaline solution. The bilevel system is then developed with an aqueous alkaline developer to remove the photoresist and the antireflective coating. The developer is preferably an aqueous alkaline solution comprising, for example, tetramethyl ammonium hydroxide. The developer may further comprise additives, such as surfactants, polymers, isopropanol, ethanol, etc. The process of coating and imaging photoresist coatings and antireflective coatings is well known to those skilled in the art and is optimized for the specific type of photoresist and antireflective coating combination used. The imaged bilevel system can then be processed further as required by the manufacturing process of integrated circuits, for example metal deposition and etching.

In a multilayer system, for example, a trilayer system, or process, the trilayer process is wear, for example, an organic film is formed on a substrate, an antireflection film is formed on the organic film, and a photoresist film is formed on the antireflection film. An organic film is formed on a substrate as a lower resist film by spin coating method, etc. The organic film may or may not be then crosslinked with heat or acid after application by spin coating method etc. On the organic film is formed the antireflection film, for example that which is disclosed herein, as an intermediate resist film. After applying the antireflection film composition to the organic film by spin-coating etc., an organic solvent is evaporated, and baking is carried out in order to promote crosslinking reaction to prevent the antireflection film from intermixing with an overlying photoresist film. After the antireflection film is formed, the photoresist film is formed thereon as an upper resist film. Spin coating method can be used for forming the photoresist film as with forming the antireflection film. After photoresist film composition is applied by spin-coating method etc., prebaking is carried out. After that, a pattern circuit area is exposed, and post exposure baking (PEB) and development with a developer are carried out to obtain a resist pattern.

In other instances, the inventive coating composition is first coated on a substrate and then a second coating composition is coated there over and the layered system is cured by heating. Additionally, a coating composition is first coated on a substrate and then the inventive coating composition is coated over the first coating. Another coating composition can be coated over the inventive coating composition if needed. The coating compositions can be applied using various methods known in the art such as spin coating, spray coating, curtain coating, etc. The compositions can be cured by heating at temperatures from about 40° C. to about 250° C. The coating compositions used with the inventive coating composition can be based on acid curable resin compositions mentioned above.

Another instance is where an antireflective coating composition is formed from just

$$\text{PAG-(-L-OH)}_p \qquad (1)$$

$$\text{PAG-(-L-OCH=CH}_2)_p \qquad (2)$$

or
(a2) at least one compound of formula (5)

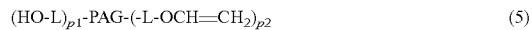

$$(\text{HO-L})_{p1}\text{-PAG-(-L-OCH=CH}_2)_{p2} \qquad (5)$$

and
(b) a solvent,
where PAG is a photoacid generator, each L is a direct bond or a linking group; p is an integer 1 to 12; p1 and p2 are each greater than or equal to 1 and p1+p2 equal 2 to 12.

In this instance, the PAG would also act as a chromophore. As such, the PAG would contain a moiety which functions as a chromophore, absorbing exposure radiation at the desired wavelength, for example, 248 nm, 193 nm, and the like. Those in the art will appreciate what type of moieties absorb radiation at those wavelengths. For example, a phenyl moiety will absorb at 193 nm; anthracene will absorb at 248 nm.

The inventive composition can also be used in a descumming process. A substrate, for example, $SiO_2$ or $SiON$ or a substrate coated with a conventional antireflective coating is coated with a thin (~10 nm) coating the inventive composition containing PAG. Then, a photoresist is then coated over then thin layer of inventive composition. The coated wafer is then exposed and developed. By using the inventive composition in this manner, redeposition of the organic material within the developer ('blob deposition') and/or footing caused by base contaminates from the substrate can be minimized. Additionally, the inventive PAG compounds can also be used in conventional anti-reflective coating compositions to reduce footing. When undercutting is an issue in a conventional anti-reflective coating, the inventive Q (quencher) compounds can be used to reduce undercutting.

The following specific examples will provide detailed illustrations of the methods of producing and utilizing compositions of the present invention. These examples are not intended, however, to limit or restrict the scope of the invention in any way and should not be construed as providing conditions, parameters or values which must be utilized exclusively in order to practice the present invention.

Each of the documents referred to above are incorporated herein by reference in its entirety, for all purposes. The following specific examples will provide detailed illustrations of the methods of producing and utilizing compositions of the present invention. These examples are not intended, however, to limit or restrict the scope of the invention in any way and should not be construed as providing conditions, parameters or values which must be utilized exclusively in order to practice the present invention. Except where noted, reagents were obtained from Sigma-Aldrich.

Example 1

Preparation of
Bis(4-hydroxyphenyl)Phenylsulfonium Nonaflate
(BHPPSNF)

Bis(4-hydroxyphenyl)phenylsulfonium triflate (2.5 g, 0.00739 moles; Dainippon Pharmaceuticals) was dissolved in 20 mL of water in a suitable container to which was added potassium nonaflate (3.28 g, 0.00739 mole). To this mixture was added 120 mL of water, which formed a cloudy solution. This solution was stirred overnight at room temperature in a stoppered flask. The formed oil was separated from the aqueous layer by decanting this layer away. The residual oil was washed with 2 mL of distilled water. This residue was dissolved in 4 mL acetone and another 2.6 g of potassium nonaflate and 100 mL of water. This mixture was then extracted with 100 mL of methylene chloride after stirring overnight. The methylene chloride layer was washed with water several times and stripped of solvents. Dissolving in a minimum of methylene chloride the residue was precipitated with pentane and then dried under high vacuum to give 2.68 g of white solid (61% yield) which was pure by $^1$H and $^{19}$F NMR.

Example 2

Preparation of Bis(Bis(4-hydroxyphenyl)Phenylsulfonium) 1,4-perfluorobutanedisulfonate (BHPPSFBDS)

Bis(4-hydroxyphenyl)phenylsulfonium triflate (2.5 g, 0.00570 mole) was dissolved in 25 mL of acetone in a suitable container to which was added while stirring a solution consisting of di-potassium 1,4-perfluorobutanedisulfonate (4.07 g, 0.0114 mole; 3M). A clear solution was obtained upon stirring. To this solution was added 100 mL of methylene chloride. After overnight stirring, crystals formed in the solution. The crystals were filtered and washed subsequently with distilled water and methylene chloride. The crystals obtained were then exchanged a second time with another aliquot of dipotassium 1,4-perfluorobutanesulfonate as described above. This resulted in 2.17 g of white solid (40% yield) which was pure material free of triflate as seen by $^{19}$F NMR and otherwise pure of other impurities as seen by $^1$H NMR.

Example 3

Preparation of Bis(4-vinyloxyethyloxyphenyl)Phenylsulfonium Triflate (BVOPSTF)

A 3-neck-round bottom flask was fitted with a condenser, an addition funnel, nitrogen source, and a magnetic bar. Sodium hydroxide (8.64 g, 0.216 mol), bis(4-hydroxyphenyl)phenylsulfonium triflate (16 g, 0.036 mol) and DMSO (90 ml) were added to a round bottom flask under $N_2$. The mixture was heated to 60° C. for 1 hour. 2-chloroethyl vinylether (23 g, 0.216 mol) was added dropwise to the mixture via the addition funnel. The temperature was then increased to 80° C. and the reaction was held at that temperature for 5 hours. The reaction mixture was then allowed to cool down to room temperature. Thereafter, the reaction mixture was poured into diethyl ether to form three layers: aqueous, ether, and an oil. DI water was used to wash the ether solution 3 times. An oily layer was collected and concentrated to dryness. 12.9 g (61.5%) of bis(4-vinyloxyethyloxyphenyl)phenylsulfonium triflate was obtained. The structure was confirmed using $^1$H and $^{19}$F NMR.

Example 4

Preparation of Bis(4-vinyloxyethyloxyphenyl)Phenylsulfonium Nonaflate (BVOPSNF)

Bis(4-vinyloxyethyloxyphenyl)phenylsulfonium triflate (11.7 g, 0.02 mol) in 120 ml of methylene chloride, nanofluoro 1-butanesulfonic acid potassium salt (6.76 g, 0.02 mol) and 340 ml DI water were added to a 1000 ml round bottom flask fitted with mechanical stirrer and nitrogen source. The reaction mixture was stirred overnight at room temperature. Thereafter, the reaction mixture was washed with $CH_2Cl_2$ 3 times. The $CH_2Cl_2$ layer was collected and concentrated to afford the product, as a yellowish gel, 13.23 g (90%). The structure was confirmed using $^1$H and $^{19}$F NMR.

Example 5

Preparation of Bis(Bis(4-vinyloxyethyloxyphenyl) Phenylsulfonium)1,4-Perfluorobutanedisulfonate (BVOPSFBDS)

To a 1000 ml round bottom flask fitted with a mechanical stirrer and nitrogen source, bis(4-vinyloxyethyloxyphenyl)phenylsulfonium triflate (11.7 g, 0.02 mol), nanofluoro 1-butanesulfonic acid potassium salt (6.76 g, 0.02 mol) and 340 ml DI water were added. The reaction mixture was stirred overnight at room temperature. Thereafter, the reaction mixture was washed with $CH_2Cl_2$ 3 times. The $CH_2Cl_2$ layer was collected and concentrated to afford the product, as a yellowish gel, 13.23 g (90%). The structure was confirmed using $^1$H and $^{19}$F NMR.

Example 6

Preparation of Bis(Hydroxyphenyl)Sulfoxide

In a suitably sized container fitted with a mechanical stirrer, nitrogen source, and addition funnel, bis(4-hydroxyphenyl)sulfide (100 g, 0.458 moles) was dissolved in 100 mL of glacial acetic acid and the mixture cooled to 15° C. with an ice bath. Hydrogen peroxide 30% (51.94 g, 0.458 moles) was added slowly with stirring. The addition of hydrogen peroxide was done very slowly, stopping at times to add distilled water (10-20 mL) to act as a heat sink to avoid the temperature exceeding 40° C. After the addition of hydrogen peroxide was complete, the reaction mixture gradually cooled to room temperature over time (about 1 hour). The reaction mixture was stirred overnight and then 100 mL of distilled water was added, precipitating a white crystalline material. The material was dried at 40° C. under vacuum, giving 104 g of bis(hydroxyphenyl)sulfoxide (97% yield) (pure by $^1$H NMR).

Example 7

Preparation of Tris(Hydroxyphenyl)Sulfonium Mesylate

A four neck round bottomed flask was equipped with a mechanical stirrer, addition funnel, thermometer, and reflux column equipped with a nitrogen inlet. A solution of bis (hydroxyphenyl)sulfoxide (35.1 g, 0.165 moles), phenol (15.51, 0.165 moles) dissolved in methylene chloride (100 mL) was placed in the flask and stirred under nitrogen. In a separate flask, a solution of 82.5 mL of mesic acid and $P_2O_5$ was prepared by mixing these materials at 100° C. with stirring for 1 hour. The mesic acid/$P_2O_5$ mixture was added to the stirred mixture in the round bottom flask via the addition funnel over a period of 15 minutes under nitrogen. The reaction mixture was then left to stir overnight. The reaction mixture was then extracted with 1000 mL of ether to remove excess mesic acid. The water layer after stripping most of the water (60 g) contained the bulk of the tris(hydroxyphenylsulfonium)mesylate in addition to some mesic acid and residual water. 60 g of water was added to the stripped water layer, causing the precipitation of an oil. The oil was extracted with 2×10 mL of water. The residue was redissolved in 60 g of hot water, allowed to form an oil and washed for a final time with 2×10 mL water to yield 27.2 g of tris(hydroxyphenylsulfonium mesylate. The structure was confirmed using $^1$H NMR.

Example 8

Preparation of Tris(Hydroxyphenyl)Sulfonium Triflate (THPSTF)

In a suitably sized container fitted with a mechanical stirrer and nitrogen source, a solution of 26.65 g of tris(hydroxyphenylsulfonium mesylate was suspended in ethyl acetate (100 mL) was prepared and to which was added 200 mL of water followed by 11.28 g of sodium triflate. This mixture was stirred overnight, and the aqueous layer separated from the organic layer. The organic layer was exchanged with another 11.28 g of sodium triflate to give complete exchange. The organic layer was washed with 3×20 mL H$_2$O and then the solvent removed, triturated with pentane and subjected to a final drying to give 27.85 g of tris(hydroxyphenyl)sulfonium triflate. The structure was confirmed using $^1$H and $^{19}$F NMR.

Example 9

Preparation of Tris(4-vinyloxyethyloxyphenyl)Sulfonium Triflate

A three necked round bottomed flask was equipped with a mechanical stirrer, addition funnel and a condenser equipped with a nitrogen inlet. A solution of tris(4-hydroxyphenyl) sulfonium triflate from Example 8 (10 g, 0.0217 moles) dissolved in 51 mL of dry DMSO was prepared and added to the flask. To this mixture was added NaOH (5.65 g 0.14 moles) and the reaction mixture heated under nitrogen at 60° C. for ~1 hour until all the NaOH was dissolved. To this solution was added dropwise, using the addition funnel, 2-chloroethylvinyl ether (30 g, 0.28 moles) while heating the reaction mixture to 80° C. The mixture was stirred at 80° C. for 5 hours. After the reaction was complete, a white solid formed (NaCl from AgNO$_3$ test), which was filtered. The filtrate was diluted with 200 mL of water and treated with 200 mL of ether to form three layers. The aqueous layer was discarded and the two remaining organic layers were washed with 3×40 mL water. The stripped organic layer was triturated several times with ether to remove bis(4-vinyloxyethyloxyphenyl)sulfide impurity to give 6.63 g of tris(4-vinyloxyethyloxyphenyl) sulfonium nonaflate. The structure was confirmed using $^1$H and $^{19}$F NMR.

Example 10

Preparation of Tris(4-vinyloxyethyloxyphenyl)Sulfonium Nonaflate (TVOPSNF)

In a suitable container fitted with a mechanical stirrer and nitrogen source, a solution of tris(4-vinyloxyethyloxyphenyl) sulfonium triflate from Example 9 (3.32 g, 0.0049 moles) dissolved in 9 g of ethyl acetate was prepared. To this solution was added potassium nonaflate (3.34 g 0.0098 moles) suspended in 20 mL of water and the mixture stirred overnight at room temperature. The mixture was extracted by adding 10 mL ethyl acetate and 10 mL water and after removing the water layer washing the organic layer with 20 mL of water containing 3.34 g potassium nonaflate followed by 2×10 mL of distilled water. The ethyl acetate was then removed and the residue redissolved in methylene chloride to remove excess potassium nonaflate. 3.71 g of pure tris(4-vinyloxyethyloxyphenyl)sulfonium nonaflate was recovered. The structure was confirmed using $^1$H and $^{19}$F NMR.

Example 11

Preparation of Bis(tris(4-vinyloxyethyloxyphenyl)Sulfonium) 1,4-perfluorobutanedisulfonate (TVOPSFBDS)

The procedure of Example 5 was followed using tris(4-vinyloxyethyloxyphenyl)sulfonium triflate in place of bis(4-vinyloxyethyloxyphenyl)sulfonium triflate with three additional exchanges of potassium 1,4-perfluorobutanedisulfonate being used (4.33 grs twice; 5.57 grs third time) by dissolving the residue in acetone and adding the potassium 1,4-perfluorobutanedisulfonate dissolved in water. The final addition of potassium 1,4-perfluorobutanesulfonate solution was done by heated with stirring at 40° C. for 1 hour. The acetone was then removed on a roto-evaporator and the water layer removed by decantation. The oily residue was dissolved in 10 mL of methylene chloride, filtered to remove any residual potassium salt and the solvent was stripped away. This residue was redissolved in acetone and precipitated with water three times, followed by redissolution in methylene chloride and precipitation with pentane to give after drying 2.8 grams of pure product (81% yield). The structure was confirmed using $^1$H and $^{19}$F NMR.

Example 12

Preparation of Tris(4-vinyloxyethyloxyphenyl)Sulfonium 1.1,2,2,3,3-hexafluoropropane-1,3-disulfonimide (TVOPSHFPDI)

Tris(4-vinyloxyethyloxyphenyl)sulfonium triflate from Example 9 (2.00 g, 0.00298 moles) was transferred into a flask and dissolved in 5 mL of acetone. Lithium 1,1,2,2,3,3-hexafluoropropane-1,3-disulfonimide (from TCI) was dissolved in 3 mL of distilled water and added to the acetone solution of triflate salt. Enough acetone (35 mL) was added to this mixture to get a clear one phase solution. The reaction mixture was stirred overnight in a stoppered flask. The acetone was then removed under vacuum, and 50 mL of methylene chloride was added. The organic layer was extracted four times with 10 mL of distilled water. The final washed organic layer was stripped of solvent and dried overnight under high vacuum to give 2.40 g (99% yield) of an oil which was pure by $^1$H and $^{19}$F NMR.

Example 13

Preparation of Tetramethylammonium Deoxycholate (TMADOC)

In a suitable container fitted with a mechanical stirrer and nitrogen source, a solution of deoxycholic acid (5 g, 0.0127 moles) and tetramethylammonium hydroxide pentahydrate (2.3081 g, 0.0127 moles) dissolved in 40 mL of distilled water was prepared. The solution was stirred and a white powder was formed. The water was removed by freeze drying to obtain a white powder (5.69 g, 95% yield), tetramethylammonium deoxycholate, which was pure by $^1$H NMR.

Example 14

Preparation of Tetramethylammonium Lithocholate (TMALC)

In a suitable container fitted with a mechanical stirrer, a solution of lithocholic acid (5 g, 0.023277 moles) and tetramethylammonium hydroxide pentahydrate (2.406 g, 0.023277 moles) dissolved in 40 mL of distilled water was prepared. The solution was stirred and a white powder was formed. The water was removed by freeze drying to obtain a white powder (5.59 g, 94% yield), tetramethylammonium lithocholate, which was pure by $^1$H NMR.

Example 15

Preparation of Tetramethylammonium Cholate (TMAC)

In a suitable container fitted with a mechanical stirrer, a solution of cholic acid (5 g, 0.012238 moles) and tetramethylammonium hydroxide pentahydrate (2.406 g, 0.012238 moles) dissolved in 40 mL of distilled water was prepared. The solution was stirred and a white powder was formed. The water was removed by freeze drying to obtain a white powder (5.53 g, 94% yield), tetramethylammonium cholate, which was pure by $^1$H NMR.

Example 16

Preparation of Poly (4-hydroxyphenoxymethacrylate-co-tert-butylacrylate) 60/40 P(PQMA/TBA)

In a suitable container fitted with a mechanical stirrer, addition funnel, and nitrogen source, 4-hydroxyphenoxymethacrylate 16.86 g (94.6 mmol) and tert-butylacrylate 8.09 g (63.1 mmol) were dissolved in 66 g THF. The mixture was stirred under $N_2$ at room temperature for 20 minutes, and then heated to 70° C. 2,2'-azobisisobutyronitrile 5.05 g (30.8 mmol) in 4 g THF was added to the reaction mixture. The reaction mixture was stirred for additional 5 hours at 70° C. The reaction mixture was then cooled down to room temperature, diluted with additional 70 ml THF, and then added to a mixture of 300 ml butylacetate and 700 ml heptane mixture, causing a precipitate to form. The precipitate was filtered, added to 1000 ml heptane, filtered again, and then dried at 40° C. in a vacuum oven (95% yield). This material was found to have an $M_w$ of 19236 and a $M_n$ of 8920 by gel permeation (GPC) chromatography.

Example 17

Preparation of Poly(4-hydroxyphenoxymethacrylate-co-tert-butylacrylate-co-ethylcyclopentylacrylate) 60/20/20 P(PQMA/TBA/ECPA)

In a suitable container fitted with a mechanical stirrer and nitrogen source, 4-hydroxyphenoxymethacrylate 64.73 g (363.3 mmol), tert-butylacrylate 15.52 g (121.1 mmol) and ethylcyclopentylacrylate 20.37 g (121.1 mmol) were dissolved in 270 g THF. The mixture was stirred under $N_2$ at room temperature with for 20 minutes, and then heated to 70° C. 2,2'-azobisisobutyronitrile 19.38 g (118.2 mmol) in 20 g THF was added to the reaction mixture. The reaction mixture was stirred for additional 5 hours at 70° C. 4-methoxy phenol 6.01 g (48.4 mmol) was then added to the reaction mixture and the reaction mixture was cooled down to room temperature. The reaction mixture was then diluted with additional 300 ml THF, precipitated in 2500 ml heptane, filtered, reprecipitated in 2500 ml heptane, filtered, and dried at 40° C. in vacuum oven (95% yield). This material was found to have an $M_w$ of 20980 and a $M_n$ of 9237 by gel permeation (GPC) chromatography.

Examples 18 to 32 described the preparation of formulations which were used for testing different inventive compounds and/or compositions. The general procedure for preparing these solutions is as follows unless stated otherwise in the specific example itself:

Each formulation sample (30 g) was prepared at a 1.2 weight % level of total components apart from solvent and containing a crosslinkable inventive PAG compounds were also formulated with polymers from either Example 16 (poly (4-hydroxyphenoxymethacrylate-co-tert-butylacrylate) 60/40) (P(PQMA/TBA)) or Example 17 (4-hydroxyphenoxymethacrylate-co-tert-butylacrylate-co-ethylcyclopentylacrylate) 60/20/20) (P(PQMA/TBA/ECPA)) Also, added to the formulation were triethylamine (TEA), a crosslinking agent tris(4-vinyloxybutyl) 1,2,4-cyclohexanetricarboxylate (CHTA-BVE), a thermal acid generator (TAG) triethylammonium malonate (TEAM) (which is more fully described in Ser. No. 11/876,793, the contents of which are hereby incorporated herein by reference) and propylene glycol monomethyl ether (PGME) as the solvent. The PAG is added on a wt % basis of the polymer used. The freshly mixed solutions were left on the roller for at least 3 hours and then filtered using PTFE-filters with 0.2 μm pore diameter.

Examples 33 to 35 described the preparation of formulations which were used for testing inventive cross-linkable photodecomposable bases or quenchers. The general procedure for preparing these solutions is as follows unless stated otherwise in the specific example itself:

Each formulation sample (30 g) was prepared at a 1.2 weight % level of total components apart from solvent and containing a crosslinkable inventive photodecomposable base or quencher were also formulated with polymers from either Example 16 (poly(4-hydroxyphenoxymethacrylate-co-tert-butylacrylate) 60/40) (P(PQMA/TBA)) or Example 17 (4-hydroxyphenoxymethacrylate-co-tert-butylacrylate-co-ethylcyclopentylacrylate) 60/20/20) (P(PQMA/TBA/ECPA)) Also added, were a PAG as cited in the specific example, triethylamine (TEA), a crosslinking agent tris(4-vinyloxybutyl) 1,2,4-cyclohexanetricarboxylate (CHTA-BVE), a thermal acid generator (TAG) triethylammonium malonate (TEAM) and t propylene glycol monomethyl ether (PGME) as the solvent. The PAG is added on a wt % basis of the polymer used and the molar ratio of the crosslinking base with the PAG employed is identified. The freshly mixed solutions were left on the roller for at least 3 hours and then filtered using PTFE-filters with 0.2 μm pore diameter.

Example 18

P(PQMA/TBA) 10% TPSFPDS

The 1.2 weight % solution in PGME consisted of the following components as weight % of total components other than solvent: 64.98% of the polymer of Example 16, 15.60% of CHTA-BVE. 5.11% of TEA, 7.77% TEAM, 6.50% of the PAG bis(triphenylsulfonium) 1,4-perfluorobutanedisulfonate (3M).

Example 19

P(PQMA/TBA) 15% TPSFPDS

The 1.2 weight % solution in PGME consisted of the following components as weight % of total components other than solvent: 55.84% of the polymer of Example 16, 19.54% of CHTA-BVE. 6.45% of TEA, 9.79% TEAM, 8.38% of the PAG bis(triphenylsulfonium) 1,4-perfluorobutanedisulfonate.

Example 20

P(PQMA/TBA) 10% BHPPSNF

The 1.2 weight % solution in PGME consisted of the following components as weight % of total components other than solvent: 64.51% of the polymer of Example 16, 15.48% of CHTA-BVE. 5.11% of TEA, 8.45% TEAM, 6.48% of the PAG of Example 1.

Example 21

P(PQMA/TBA) 15% BHPPSNF

The 1.2 weight % solution in PGME consisted of the following components as weight % of total components other than solvent: 56.62% of the polymer of Example 16, 18.45% of CHTA-BVE. 6.09% of TEA, 10.35% TEAM, 8.49% of the PAG of Example 1.

Example 22

P(PQMA/TBA) 20% BHPPSNF

The 1.2 weight % solution in PGME consisted of the following components as weight % of total components other than solvent: 53.10% of the polymer of Example 16, 18.83% of CHTA-BVE. 6.09% of TEA, 11.23% TEAM, 10.62% of the PAG of Example 1.

Example 23

P(PQMA/TBA) 4% BHPPSFBDS

The 1.2 weight % solution in PGME consisted of the following components as weight % of total components other than solvent: 66.05% of the polymer of Example 16, 17.74% of CHTA-BVE 5.86% of TEA, 7.70% TEAM, 2.64% of the PAG of Example 2.

Example 24

P(PQMA/TBA) 15% BHPPSFBDS

The 1.2 weight % solution in PGME consisted of the following components as weight % of total components other than solvent: 56.05% of the polymer of Example 16, 19.47% of CHTA-BVE. 6.43% of TEA, 9.65% TEAM, 8.41% of the PAG of Example 2.

Example 25

P(PQMA/TBA) 20% BHPPSFBDS

The 1.2 weight % solution in PGME consisted of the following components as weight % of total components other than solvent: 52.44% of the polymer of Example 16, 20.09% of CHTA-BVE. 6.64% of TEA, 10.34% TEAM, 10.40% of the PAG of Example 2.

Example 26

P(PQMA/TBA) 2% BVOPSNF

The 1.2 weight % solution in PGME consisted of the following components as weight % of total components other than solvent: 69.31% of the polymer of Example 16, 17.06% of CHTA-BVE. 5.63% of TEA, 6.61% TEAM, 1.39% of the PAG of Example 4.

Example 27

P(PQMA/TBA) 6% BVOPSNF

The 1.2 weight % solution in PGME consisted of the following components as weight % of total components other than solvent: 68.92% of the polymer of Example 16, 15.68% of CHTA-BVE. 5.18% of TEA, 6.08% TEAM, 4.14% of the PAG of Example 4.

Example 28

P(PQMA/TBA) 10% BVOPSNF

The 1.2 weight % solution in PGME consisted of the following components as weight % of total components other than solvent: 68.54% of the polymer of Example 16, 14.33% of CHTA-BVE. 4.73% of TEA, 5.55% TEAM, 6.85% of the PAG of Example 4.

Example 29

P(PQMA/TBA/ECPA) 4% BVOPSNF

The 1.2 weight % solution in PGME consisted of the following components as weight % of total components other than solvent: 64.99% of the polymer of Example 17, 18.60% of CHTA-BVE. 6.14% of TEA, 7.67% TEAM, 2.60% of the PAG of Example 4.

Example 30

P(PQMA/TBA/ECPA) 4% TVOPSNF

The 1.2 weight % solution in PGME consisted of the following components as weight % of total components other than solvent: 69.18% of the polymer of Example 17, 15.94% of CHTA-BVE. 5.26% of TEA, 6.84% TEAM, 2.77% of the PAG of Example 10.

Example 31

P(PQMA/TBA/ECPA) 4% BVOPSFBDS

The 1.2 weight % solution in PGME consisted of the following components as weight % of total components other than solvent: 68.31% of the polymer of Example 17, 16.69% of CHTA-BVE. 5.51% of TEA, 6.76% TEAM, 2.73% of the PAG of Example 5.

Example 32

P(PQMA/TBA/ECPA) 4% TVOPSFBDS

The 1.2 weight % solution in PGME consisted of the following components as weight % of total components other than solvent: 65.18% of the polymer of Example 17, 17.96% of CHTA-BVE. 6.56% of TEA, 7.69% TEAM, 2.61% of the PAG of Example 11.

Example 33

P(PQMA/TBA/ECPA) 1.75% TPSFPDS no Crosslinking Base

The 1.2 weight % solution in PGME consisted of the following components as weight % of total components other than solvent: 68.68% of the polymer of Example 17, 17.54% of CHTA-BVE. 5.79% of TEA, 6.79% TEAM, 1.20% bis(triphenylsulfonium) 1,4-perfluorobutanedisulfonate.

Example 34

P(PQMA/TBA/ECPA) 1.75% TPSFPDS and Crosslinking Base from Example 13 (1:10 Molar Ratio Base:PAG)

The 1.2 weight % solution in PGME consisted of the following components as weight % of total components other than solvent: 68.63% of the polymer of Example 17, 17.54% of CHTA-BVE. 5.79% of TEA, 6.79% TEAM, 1.20% bis(triphenylsulfonium) 1,4-perfluorobutanedisulfonate, 0.06% crosslinking base from Example 13.

Example 35

P(PQMA/TBA/ECPA) 1.75% TPSFPDS and Crosslinking Base from Example 13 (1:30 Molar Ratio Base:PAG)

The 1.2 weight % solution in PGME consisted of the following components as weight % of total components other than solvent: 68.66% of the polymer of Example 17, 17.53% of CHTA-BVE. 5.79% of TEA, 6.79% TEAM, 1.20% bis(triphenylsulfonium) 1,4-perfluorobutanedisulfonate, 0.02% crosslinking base from Example 13.

General Evaluation Procedure

To evaluate the performance of cross-linkable PAG, two reference BARC systems were used. One is commercial organic BARC AZ® 1C5D from AZ® Electronic Materials and a second one were the above developable anti-reflective coating compositions solutions formulated with different levels of the low solubility PAG: bis-trisphenylphenylsulfonium 1,4-perfluorobutanedisulfonate which does not contain crosslinking moieties. Two different levels of bis(triphenylsulfonium) 1,4-perfluorobutanedisulfonate were used in reference materials: 10% bis(triphenylsulfonium) 1,4-perfluorobutanedisulfonate versus the polymer from Example 16 (Example 18) and 15% bis(triphenylsulfonium) 1,4-perfluorobutanedisulfonate versus the polymer from Example 16.

All processing was done on a Tokyo Electron Clean Track ACT 12 Track linked to a Nikon S306D (NA=0.85, Annular Illumination, (0.82/0.55)s, Reticle: Binary Mask) unless otherwise specified in discussion.

Film thickness was measured with Nanometrics Nanospec 8000. The coated wafer then exposed using Nikon 306D Illumination ID: 3 (0.85NA, ⅔ annular) and less aggressive binary exposure. It was processed as follows: SB=100° C./60 s, PEB=110° C./60 s, development time: 30 s (ACT12). The wafer is developed with a surfactant-free developer, AZ 300MIF, containing 2.38% tetramethyl ammonium hydroxide (TMAH).

For the reference samples with the conventional BARC, unprimed silicon wafers were coated with AZ® 1C5D (conditions: 2650 rpm, post applied bake (PAB) 200° C., 60 s) to form a BARC layer having a thickness of 37 nm. The resist, AZ® AX™ 2110P, was coated over the BARC layer (conditions: 1400 rpm, PAB (100° C./60 s), post exposure bake (PEB) (110° C./60 s)) to form a film having a thickness of about 210 nm. After exposure as described above, the wafers were developed in AZ® 300 MIF developer (23° C./30 s). In such systems the sizing dose for the 100 nm 1:1.5 and 120 1:1.1 features is ~30 mJ/cm². At this dose, the resist achieves the target CD. Since conventional BARCs are irreversibly crosslinked, no development into this layer occurs.

For the above developable anti-reflective coating compositions, including the reference materials, primed silicon wafers (HDMS vapor priming at 140° C. for 60 s) were coated with the above developable anti-reflective coating compositions (conditions: ~1500 rpm, PAB 120-180° C.) to form a developable anti-reflective coating layer of about 40 nm. The resist, AZ® AX™ 2110P, was coated over the developable anti-reflective coating layer (conditions: 1400 rpm, PAB (100° C./60 s), PEB (110° C./60 s)) to form a film having a thickness of about 210 nm. After exposure, the wafers were developed in AZ® 300 MIF developer (23° C./30 s). Under these conditions, in a film of AZ® AX™ 2110P, the sizing dose for the 100 nm 1:1.5 and 120 1:1.1 target features should be ~30 mJ/cm² (See above). Since the developable anti-reflective coating compositions are supposed to be developable, part of the evaluation is to ascertain how well developed the developable anti-reflective coating compositions is at 30 mJ/cm² and if any overexposure is required to fully develop the developable anti-reflective coating compositions.

A comparison was made of the performance of AZ® ArF 2110P on organic BARC 1C5D or developable anti-reflective coating compositions formulated with either the divinyloxy crosslinkable PAG from Example 4, BVOPSNF or the non-crosslinking PAG, bis(triphenylsulfonium) 1,4-perfluorobutanedisulfonate. For these developable anti-reflective coating compositions, different level of PAG loading were compared and judged by the ability of these formulations to resolve either 100 nm trenches or 120 nm trenches with a 1:1.5 pitch. All samples were evaluated as described above. The processing temperature used for the developable anti-reflective coating compositions was as follows: (FT: 40 nm~1500 rpm, PAB 120° C./60 sec)

Comparison of Non-Crosslinking PAG Bis(Triphenylsulfonium) 1,4-perfluorobutanedisulfonate Compared to Crosslinking PAGs This comparison was done with developable anti-reflective coating compositions formulated with the polymer made in Example 16. When using bis(triphenylsulfonium) 1,4-perfluorobutanedisulfonate, which does not have crosslinking groups, at levels lower than 10%, the developable anti-reflective coating composition was not developed at all, giving complete scumming at the resist-developable anti-reflective coating composition interface of the target features. Even samples with higher levels of bis(triphenylsulfonium) 1,4-perfluorobutanedisulfonate (Example 18 and 19) (10 and 15%) were unable to resolve these features without overexposing the features and generating large amount of undercut at the developable anti-reflective coating composition-resist interface.

In contrast, when using the crosslinking PAG from Example 4, much less scumming of the features is observed.

The formulations employed with increasing PAG level are Example 26 (2% of PAG from Example 4), Example 27 (6% of PAG from Example 4), and Example 28 (10% of PAG from Example 4). Even the lowest level give some partial clearance of the 100 nm trench features at the developable anti-reflective coating composition-resist interface. Complete clearance of the developable anti-reflective coating composition at the bottom of the trench occurred at a level between that of Example 27 which has partial clearance and Example 28 which has complete clearance of the developable anti-reflective coating compositions at the bottom of the trench at a dose of 33 mJ/cm$^2$, but showed a small undercut. Example 28 showed resist profiles similar to that seen with the standard BARC, 1C5D, between the doses of 33 and 36 mJ/cm$^2$.

Formulations with the di-hydroxy crosslinking PAG BHPPSNF from Example 1 were also evaluated at 10%, 15% and 20% PAG loading versus the polymer component from Example 16 (Example 20, Example 21 and 22 respectively). Also formulations with PAG BHPPSFBDS from Example 2 at a loading of 4%, 15% and 20% versus the same polymer (Examples 23, 24, 25 respectively) were evaluated.

Using the same lithographic conditions as described above, formulations containing PAG from Example 1 (BHPPSNF) or Example 2 (BHPPSFBDS), both of which have hydroxyl crosslinking groups, show better performance than those formulated with the corresponding amount of bis(triphenylsulfonium) 1,4-perfluorobutanedisulfonate, which does not have a crosslinking group. However, these formulations do not perform as well as the ones described previously with the vinyloxy PAGs (Examples 26-28) as they do not open the bottom developable anti-reflective coating pattern at nominal dose 30 mJ/cm$^2$ and need an overexposure at >42 mJ/cm$^2$ to resolve either 100 nm 1.1.5 or 120 nm 1:1.1 trench features without showing developable anti-reflective coating scumming. Of the two PAGs, BHPPSFBDS gave better performance than equivalent formulations containing BHPPSNF, giving better clearance of the developable anti-reflective coating at a lower dose with less undercut.

Other PAB temperature for the low solubility formulations were tested for the formulations containing the di-hydroxyl-PAG from Examples 1 (BHPPSNF) or 2 (BHPPSFBDS) or the di-vinyloxy PAG from Example 4 (PAB 130, 140, 150, 160, 170 and 180° C.). Using higher PAB temperatures does improve somewhat clearance of the developable anti-reflective coating containing the PAG from Example 4. For instance, using the Example 27 formulation containing 6% of PAG from Example 4, we increased the PAB from 130° C. to 180° C. in 10° C. increments and looked at the 120 nm 1:1.1 trench features. From these experiments, it is seen that at a dose of 27 mJ/cm$^2$ using a DBARC PAB of 120° C., a lot of developable anti-reflective coating scumming occurs, but that increasing the temperature gradually decreases scumming so that at 160° C. scumming is gone with a slight undercutting. Increasing the temperature further increases undercut of the resist features and decreases the overexposure margin. Similarly, the formulations described above (Examples 20-25) containing the di-OH PAG's from Examples 1 (BHPPSNF) or 2 (BHPPSFBDS) also show some improvement in scumming of 120 nm 1:1.1 trench features by going to higher temperature, but are not as good in decreasing scumming at a given PAG loading and temperature as those containing the divinyloxy PAG from Example 4. The same experiments done with bis(triphenylsulfonium) 1,4-perfluorobutanedisulfonate PAG, which does not crosslink, show much less improvement never giving a bake, or an overexposure sufficiently high to completely remove developable anti-reflective coating scumming.

Experiments were also done with developable anti-reflective coating formulations containing the polymer from Example 17. In these experiments, we compared the behavior of formulations in achieving 100 nm 1:1.5 trenches using the exposure conditions described above. These formulations containing 4% of PAG from Example 4 (Example 29); 4% of PAG from Example 10 (Example 30), of PAG from Example 5 (Example 31) and 4% the PAG from Example 11 (Example 32) to each other and to the behavior on the standard BARC 1C5D. These formulations are made with PAG's with increasing numbers of vinyloxy functionalities per PAG molecule. For instance, the PAG from Example 4 has two vinyloxy moieties, the PAG from Example 10 has three vinyloxy moieties, the PAG from Example 5 has four vinyloxy moieties and finally the PAG from Example 11 (TVOPSFB) has six vinyloxy moieties per molecule. All these crosslinking PAG materials show a far decreased formation of the interlayer scum that is seen with the non-crosslinking PAG bis(triphenylsulfonium) 1,4-perfluorobutanedisulfonate. Comparing the crosslinking PAG formulations to each other It is observed that the PAG from Example 10 and PAG from Example 5 give no formation at all of the interlayer scumming at the dose of 30 mJ/cm$^2$ while the PAG from Example 4 formulation gives a slight formation of interlayer scum at this dose. The formulations using the PAG from Example 11 do not give interlayer scumming but do give a developable anti-reflective coating layer that is more difficult to clear giving some bottom scumming of the developable anti-reflective coating unlike the other formulations containing the PAG's with fewer crosslinking groups. Finally, overall, developable anti-reflective coating undercut is apparently improved with increasing number of crosslinkable vinyloxy function group as well.

Performance of Crosslinking Base of Example 13.

To evaluate the performance of cross-linkable base from Example 13, the commercial BARC AZ® 1C5D and several developable anti-reflective coating systems based on the polymer from Example 17 were compared. For the commercial BARC sample AZ® 1C5D this was done with a 210 nm thick film of AZ® AX™ 2110P in the same way as previously described above. For the developable anti-reflective coating samples, this was done by again coating and baking the commercial resist AZ® AX™ 2110P in the same way as previously described above. Under these conditions, in a film of AZ® AX™ 2110P, with the sizing dose for the 100 nm 1:1.5 target features on AZ® 1C5D should was 30 mJ/cm$^2$ (See above). For the developable anti-reflective coating formulations we compared the formulation described in Example 33, which contains the polymer from Example 17, which contains 1.75% bis(triphenylsulfonium) 1,4-perfluorobutanedisulfonate (the non-crosslinking PAG) with no crosslinking base added to that of the formulation of Example 34 which contained 1.75% bis(triphenylsulfonium) 1,4-perfluorobutanedisulfonate but also contained crosslinking base from Example 13, crosslinking base (1:10 molar ratio Base:PAG) and also to the formulation of Example 35 which contained 1.75% bis(triphenylsulfonium) 1,4-perfluorobutanedisulfonate and crosslinking base from Example 13 (1:30 molar ratio Base:PAG). The sample containing no added crosslinking base from Example 13 when using a PAB temperature for the developable anti-reflective coating of 160° C. showed profound interlayer scumming between the resist and developable anti-reflective coating and suffered pattern collapse due to undercut of the developable anti-reflective coating beneath the resist at doses higher than 39 mJ/cm$^2$. In contrast, the formulations of Example 34 and 35 containing crosslinking base from Example 13 in a 1:10 and 1:30 Base:PAG ratio showed no pattern collapse even at a dose of 42 mJ/cm² because these formulations suffered far less undercut underneath the interlayer scum between developable anti-reflective coating and resist than was observed in the formulation without added crosslinking base from Example 13 (Example 33). When using a higher PAB temperature for the developable anti-reflective coating of 170° C., the developable anti-reflective coating formulation without added crosslinking base (Example 33) suffers pattern collapse because of undercut doses higher than 33 mJ/cm². The developable anti-reflective coating sample which containing crosslinking base from Example 13 in a 1:10 Base:PAG ratio (Example 34) showed pattern collapse only at 39 mJ/cm². This improvement was because the addition of the crosslinking base decreases the undercut upon overexposure. At this higher developable anti-reflective coating PAB curing temperature the sample which containing crosslinking base from Example 13 in a lower amount versus PAG (1:30 Base:PAG ratio) (Example 35) did not show a significant improvement in the collapse margin.

The foregoing description of the invention illustrates and describes the present invention. Additionally, the disclosure shows and describes only certain embodiments of the invention but, as mentioned above, it is to be understood that the invention is capable of use in various other combinations, modifications, and environments and is capable of changes or modifications within the scope of the inventive concept as expressed herein, commensurate with the above teachings and/or the skill or knowledge of the relevant art. The embodiments described hereinabove are further intended to explain best modes known of practicing the invention and to enable others skilled in the art to utilize the invention in such, or other, embodiments and with the various modifications required by the particular applications or uses of the invention. Accordingly, the description is not intended to limit the invention to the form disclosed herein. Also, it is intended that the appended claims be construed to include alternative embodiments.

The invention claimed is:

1. A positive bottom photoimageable antireflective coating composition which is capable of being developed with an aqueous alkali developer and which is, wherein the antireflective coating composition comprises a polymer and one or more photoactive compounds having the formula

where W is PAG; where PAG is a photoacid generator; L is a direct bond or a linking group, G is G2, where G2 is OCH=CH₂; and p is 2 to 6, further where the polymer comprises at least one unit of acrylic or methacrylic acid protected with an acid labile group and further the amount of the unit ranges from 5-95 mole %.

2. The composition of claim 1 wherein PAG is selected from onium salts, diazomethane derivatives, glyoxime derivatives, bissulfone derivatives, sulfonic acid esters of N-hydroxyimide compounds, β-ketosulfonic acid derivatives, disulfone derivatives, nitrobenzylsulfonate derivatives, sulfonate derivatives, benzyloxysulfonylbenzene derivatives, and mixtures thereof.

3. The composition of claim 1 further comprising Q-(L-(G1))$_p$, where L is a direct bond or a linking group, G1 is OH or OCH=CH₂, and Q is selected from the group consisting of;

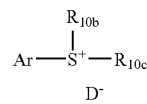

where Ar is an unsubstituted aryl group of 6 to 20 carbon atoms, substituted aryl group of 6 to 20 carbon atoms; $R_{10b}$ and $R_{10c}$ are independently selected from unsubstituted straight, branched or cyclic alkyl, substituted straight, branched or cyclic alkyl, straight, branched or cyclic alkenyl, straight, branched or cyclic alkyl containing one or more O atoms, straight, branched or cyclic alkenyl groups optionally containing one or more O atoms, aryl groups of 6 to 20 carbon atoms, aralkyl of 7 to 12 carbon atoms, aryloxoalkyl groups of 7 to 12 carbon atoms, $R_{10b}$ and $R_{10c}$, taken together, form a ring in which each of $R_{10b}$ and $R_{10c}$ are alkylene groups of 1 to 6 carbon atoms when they form a ring, and D⁻ is a basic anion having a pK$_a$ value of −3 to +7; and, where $R_a$ is selected from $(CH_2)_{i4}$, where i4 is 0 or 1, O and S; $R_{50}$ and $R_{60}$ are independently selected from $R_{10b}$, and $R_{50}$ and $R_{60}$ together with the S atom to which they are attached form a 5-, 6-, or 7-membered ring; $R_{80}$, $R_{90}$, and $R_{100}$ each individually are selected from $C_{1-4}$ alkyl, $C_{1-4}$ alkoxy, and halide; i1 and i2 are each 1 to 4; i3 is 1 to 5.

4. The composition of claim 1 wherein the polymer further comprises at least one recurring unit with an absorbing chromophore.

5. The composition of claim 1 further comprising a dye.

6. The composition of claim 1 where the composition further comprises a crosslinking component.

7. The composition of claim 1 which further comprises one or more quenchers having the formula Q-(L-(G1))$_p$ Q is a quencher, L is a direct bond or a linking group, G1 is OH or OCH=CH₂, where Q is selected from the group consisting of primary, secondary and tertiary aliphatic amines, aromatic amines, heterocyclic amines, nitrogen-containing compounds with a carboxy group, nitrogen containing compounds with a sulfonyl group, nitrogen-containing compounds with a hydroxy group, nitrogen-containing compounds with a hydroxyphenyl group, alcoholic nitrogen-containing compounds, amide derivatives, imide derivatives, nitrogen-containing compound having one or more oxygen atoms, and a compound having the formula

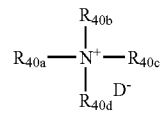

where $R_{40a}$, $R_{40b}$, $R_{40c}$, and $R_{40d}$ are independently selected from hydrogen, alkyl, alkenyl, alkyl containing one or more O atoms, alkenyl groups optionally containing one or more O atoms, aryl groups of 6 to 20 carbon atoms, aralkyl of 7 to 12 carbon atoms, aryloxoalkyl of 7 to 12 carbon atoms, $R_{40b}$ and $R_{40c}$ taken together form a ring in which each of $R_{40b}$ and $R_{40c}$ are alkylene groups of 1 to 6 carbon atoms, and D⁻ is a basic anion having a pK$_a$ value of −3 to +7.

8. The composition of claim 1 which further comprises a thermal acid generator.

9. The composition of claim 1 wherein the photoactive compound is selected from a group consisting of compound selected from bis(4-vinyloxyethyloxyphenyl)phenylsulfonium triflate, bis(4-vinyloxyethyloxyphenyl)phenylsulfonium nonaflate, bis(4-vinyloxyethyloxyphenyl)phenylsulfonium 10-camphorsulfonate, bis(4-vinyloxyethyloxyphenyl) phenylsulfonium cyclohexane sulfamate, bis(4-vinyloxyethyloxyphenyl)phenylsulfonium tris (trifluoromethanesulfonyl)methide, bis(bis(4-vinyloxyethyloxyphenyl)phenylsulfonium) 1,4-perfluorobutanedisulfonate, tris(4-vinyloxyethyloxyphenyl)sulfonium nonaflate, bis (tris(4-vinyloxyethyloxyphenyl)sulfonium) 1,4-perfluorobutanedisulfonate, tris(4-vinyloxyethyloxyphenyl)sulfonium 1.1,2,2,3,3-hexafluoropropane-1,3-disulfonimide, N-trifluoromethylsulfonyloxy-3,6-divinyloxyethoxy-1,8-naphthalimide, p-nitrobenzyl-9,10-divinyloxyethoxy anthracene-2-sulfonate, bis(4-vinyloxyethyloxyphenyl)iodonium 10-camphorsulfonate, bis(4-vinyloxyethyloxyphenyl)iodonium cyclohexane sulfamate, bis(4-vinyloxyethyloxyphenyl)iodonium 4-vinyloxyethyloxy-10-camphorsulfonate, bis(4-vinyloxyethyloxyphenyl)iodonium 4-vinyloxyethyloxy-cyclohexane sulfamate, bis(4-vinyloxyethyloxyphenyl)iodonium iris (trifluoromethanesulfonyl)methide, bis (bis(4-vinyloxyethyloxyphenyl)iodonium) 1,4-perfluorobutanedisulfonate, bis(4-vinyloxyethyloxyphenyl) iodonium 1.1,2,2,3,3-hexafluoropropane-1,3-disulfonimide, bis(4-vinyloxyethyloxyphenyl)iodonium 1,1,1,2-tetrafluoroethoxyoctafluorobutanesulfonate, tris(4-vinyloxyethyloxyphenyl)sulfonium 1,1,1,2-tetrafluoroethoxyoctafluorobutanesulfonate, bis(4-vinyloxyethyloxyphenyl) phenylsulfonium 1,1,1,2-tetrafluoroethoxyoctafluorobutanesulfonate, and bis(4-vinyloxyethyloxyphenyl)iodonium 1,1,1,2-tetrafluoroethoxyoctafluorobutanesulfonate.

10. A coated substrate comprising: a substrate having thereon a layer of the first coating composition of claim 1.

11. A process for forming an image comprising: a) forming a coating of the bottom photoimageable antireflective coating composition of claim 1 on a substrate; b) baking the antireflective coating, c) providing a coating of a top photoresist layer over the antireflective coating; d) imagewise exposing the photoresist and antireflective coating layers to actinic radiation of same wavelength; e) post-exposure baking the photoresist and antireflective coating layers on the substrate; and, f) developing the photoresist and antireflective coating layers with an aqueous alkaline solution.

12. The positive bottom photoimageable antireflective coating composition of claim 1, where the photoacid generator W, is selected from P1d, P1e and P1f,

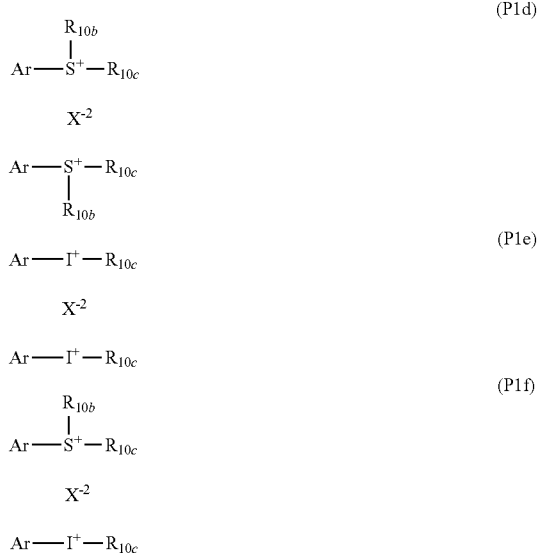

wherein Ar is an unsubstituted or substituted aryl group of 6 to 20 carbon atoms, $R_{10b}$ and $R_{10c}$ independently represent unsubstituted or substituted alkyl, unsubstituted or substituted alkenyl and unsubstituted or substituted aryl groups of 6 to 20 carbon atoms, aralkyl groups of 7 to 12 carbon atoms, aryloxoalkyl group of 7 to 12 carbon atoms, alkyl containing one or more O atoms, alkenyl group containing one or more O atoms, and $R_{10b}$ and $R_{10c}$, together form a ring; and, $X^{-2}$ is a $Q\text{-}R_{500}\text{—}SO_3^-$, where Q is selected from $^-O_3S$, $^-O_2C$, and $^-J$;

$R_{500}$ is a group selected from unsubstituted or substituted alkyl, unsubstituted or substituted cycloalkyl, unsubstituted or substituted aryl, and combinations thereof, and J is selected from fluoride, chloride, bromide and iodide, and further wherein (L-G))p is attached to either the cationic, anionic or both the cationic and anionic portion of P1d, P1e, or P1f to form W-(L-G))p.

* * * * *